US009827421B2

(12) United States Patent
Greiner et al.

(10) Patent No.: US 9,827,421 B2
(45) Date of Patent: *Nov. 28, 2017

(54) METHODS AND SYSTEMS FOR TREATING A CHRONIC LOW BACK PAIN CONDITION USING AN IMPLANTABLE ELECTROACUPUNCTURE DEVICE

(71) Applicant: Valencia Technologies Corporation, Valencia, CA (US)

(72) Inventors: Jeffrey H. Greiner, Valencia, CA (US); David K. L. Peterson, Valencia, CA (US); Chuladatta Thenuwara, Castaic, CA (US); Stacy Greiner Chambliss, Valencia, CA (US)

(73) Assignee: Valencia Technologies Corporation, Valencia, CA (US)

( * ) Notice: Subject to any disclaimer, the term of this patent is extended or adjusted under 35 U.S.C. 154(b) by 28 days.

This patent is subject to a terminal disclaimer.

(21) Appl. No.: 14/811,633

(22) Filed: Jul. 28, 2015

(65) Prior Publication Data
US 2015/0328460 A1 Nov. 19, 2015

Related U.S. Application Data

(63) Continuation-in-part of application No. 13/796,314, filed on Mar. 12, 2013, now Pat. No. 9,327,134, and
(Continued)

(51) Int. Cl.
*A61N 1/00* (2006.01)
*A61N 1/36* (2006.01)
(Continued)

(52) U.S. Cl.
CPC ....... *A61N 1/36071* (2013.01); *A61N 1/0551* (2013.01); *A61N 1/36175* (2013.01);
(Continued)

(58) Field of Classification Search
CPC .................................. A61N 1/3756
See application file for complete search history.

(56) References Cited

U.S. PATENT DOCUMENTS

| 4,031,899 A | 6/1977 | Renirie |
| 4,157,720 A | 6/1979 | Greatbatch |

(Continued)

FOREIGN PATENT DOCUMENTS

| EP | 1145736 | 10/2001 |
| WO | WO-01/41869 | 6/2001 |

(Continued)

OTHER PUBLICATIONS

Cheung, "The Mechanism of Acupuncture Therapy and Clinical Case Studies", Taylor and Francis, published in London. 2001. ISBN 0-415-27254-8. The Forward, Chapters 1-3, and 5.
(Continued)

*Primary Examiner* — Michael Carey
*Assistant Examiner* — Elizabeth K So
(74) *Attorney, Agent, or Firm* — ALG Intellectual Property, LLC

(57) ABSTRACT

An exemplary method of treating a chronic low back pain condition in a patient includes 1) generating, by an electroacupuncture device implanted beneath a skin surface of the patient at at least one of acupoints BL22, BL23, BL24, BL25, and BL26 within the patient, stimulation sessions at a duty cycle that is less than 0.05, wherein the duty cycle is a ratio of T3 to T4 and each stimulation session included in the stimulation sessions has a duration of T3 minutes and occurs at a rate of once every T4 minutes, and 2) applying, by the electroacupuncture device, the stimulation sessions to the target tissue location in accordance with the duty cycle.

12 Claims, 34 Drawing Sheets

Related U.S. Application Data a continuation-in-part of application No. 13/598,582, filed on Aug. 29, 2012, now Pat. No. 8,965,511, and a continuation-in-part of application No. 13/622,653, filed on Sep. 19, 2012, now Pat. No. 8,996,125, and a continuation-in-part of application No. 13/630,522, filed on Sep. 28, 2012, now Pat. No. 9,173,811.

(60) Provisional application No. 62/030,589, filed on Jul. 29, 2014, provisional application No. 62/091,333, filed on Dec. 12, 2014, provisional application No. 61/609,875, filed on Mar. 12, 2012, provisional application No. 61/672,257, filed on Jul. 16, 2012, provisional application No. 61/672,661, filed on Jul. 17, 2012, provisional application No. 61/673,254, filed on Jul. 19, 2012, provisional application No. 61/674,691, filed on Jul. 23, 2012, provisional application No. 61/676,275, filed on Jul. 26, 2012.

(51) Int. Cl.
*A61N 1/05* (2006.01)
*A61N 1/372* (2006.01)
*A61N 1/375* (2006.01)
*A61N 1/378* (2006.01)

(52) U.S. Cl.
CPC ....... *A61N 1/3756* (2013.01); *A61N 1/37205* (2013.01); *A61N 1/37223* (2013.01); *A61N 1/36125* (2013.01); *A61N 1/3758* (2013.01); *A61N 1/3782* (2013.01); *H01L 2224/48091* (2013.01); *Y10T 29/49002* (2015.01)

(56) References Cited

U.S. PATENT DOCUMENTS

| | | | |
|---|---|---|---|
| 4,256,115 A * | 3/1981 | Bilitch | A61N 1/0587 607/135 |
| 4,345,604 A | 8/1982 | Renirie | |
| 4,528,072 A | 7/1985 | Kurosawa et al. | |
| 4,535,784 A | 8/1985 | Rohlicek et al. | |
| 4,566,064 A | 1/1986 | Whitaker | |
| 5,195,517 A | 3/1993 | Chen | |
| 5,199,428 A | 4/1993 | Obel et al. | |
| 5,211,175 A | 5/1993 | Gleason et al. | |
| 5,250,068 A | 10/1993 | Ideguchi et al. | |
| 5,251,637 A | 10/1993 | Shalvi | |
| 5,372,605 A | 12/1994 | Adams et al. | |
| 5,544,656 A | 8/1996 | Pitsillides et al. | |
| 5,609,617 A | 3/1997 | Shealy et al. | |
| 5,707,400 A | 1/1998 | Terry, Jr. et al. | |
| 5,891,181 A | 4/1999 | Zhu | |
| 6,006,134 A | 12/1999 | Hill et al. | |
| 6,178,352 B1 | 1/2001 | Gruzdowich et al. | |
| 6,393,324 B2 | 5/2002 | Gruzdowich et al. | |
| 6,522,926 B1 | 2/2003 | Kieval et al. | |
| 6,658,298 B2 | 12/2003 | Gruzdowich et al. | |
| 6,735,475 B1 | 5/2004 | Whitehurst et al. | |
| 6,839,596 B2 | 1/2005 | Nelson et al. | |
| 6,950,707 B2 | 9/2005 | Whitehurst | |
| 6,978,174 B2 | 12/2005 | Gelfand et al. | |
| 7,003,352 B1 | 2/2006 | Whitehurst | |
| 7,013,177 B1 | 3/2006 | Whitehurst et al. | |
| 7,046,499 B1 | 5/2006 | Imani et al. | |
| 7,136,701 B2 | 11/2006 | Greatbatch et al. | |
| 7,155,279 B2 | 12/2006 | Whitehurst et al. | |
| 7,162,303 B2 | 1/2007 | Levin et al. | |
| 7,171,266 B2 | 1/2007 | Gruzdowich et al. | |
| 7,203,548 B2 | 4/2007 | Whitehurst et al. | |
| 7,292,890 B2 | 11/2007 | Whitehurst et al. | |
| 7,321,792 B1 | 1/2008 | Min et al. | |
| 7,373,204 B2 | 5/2008 | Gelfand et al. | |
| 7,440,806 B1 | 10/2008 | Whitehurst et al. | |
| 7,444,180 B2 | 10/2008 | Kuzma et al. | |
| 7,610,100 B2 | 10/2009 | Jaax et al. | |
| 7,620,451 B2 | 11/2009 | Demarais et al. | |
| 7,657,316 B2 | 2/2010 | Jaax et al. | |
| 7,962,219 B2 | 6/2011 | Jaax et al. | |
| 9,078,801 B2 * | 7/2015 | Greiner | A61H 39/002 |
| 9,327,134 B2 * | 5/2016 | Greiner | A61N 1/3756 |
| 2002/0016568 A1 | 2/2002 | Lebel et al. | |
| 2003/0078624 A1 | 4/2003 | Carlson et al. | |
| 2003/0078642 A1 | 4/2003 | Malaney et al. | |
| 2003/0158588 A1 | 8/2003 | Rizzo et al. | |
| 2003/0171790 A1 | 9/2003 | Nelson et al. | |
| 2003/0187485 A1 | 10/2003 | Sturman et al. | |
| 2003/0195583 A1 | 10/2003 | Gruzdowich et al. | |
| 2003/0195585 A1 | 10/2003 | Gruzdowich et al. | |
| 2003/0220668 A1 | 11/2003 | Shealy | |
| 2003/0236558 A1 | 12/2003 | Whitehurst et al. | |
| 2005/0107832 A1 | 5/2005 | Bernabei | |
| 2005/0228460 A1 | 10/2005 | Levin et al. | |
| 2005/0234533 A1 | 10/2005 | Schulman et al. | |
| 2006/0041283 A1 | 2/2006 | Gelfand et al. | |
| 2006/0167526 A1 * | 7/2006 | Wan | A61H 39/002 607/46 |
| 2006/0184209 A1 | 8/2006 | John et al. | |
| 2007/0005119 A1 | 1/2007 | Crohn | |
| 2007/0219595 A1 | 9/2007 | He | |
| 2007/0255319 A1 | 11/2007 | Greenberg et al. | |
| 2007/0265680 A1 | 11/2007 | Liu | |
| 2008/0015572 A1 | 1/2008 | Johnson et al. | |
| 2008/0091255 A1 | 4/2008 | Caparso et al. | |
| 2008/0097529 A1 | 4/2008 | Parramon et al. | |
| 2009/0192555 A1 | 7/2009 | Schleicher et al. | |
| 2009/0210026 A1 | 8/2009 | Solberg et al. | |
| 2009/0292341 A1 | 11/2009 | Parramon et al. | |
| 2010/0042137 A1 | 2/2010 | Oronsky et al. | |
| 2010/0069992 A1 | 3/2010 | Aghassian et al. | |
| 2010/0211132 A1 | 8/2010 | Nimmagadda et al. | |
| 2010/0324624 A1 | 12/2010 | Chang | |
| 2010/0327887 A1 | 12/2010 | Denison et al. | |
| 2011/0106219 A1 | 5/2011 | Cauller et al. | |
| 2011/0106220 A1 | 5/2011 | DeGiorgio et al. | |
| 2011/0112603 A1 | 5/2011 | DeGiorgio et al. | |
| 2011/0172739 A1 | 7/2011 | Mann et al. | |
| 2011/0218589 A1 | 9/2011 | DeGiorgio et al. | |
| 2011/0218590 A1 | 9/2011 | DeGiorgio et al. | |
| 2012/0022612 A1 | 1/2012 | Littlewood et al. | |
| 2012/0259390 A1 | 10/2012 | Canion | |
| 2013/0041396 A1 | 2/2013 | Ryotokuji | |

FOREIGN PATENT DOCUMENTS

| | | |
|---|---|---|
| WO | WO-02/00294 | 1/2002 |
| WO | WO-2014/159433 | 10/2014 |
| WO | WO-2014/165111 | 10/2014 |

OTHER PUBLICATIONS

Li, "Neural Mechanism of Electroacupuncture's Hypotensive Effects", *Autonomic Neuroscience: Basic and Clinical 157* (2010) 24-30.

"Acupuncture Today: Electroacupuncture", Feb. 1, 2004. Retrieved on-line Aug. 9, 2006 at http://www.acupuncturetoday.com/abc/electroacupuncture.php.

"Who Standard Acupuncture Point Locations in the Western Pacific Region", published by the World Health Organization (WHO), Western Pacific Region, 2008 (updated and reprinted 2009), ISBN 978 92 9061 248 7. *The Table of Contents, Forward* (p. v-vi), and *General Guidelines for Acupuncture Point Locations* (pp. 1-21), as well a, as pp. 45, 64, 151, and 154.

"Acupuncture", http://en.wikipedia.org/wiki/Acupuncture.

"Electroacupuncture", http://en.wikipedia.org/wiki/Electroacupuncture.

"Delta-sigma Modulation", http://en.wikipedia.org/wiki/Delta-sigma_modulation.

Song, Kiseok "The Compact Electro-Acupuncture System for Multi-Modal Feedback Electro-Acupuncture Treatment", *34th*

(56) References Cited

OTHER PUBLICATIONS

*Annual International Conference of the IEEE EMBS*, San Diego, CA, USA, Aug. 28-Sep. 1, 2012.

Luo, et al., "Electro-acupuncture vs. amitriptyline in the treatment of depressive states", *Journal of Traditional Chinese Medicine 1985*; 5:3-8.

Luo, et al., "Clinical research on the therapeutic effect of the electro-acupuncture treatment in patients with depression", *Psychiatry Clin Neurosci 1998*; 52 Suppl: S338-S340.

Luo, et al., "Comparative study of electroacupuncture and fluoxetine for treatment of depression", *Chin J. Psychiatry*, 2003; 36(4): 215. Chinese with English abstract.

Leo, Salvador "A systematic review of randomized controlled trials of acupuncture in the treatment of depression", *Journal of Affective Disorders 2006*.

Fu, et al., "Acupuncture for treatment of depressive neurosis: a multi-center randomized controlled study", 2008. Zhongguo Zhen Jiu. *Chinese Acupuncture and Moxibustion*. 28(1): 3-6. Chinese with English Abstract.

Wang, et al., "Clinical analysis of common psychosis treated by electroacupuncture in 129 cases", *Journal of Clinical Acupuncture and Moxbiusion*. 1999; (1): 42.

Chen, E. "Cross-Sectional Anatomy of Acupoints", *Churchill Livingstone*. 1995.

Shrader, L. et al., "Trigeminal nerve stimulation in major depressive disorder: first proof of concept in an open pilot trial", *Epilepsy Behav 2011*; 22:475-8.

"Trigeminal Nerve", http://en.wikipedia.org/wiki/Irigeminalnerve.

Longhurst, J.C. "Central & Peripheral Neural Mechanisms of Acupuncture in Myocardial Ischemia", *International Congress Series 1238* (2002) 79-87.

Mannheimer, C. et al., "The Problem of Chronic Refractory Angina", *European Heart Journal* (2002) 23, 355-370.

Sanderson, J. E. "Electrical neurostimulators for pain relief in angina", *British Heart Journal* (1990) 63:141-143.

Zhou, WY et al., "Brain stem mechanisms underlying acupuncture modality-related modulation of cardiovascular responses in rats", *J Appl Physiol 2005*, 99:851-860.

Zhou, W. et al., "Afferent mechanisms underlying stimulation of modality-related modulation of acupuncture-related cardiovascular responses", *J Appl Physiol 2005*, 98:872-880.

Gao, J. et al., "Acupuncture pretreatment protects heart from injury in rats with myocardial ischemia and reperfusion via inhibition of the B1-adrenoceptor signaling pathway", *Life Sciences 80* (2007) 1484-1489.

Li, P. et al., "Reversal of Reflex-Induced Myocardial Ischemia by Median Nerve Stimulation: A Feline Model of Electroacupuncture", *American Heart Association Circulation 1998*, 97: 1186-1194.

Middlekauff, HR et al., "Acupuncture inhibits sympathetic activation during mental stress in advanced heart failure patients", *J Cardiac Failure*: 8:399-406 (2002).

Jacobsson, F. et al., "The effect of transcutaneous electric nerve stimulation in patients with therapy resistant hypertension", *J. Hum. Hypertens*. 14(12), 795-798 (2000).

Oka, T. et al., "Treatment of angina pectoris with acupuncture—role of "Neiguan"", *Jpn J. Oriental Med*. 38: 85-88.

Kurono, Y. et al., "The effect of acupuncture on the coronary arteries as evaluated by coronary angiography: a preliminary report", *Am J Chin Med 30*: 387-396 (2002).

Lin, D. et al., "Effect of electroacupuncture on Neiguan and Shenmen Points on heart function after coronary artery bypass grafting in coronary heart disease", *Modern Journal of Integrated Traditional Chinese and Western Medicine*: 18:2241-41. Abstract. (2009).

Tjen-A-Looi, SC et al., "Medullary substrate and differential cardiovascular responses during stimulation of specific acupoints", *Am J Physiol Regullnteg Camp Physiol 2004*, 287:R852-R862.

Liu, XQ et al., "Influence of acupuncture on epicardial monophasic action potential in vivo in dog with myocardial infarction", *Tianjin Journal of Traditional Chinese Medicine 22*: 480-481 (2005)

Yang, "Cardioprotective effects of electroacupuncture pretreatment on patients undergoing heart valve replacement surgery: a randomized controlled trial", *Ann Thorac Surg 89*:781-6 (2010).

Ballegaard, S. et al., "Acupuncture in severe, stable angina pectoris: a randomized trial", *Acta Med Scand 220: 307-13* (1986).

Richter, A. et al., "Effect of acupuncture in patients with angina pectoris", *Eur Heart J*: 12:175-8 (1991).

Quirico, PE et al., "Teaching Atlas of Acupuncture", vol. 1: Channels and Points. pp. 180-196.

Wang, JD et al., "An alternative method to enhance vagal activities and suppress sympathetic activities in humans", *Autonomic Neuroscience: Basic and clinical100*: 90-95. (2002).

Xie, L. et al., "124 cases of dyssomnia treated with acupuncture at sishencong points", *J. Tradil. Chin. Med. 14*, 171-173 (1994).

Han, Y. et al., "Influence of needling with the combination of back-shu and front-mu points in the heart and pericardium meridian on the electrocardiography of patients with coronary heart disease", *Chinese Acupuncture and Moxibustion*Jun. 1994. Abstract. (1994).

Cal, RL et al., "Effects of electroacupuncture of "Shenmen" (HT 7) and "Zhizheng" (SI 7) on cardiac function and electrical activities of cardiac sympathetic nerve in acute myocardial ischemia rabbits", Zhen Ci Yan Jiu. 2007; 32(4): 243-6. Abstract (2007).

Yang, YF et al., "Different effects of acupuncture at shenmen (HT7)-Tongli(HT5) and Shenmen-Neiguan (PC6) points on heart rate variability in healthy subjects", *J Chin Med*. 2009; 20 (3,4): 97-106 (2009).

Xiao-Min, T et al., "Experimental study on electroacupuncture in "Neiguan" (PC6) on congestive heart failure rats model and its effect of Angll, ET, CGRP", *Journal of Chengdu University of Traditional Chinese Medicine*. Jan. 2007. Abstract. (2007).

Xu, FH et al., "Clinical observation on acupuncture combined with medication for intractable angina pectoris", Zhongguo Zhen Jiu. 25(2): 89-91, Abstract (2005).

Shi, X et al., "Effect of acupuncture on heart rate variability in coronary heart disease patients", Zhongquo Zhong Xi Yi Jie He Za Zhi 15(9): 536-8. Abstract (1995).

Chiu, YJ et al., "Cardiovascular and endocrine effects of acupuncture in hypotensive patients", *Clin. Exp. Hyperten 19*(7), 1047-1063 (1997).

Yuanhua, W et al., "Effect of acupuncture at quchi and taichong on ET and ACE in the blood of patients with hypertension and exploration of its efficacy", *Chinese Journal of Integrated Chinese and Western Medicine 24*: 1080-83 (2004).

Hongxing, Z et al., "Control observation on acupuncture of Quchi (LI 11) and medication in transient action of decreasing blood pressure", *Chinese Acupuncture and Moxibustion*. 2001: 11. Abstract (2011).

Swartz, KL "The John Hopkins White Papers: Depression and Anxiety", 2011.

Wheeler, Mark "Non-Invasive Therapy Significantly Improves Depression, Researchers Say", ScienceDaily.com (Sep. 6, 2010). Orig. published by UCLANews.

Lewis, D. "Trigeminal Nerve Stimulation for Depression", www.helpforDepression.com (Sep. 15, 2011).

"Trigeminal Nerve Stimulation Significantly Improves Depression", www.psypost.org, Friday, Sep. 3, 2010.

Liu, Q et al., "Beneficial Effect of Acupuncture on Depression", *Acupuncture Therapy for Neurological Diseases*. Springer. 2010; 437-39.

Han, C et al., "Clinical Study on Electroacupuncture Treatment for 30 Cases of Mental Depression", *Journal of Traditional Chinese Medicine*. 2004. 24(3): 172-6.

Meng, F et al., "Plasma NE Concentrations and 24 Hours Urinary MHPG S04 Excretion Changes After Electro-Acupuncture Treatment in Endogenous Depression", *World J. Acup-Mox. 1994*; 4:45-52.

Jin, GL et al., "The effect of electro-acupuncture on chronic stress-induced depression rat brain's monoamine neurotransmitters", *Chin J Psychiatry*. 1999; 32: 220-222.

Han, C et al., "Randomized clinical trial comparing the effects of electro-acupuncture and maprotiline in treating depression", *Int. J Clin Acupoint*. 2006; 15(1): 7-14.

(56) References Cited

OTHER PUBLICATIONS

Luo, H. et al., "Preliminary research on treatment of common mental disorders with computer controlled electroacupuncture", *Chinese Journal of Integrated Medicine 1996*; 2(2): 98-100.
Non-Final Office Action received in U.S. Appl. No. 13/796,314 dated Aug. 17, 2015.
Cheung, et al., "The Mechanism of Acupuncture Therapy and Clinical Case Studies", Taylor & Francis, publisher. (2001) ISBN 0-415-27254-8. *The Forward*, Chapters 1-3, 5, 7, 8, 12, & 13.
Degiorgio, C. et al., "Trigeminal Nerve Stimulation: Seminal Animal and Human Studies for Epilepsy and Depression", *Neurosurg Clin N Am 22* (2011) 449-456.
Han, C. et al., "Comparative study of electro-acupuncture and maprotiline in treating depression", Zhonmuo Zhong Xi Yi Jie He Za Zhi. 2002; 22(7): 512-514. Chinese with English Abstract.

\* cited by examiner

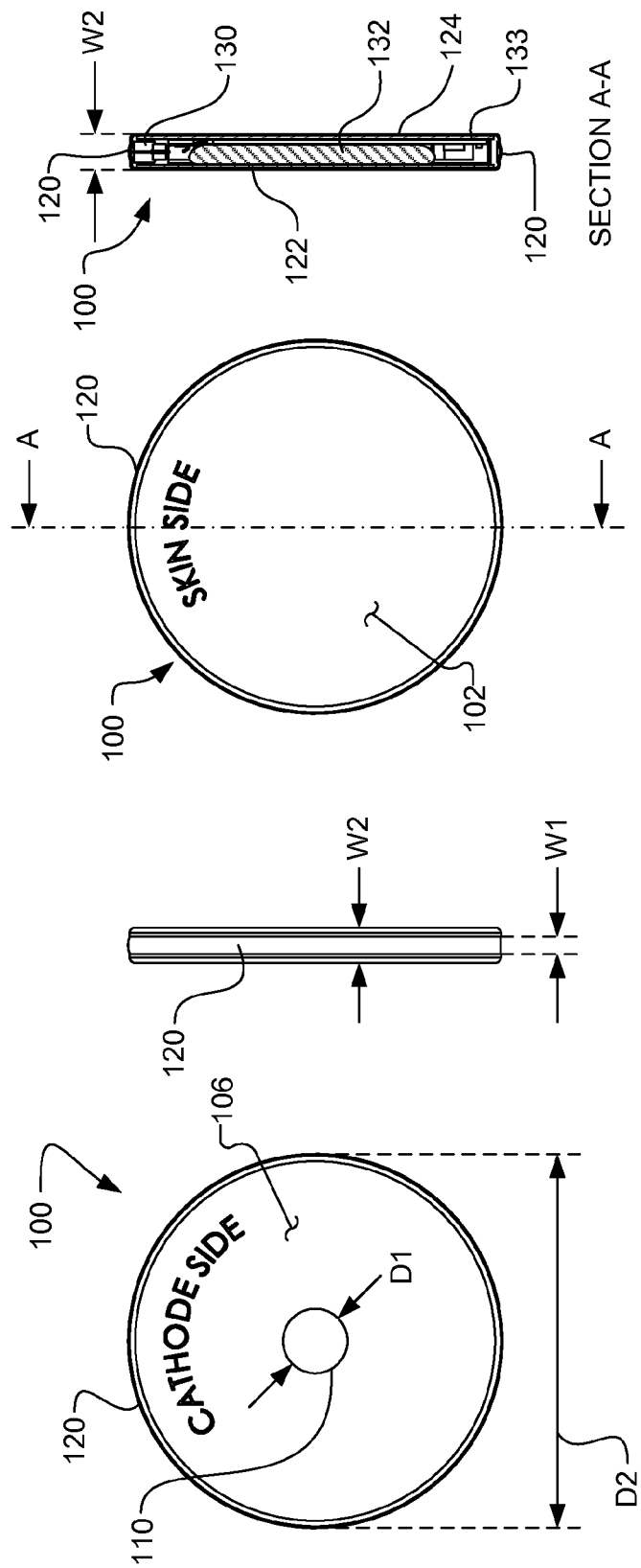

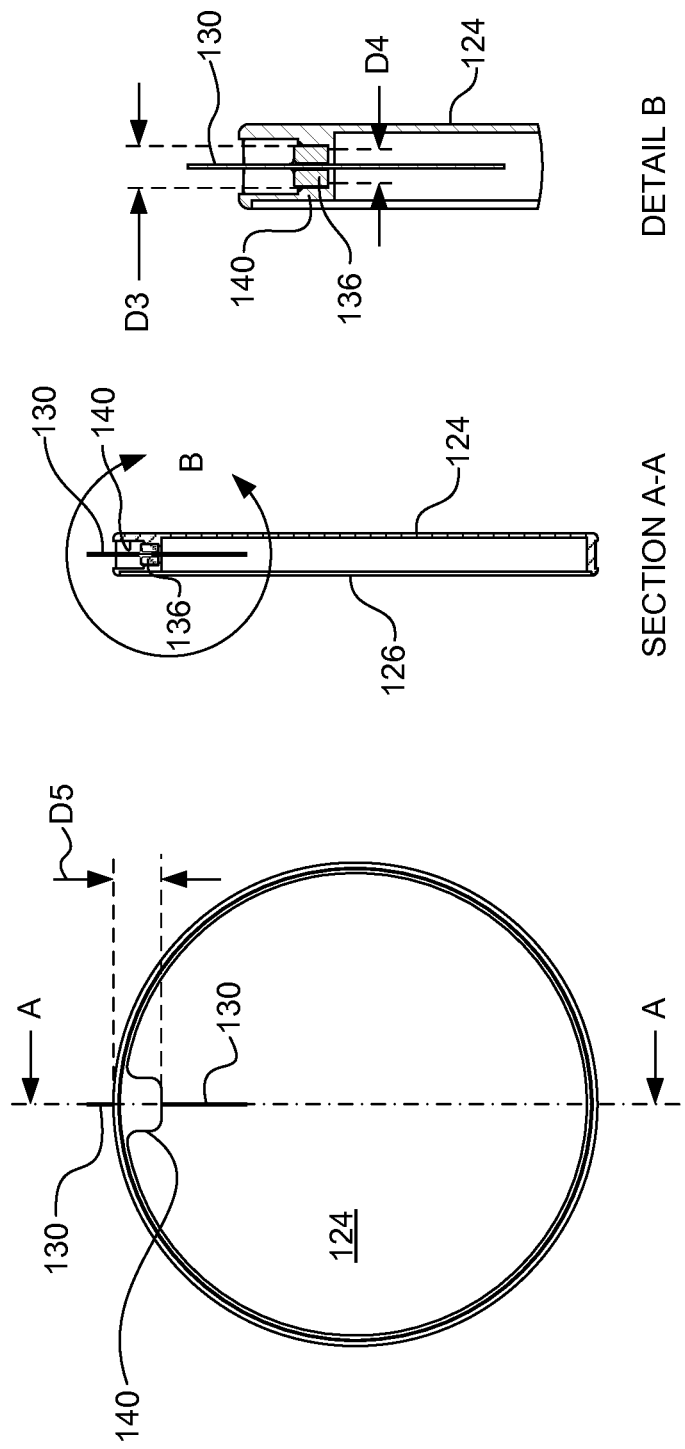

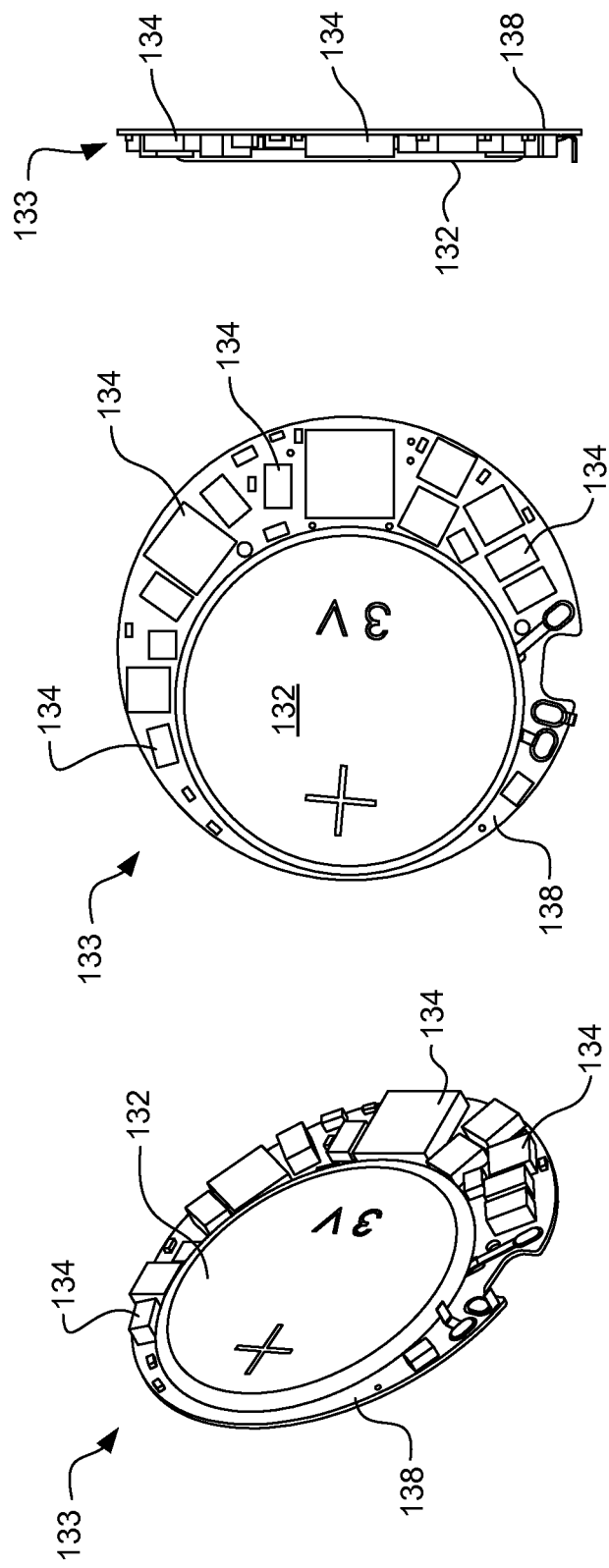

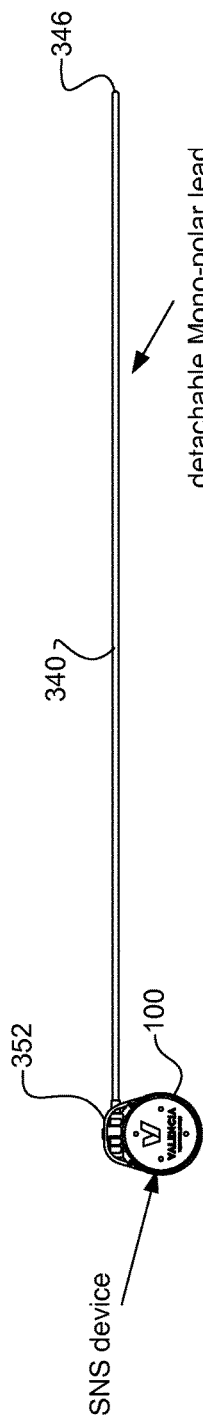
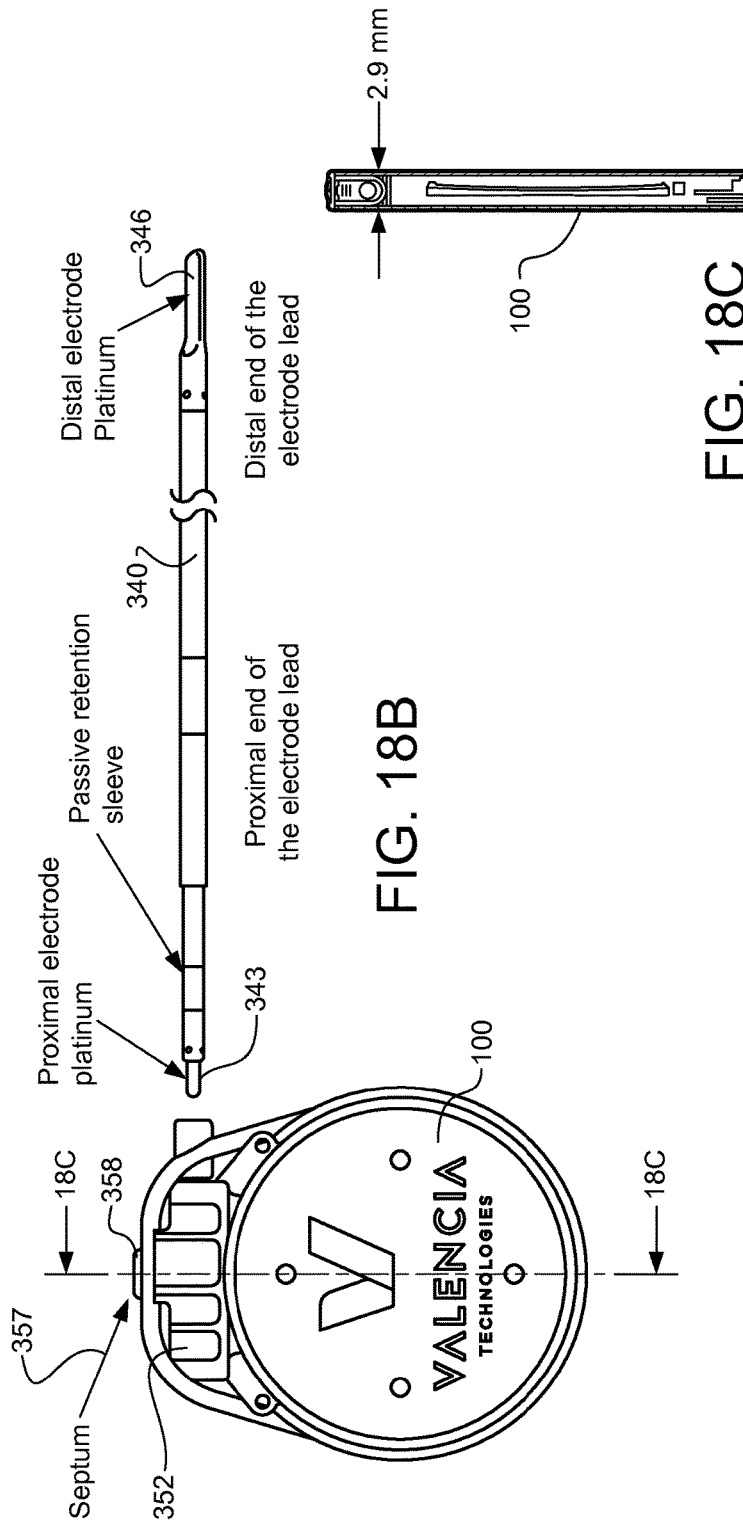
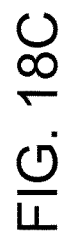
FIG. 18A
FIG. 18B
FIG. 18C

Silicone insulation and lumen seals over molded on Titanium header

Titanium header bracket With Bal seal and connector block

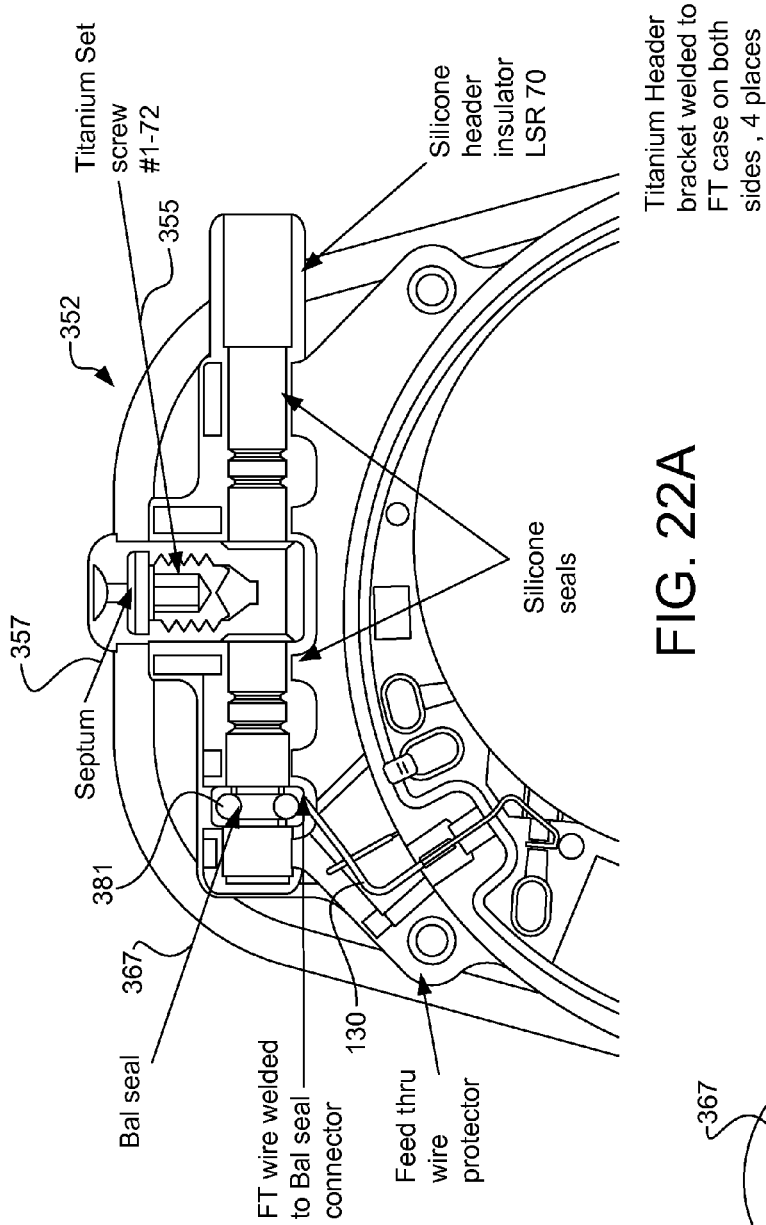
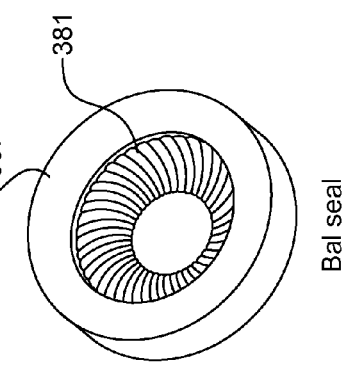
FIG. 22A
FIG. 22C ions in their respective entireties.

METHODS AND SYSTEMS FOR TREATING A CHRONIC LOW BACK PAIN CONDITION USING AN IMPLANTABLE ELECTROACUPUNCTURE DEVICE

RELATED APPLICATIONS

The present application is a continuation-in-part application of U.S. application Ser. No. 13/796,314(now U.S. Pat. No. 9,327,134), filed Mar. 12, 2013, and claims priority under 35 U.S.C. §119(e) to U.S. Provisional Patent Application No. 62/030,589, filed Jul. 29, 2014, and U.S. Provisional Patent Application No. 62/091,333, filed Dec. 12, 2014. U.S. application Ser. No. 13/796,314 is a continuation-in-part application of U.S. application Ser. No. 13/598,582(now U.S. Pat. No. 8,965,511), filed Aug. 29, 2012; U.S. patent application Ser. No. 13/622,653(now U.S. Pat. No. 8,996,125), filed Sep. 19, 2012; and U.S. patent application Ser. No. 13/630,522(now U.S. Pat. No. 9,173,811), filed Sep. 28, 2012. U.S. application Ser. No. 13/796,314 also claims priority under 35 U.S.C. §119(e) to U.S. Provisional Patent Application No. 61/609,875, filed Mar. 12, 2012; U.S. Provisional Patent Application No. 61/672,257, filed Jul. 16, 2012; U.S. Provisional Patent Application No. 61/672,661, filed Jul. 17, 2012; U.S. Provisional Patent Application No. 61/673,254, filed Jul. 19, 2012; U.S. Provisional Patent Application No. 61/674,691, filed Jul. 23, 2012; and U.S. Provisional Patent Application No. 61/676,275, filed Jul. 26, 2012. All of these applications are incorporated herein by reference in their respective entireties.

BACKGROUND INFORMATION

Low back pain is a major health problem that causes high medical expenses, absenteeism in the workplace and disablement. Low back pain is characterized as chronic when it persists for at least three months; otherwise, it is called "acute."

There are three patterns of back pain: axial, referred, and radicular. Axial pain is that localized to the back, which usually gets better with pain medication and physical therapy. Referred pain is an achy, dull pain that extends from the back to the extremities along the nerve path. Referred pain may come and go, move around in location, and vary in intensity. Radicular pain is a deep, steady pain that radiates from the back to the extremities and is associated with certain activities like standing, walking, or sitting. Sciatica is an example of the most common version of radicular pain.

Four out of five adults experience significant low back pain at some point in their lives. The major causes of back pain in adults are: sprains, strains, and spasms; degenerative changes of the spinal bones and disks; herniated disks; vertebral compression fractures; spinal stenosis; and spinal deformities. Additionally, sciatica and cauda equina syndrome are two conditions caused by spinal stenosis or disk herniation.

An alternative approach for treating chronic low back pain, diabetes, high cholesterol and a host of other physiological conditions, illnesses, deficiencies and disorders is acupuncture, which includes traditional acupuncture and acupressure. Acupuncture has been practiced in Eastern civilizations (principally in China, but also in other Asian countries) for at least 2500 years. It is still practiced today throughout many parts of the world, including the United States and Europe. A good summary of the history of acupuncture, and its potential applications may be found in Cheung, et al., "*The Mechanism of Acupuncture Therapy and Clinical Case Studies*", (Taylor & Francis, publisher) 2001) ISBN 0-415-27254-8, hereafter referred to as "Cheung, *Mechanism of Acupuncture*, 2001." The Forward, as well as Chapters 1-3, 5, 7, 8, 12 and 13 of Cheung, *Mechanism of Acupuncture*, 2001, are incorporated herein by reference.

Despite the practice in Eastern countries for over 2500 years, it was not until President Richard Nixon visited China (in 1972) that acupuncture began to be accepted in the West, such as the United States and Europe. One of the reporters who accompanied Nixon during his visit to China, James Reston, from the *New York Times*, received acupuncture in China for post-operative pain after undergoing an emergency appendectomy under standard anesthesia. Reston experienced pain relief from the acupuncture and wrote about it in *The New York Times*. In 1973 the American Internal Revenue Service allowed acupuncture to be deducted as a medical expense. Following Nixon's visit to China, and as immigrants began flowing from China to Western countries, the demand for acupuncture increased steadily. Today, acupuncture therapy is viewed by many as a viable alternative form of medical treatment, alongside Western therapies. Moreover, acupuncture treatment is now covered, at least in part, by most insurance carriers. Further, payment for acupuncture services consumes a not insignificant portion of healthcare expenditures in the U.S. and Europe. See, generally, Cheung, *Mechanism of Acupuncture*, 2001, vii.

Acupuncture is an alternative medicine that treats patients by insertion and manipulation of needles in the body at selected points. See, Novak, Patricia D. et al (1995). Dorland's Pocket Medical Dictionary (25th ed.), Philadelphia: (W.B. Saunders Publisher), ISBN 0-7216-5738-9. The locations where the acupuncture needles are inserted are referred to herein as "acupuncture points" or simply just "acupoints". The location of acupoints in the human body has been developed over thousands of years of acupuncture practice, and maps showing the location of acupoints in the human body are readily available in acupuncture books or online. For example, see, "Acupuncture Points Map," found online at: http://www.acupuncturehealing.org/acupuncture-points-map.html. Acupoints are typically identified by various letter/number combinations, e.g., L6, S37. The maps that show the location of the acupoints may also identify what condition, illness or deficiency the particular acupoint affects when manipulation of needles inserted at the acupoint is undertaken.

References to the acupoints in the literature are not always consistent with respect to the format of the letter/number combination. Some acupoints are identified by a name only, e.g., Shenshu. The same acupoint may be identified by others by the name followed with a letter/number combination placed in parenthesis, e.g., Shenshu (BL23). Alternatively, the acupoint may be identified by its letter/number combination followed by its name, e.g., BL23 (Shenshu). The first letter typically refers to a body organ, or meridian, or other tissue location associated with, or affected by, that acupoint. However, usually only the letter is used in referring to the acupoint, but not always. Thus, for example, the acupoint BL23 is the same as acupoint Bladder 23 which is the same as BL-23 which is the same as BL 23 which is the same as Shenshu. For purposes of this patent application, unless specifically stated otherwise, all references to acupoints that use the same name, or the same first letter and the same number, and regardless of slight differences in second letters and formatting, are intended to refer to the same acupoint.

An excellent reference book that identifies all of the traditional acupoints within the human body is *WHO STANDARD ACUPUNCTURE POINT LOCATIONS IN THE WESTERN PACIFIC REGION*, published by the World Health Organization (WHO), Western Pacific Region, 2008 (updated and reprinted 2009), ISBN 978 92 9061 248 7 (hereafter "*WHO Standard Acupuncture Point Locations* 2008"). The Table of Contents, Forward (page v-vi) and General Guidelines for Acupuncture Point Locations (pages 1-21), as well as pages 110-112 (which illustrate with particularity the location of acupoints BL22, BL23, BL24, BL25, BL26) of the *WHO Standard Acupuncture Point Locations* 2008 are incorporated herein by reference. The relevant information from pages 110-112 of the *WHO Standard Acupuncture Point Locations* 2008 book is also presented herein as FIG. 1A, and accompanying text.

It should be noted that other medical research, not associated with acupuncture research, has over the years identified nerves and other locations throughout a patient's body where the application of electrical stimulation produces a beneficial effect for the patient. Indeed, the entire field of neurostimulation deals with identifying locations in the body where electrical stimulation can be applied in order to provide a therapeutic effect for a patient. For purposes of this patent application, such known locations within the body are treated essentially the same as acupoints—they provide a "target" location where electrical stimulation may be applied to achieve a beneficial result, whether that beneficial result is to treat back pain, reduce cholesterol or triglyceride levels, to treat cardiovascular disease, to treat mental illness, or to address some other issue associated with a disease or condition of the patient.

Some have proposed applying moderate electrical stimulation at selected acupuncture points through needles that have been inserted at those points. See, e.g., http://en.wikipedia.org/wiki/Electroacupuncture. Such electrical stimulation is known as electroacupuncture (EA). According to *Acupuncture Today*, a trade journal for acupuncturists: "Electroacupuncture is quite similar to traditional acupuncture in that the same points are stimulated during treatment. As with traditional acupuncture, needles are inserted on specific points along the body. The needles are then attached to an external device that generates continuous electric pulses using small clips. These devices are used to adjust the frequency and intensity of the impulse being delivered, depending on the condition being treated. Electroacupuncture uses two needles at a time so that the impulses can pass from one needle to the other. Several pairs of needles can be stimulated simultaneously, usually for no more than 30 minutes at a time." "Acupuncture Today: Electroacupuncture". 2004 Feb. 1 (retrieved on-line 2006 Aug. 9 at http://www.acupuncturetoday.com/abc/electroacupuncture.php).

U.S. Pat. No. 7,203,548, issued to Whitehurst et al., discloses use of an implantable miniature neurostimulator, referred to as a "microstimulator," that can be implanted into a desired tissue location and used as a therapy for cavernous nerve stimulation. The microstimulator has a tubular shape, with electrodes at each end.

Other patents of Whitehurst et al. teach the use of this small, microstimulator, placed in other body tissue locations, including within an opening extending through the skull into the brain, for the treatment of a wide variety of conditions, disorders and diseases. See, e.g., U.S. Pat. No. 6,950,707 (obesity and eating disorders); U.S. Pat. No. 7,003,352 (epilepsy by brain stimulation); U.S. Pat. No. 7,013,177 (pain by brain stimulation); U.S. Pat. No. 7,155,279 (movement disorders through stimulation of Vagas nerve with both electrical stimulation and drugs); U.S. Pat. No. 7,292,890 (Vagas nerve stimulation); U.S. Pat. No. 6,735,745 (headache and/or facial pain); U.S. Pat. No. 7,440,806 (diabetes by brain stimulation); U.S. Pat. No. 7,610,100 (osteoarthritis); and U.S. Pat. No. 7,657,316 (headache by stimulating motor cortex of brain). The microstimulator patents of Whitehurst et. al., or other similar patents, either require electronics and battery in a coil on the outside of the body or a coil on the outside that enables the recharging of a rechargeable battery. The use of an outside coil, complex electronics, and the tubular shape of the microstimulator have all limited the commercial feasibility of the microstimulator device and applications described in the Whitehurst patents.

Techniques for using electrical devices, including external EA devices, for stimulating peripheral nerves and other body locations for treatment of various maladies are known in the art. See, e.g., U.S. Pat. Nos. 4,535,784; 4,566,064; 5,195,517; 5,250,068; 5,251,637; 5,891,181; 6,006,134; 6,393,324; 6,516,227; 7,171,266; 7,171,266; and 7801,615. See also U.S. Patent Publications Nos. US 2009/0292341 A1; US 2005/0234533 A1; and US 2005/0107832 A1; US 2003/0158588 A1; US 2007/0255319 A1. The methods and devices disclosed in these patents and publications, however, typically utilize (i) relatively large implantable stimulators having long leads that must be tunneled through tissue over an extended distance to reach the desired stimulation site, (ii) external devices that must interface with implanted electrodes via percutaneous leads or wires passing through the skin, (iii) inefficient and power-consuming wireless transmission schemes, and/or (iv) implantable devices that require a rechargeable battery or other power source. Such devices and methods are still far too invasive, or are ineffective, and thus are subject to the same limitations and concerns, as are the previously described electrical stimulation devices.

From the above, it is seen that there is a need in the art for a less invasive device and technique for electroacupuncture stimulation of acupoints that does not require the continual use of needles inserted through the skin, or long insulated wires implanted or inserted into blood vessels, for the purpose of treating chronic low back pain.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

FIG. 2 shows a plan view of one surface of the IEAD housing illustrated in FIG. 1.

FIG. 2A shows a side view of the IEAD housing illustrated in FIG. 1.

FIG. 3 shows a plan view of the other side, indicated as the "Back Side," of the IEAD housing or case illustrated in FIG. 1.

FIG. 3A is a sectional view of the IEAD of FIG. 3 taken along the line A-A of FIG. 3.

FIG. 5 is a plan view of the empty IEAD housing shown in FIG. 4.

FIG. 5A depicts a sectional view of the IEAD housing of FIG. 5 taken along the section line A-A of FIG. 5.

FIG. 5B shows an enlarged view or detail of the portion of FIG. 5A that is encircled with the line B.

FIG. 6 is a perspective view of an electronic assembly, including a battery, adapted to fit inside of the empty housing of FIG. 4 and FIG. 5.

FIGS. 6A and 6B show a plan view and side view, respectively, of the electronic assembly shown in FIG. 6.

FIG. 18A shows an exemplary embodiment of an IEAD that has a detachable lead attached to a header assembly mounted on a perimeter edge of the IEAD.

FIG. 18B shows the embodiment shown in FIG. 18A, but with the lead being detached from the header assembly.

FIG. 18C shows a sectional side view taken along the line 18C-18C of the IEAD shown in FIG. 18B.

FIGS. 20A, 20B and 20C show a sequence of views associated with mounting the header assembly to the perimeter edge of the case of the IEAD; wherein FIG. 20A depicts the header assembly prior to mounting, FIG. 20B illustrates the location on the perimeter edge of the IEAD case where the header assembly is mounted relative to the location of the radial feed-through pin, and FIG. 20C shows the header assembly after being mounted on the perimeter edge.

FIGS. 22A and 22B respectively illustrate sectional views of the header assembly mounted on the edge of the assembled IEAD when the proximal end of the detachable lead is not inserted into the header assembly (FIG. 22A) and when proximal end of the detachable lead is inserted into the header assembly (FIG. 22B).

FIG. 22C shows a perspective view of a Bal Seal used within the header assembly.

Figure 1:
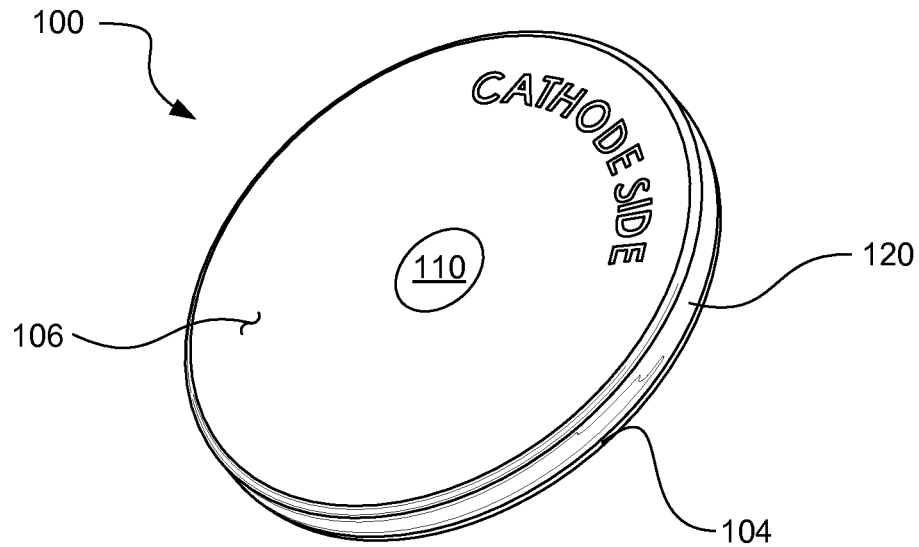
FIG. 1 is a perspective view of a leadless implantable electroacupuncture device (referred to herein as an "IEAD" and as an "EA device") made in accordance with the teachings presented herein.

In addition to the teachings provided by the above drawings, and their accompanying text, additional examples of alternative symmetrical electrode configurations, non-symmetrical electrode configurations, and representative code that may be used in the micro-controller IC (e.g., U2 in FIG. 14) to control the basic operation and programming of the IEAD, may be found in Applicant's earlier application, application Ser. No. 13/598,582, filed Aug. 29, 2012 and issued as U.S. Pat. No. 8,965,511, and/or its appendices, which application and its appendices are incorporated herein by reference.

DETAILED DESCRIPTION

Systems and methods for treating low back pain are described herein. In some examples, the systems and methods may provide an implantable electroacupuncture device (IEAD) that treats chronic low back pain through application of electroacupuncture (EA) stimulation pulses applied at a target tissue location. The target tissue location comprises tissue underlying, or in the vicinity of, at least one of acupoints GV4, BL22, BL23, BL24, BL25, and BL26, all of which are located in the lumbar region about 1.5 inches lateral to the posterior median line. The IEAD may include: (1) a small IEAD housing having a header formed thereon into which a unipolar lead having a distal electrode located at or near its distal tip (hereafter "distal electrode"), may be detachably connected, and at least one other electrode formed as part of the IEAD housing (hereafter "case electrode"), (2) pulse generation circuitry located within the IEAD housing that delivers EA stimulation pulses to the patient's body tissue at at least one of acupoints GV4, BL22, BL23, BL24, BL25, and BL26 through the distal and case electrodes, (3) a primary battery also located within the IEAD housing that provides the operating power for the IEAD to perform its intended function, and (4) a sensor located within the IEAD housing that is responsive to operating commands wirelessly communicated to the IEAD from a non-implanted location. These operating commands allow limited external control of the IEAD, such as ON/OFF and EA stimulation pulse amplitude and/or frequency adjustment.

In some examples, the IEAD housing is made from two main parts: (1) a coin-sized and -shaped housing having a nominal diameter of about 25 mm, and a thickness of only 2 to 3 mm, originally made as a leadless device, having a case electrode and a ring electrode around the perimeter of the coin-sized and shaped housing; and (2) a header assembly that replaces the ring electrode and is attached to one segment of the perimeter of the coin-sized and shaped housing, and including a female connector formed within the header assembly adapted to receive a proximal end of the lead on which the distal electrode is found, this female connecter being electrically connected to a radial feed-through pin originally connected to the ring electrode, but which ring electrode is not utilized in this leaded embodiment of the systems and methods described herein.

In some examples, a relatively short, flexible, smooth, unipolar catheter lead may be attached at its proximal end to the central electrode located on the first surface of the IEAD housing. A suitable insulator then covers the central electrode, including the area where the proximal end of the catheter lead is attached, e.g., welded, to the central electrode surface, so that the only electrical connection that can be made with the central electrode from a location external to the IEAD housing is from a distal end of the catheter lead. The distal end of the catheter lead thus functions as the central electrode. The distal end of the catheter lead is then positioned near the lumbar nerve or dorsal root ganglion of at least one of acupoints GV4, BL22, BL23, BL24, BL25 and BL26. Using such a catheter lead attached to the central electrode allows the IEAD to still be implanted near the specified target acupoint(s), yet further facilities a more efficient and direct stimulation of the lumbar nerve(s) and or dorsal root ganglion(s) in a body tissue location (near the vertebra) where it is difficult to implant the IEAD housing.

Alternatively, the short, smooth, unipolar catheter lead may have its proximal end attached to the annular ring electrode located around the perimeter of the IEAD housing. When this is done, the polarity of the annular ring electrode may be selected to have it function as a cathode. An advantage of having the short lead attached to the edge of the IEAD housing is that the attachment process can be done with strain relief, and thereby provide a more reliable attachment and manufacturing process.

In some examples, the polarity of the original coin-sized and -shaped housing may be reversed, with the anode electrode being the case electrode and with the distal electrode being a cathode electrode. The cathode electrode, located at the distal end of a catheter lead that may be up to 50 mm long (or, in some instances, even longer), is detachably connected to the IEAD radial feed through pin by inserting the proximal end of the catheter lead into the connector in the header assembly. Using a detachable lead in this manner simplifies the implantation process so that the surgeon can carefully insert the distal tip electrode into a desired target simulation point, typically directly adjacent the vertebrae in the lower lumbar region, and then detachably connect the proximal end of the positioned lead to the IEAD case, and placing the case in a suitable implant pocket some distance, e.g, up to 50 mm distance, away from the target tissue locationi.

The pulse generation circuitry located within the IEAD housing is coupled to the at least two electrodes, e.g., the case electrode and the distal electrode. This pulse generation circuitry is configured to generate EA stimulation pulses in accordance with a specified stimulation regimen. This stimulation regimen defines the duration and rate at which a stimulation session is applied to the patient. The stimulation regimen requires that the stimulation session have a duration of no more than T3 minutes and a rate of occurrence of no more than once every T4 minutes.

Advantageously, the duty cycle of the stimulation sessions, i.e., the ratio of T3/T4, is very low, no greater than 0.05. A representative value for T3 is 30 minutes, and a representative value for T4 is 7 days. The individual EA stimulation pulses that occur within the stimulation session also have a duty cycle measured relative to the period (where the "period" is the time interval equal to the inverse of the frequency or rate of the stimulation pulses) of no greater than 3%. A representative pulse width and frequency for the EA stimulation pulses is 0.1 milliseconds, occurring at a pulse rate of 2 Hz. In some instances, the pulse rate may be toggled between a low pulse rate, e.g., 1 to 15 Hz, and a higher pulse rate, e.g., 15 to 100 Hz. In such instance—when toggling between a low and a high stimulation pulse rate—the toggling rate may be set to occur every 3 to 6 seconds.

The primary battery contained within the IEAD housing and electrically coupled to the pulse generation circuitry has a nominal output voltage of 3 volts, and an internal battery impedance that is at least 5 ohms, and may be as high as 150 ohms or more. Advantageously, electronic circuitry within the IEAD housing controls the value of the instantaneous surge current that may be drawn from the battery in order to prevent any large drops in the battery output voltage. Avoiding large drops in the battery output voltage assures that the circuits within the IEAD will continue to operate as designed without failure. Being able to use a primary battery that has a relatively high internal impedance allows the battery to be thinner, and thus allows the device to be thinner and more easily implanted. The higher internal impedance also opens the door to using relatively inexpensive commercially-available disc batteries as the primary battery within the IEAD, thereby greatly enhancing the manufacturability of the IEAD and significantly lowering its cost.

In some examples, a first method for treating chronic low back pain in a patient uses a leaded, coin-sized implantable electroacupuncture device (IEAD). Such IEAD is powered by a small disc battery having a specified nominal output voltage of about 3.0 volts, and having an internal impedance of at least 5 ohms.

The IEAD used to practice this first method is configured, using electronic circuitry within the IEAD, to generate EA stimulation pulses in accordance with a specified stimulation regimen. The EA stimulation pulses generated in accordance with this stimulation regimen are applied to the patient's tissue through the case electrode and through the distal electrode located at the end of the detachable lead, which detachable lead is connected to the IEAD circuitry through the header assembly.

Using such an IEAD, the method for treating chronic low back pain provided by this first method includes the steps of: (a) implanting the distal electrode, of a short unipolar implantable lead, below the skin surface of the patient at or near a selected target tissue location, where the target tissue location comprises tissue underlying, or in the vicinity of, at least one of acupoints GV4, BL22, BL23, BL24, BL25 and BL26; (b) detachably connecting a proximal end of the implantable lead to the header assembly of the IEAD; (c) implanting the IEAD, with the lead attached, in body tissue that is near, e.g., within 50 mm, of the target tissue location; and (d) enabling the IEAD to provide stimulation pulses in accordance with a specified stimulation regimen.

The specified stimulation regimen, when enabled, provides a stimulation session at a rate of one stimulation session every T4 minutes, with each stimulation session having a duration of T3 minutes. The ratio of T3/T4 must be no greater than 0.05. An exemplary stimulation session time T3 is 30 minutes, but T3 could be as short as 10 minutes or as long as 60 minutes. An exemplary time between stimulation sessions, T4, is 7 days, but it could be as short as 1 day or as long as 14 days, as needed, to suit the needs of a particular patient.

In some embodiments, the time period between stimulation sessions, T4, may itself be a variable that increases from an initial value, T4 (min), to a final value, T4 (final), where T4 (min) is a desired initial value, e.g., 1 day (1440 minutes), and T4 (final) is a desired final value, e.g., 7 days (10,080 minutes). In such situation, i.e., where T4 initially varies, the change of T4 between T4 (min) to T4 (final) follows a prescribed ramp-up sequence, e.g., starting at T4 (min), T4 doubles after each stimulation session until the desired value of T4 (final) is reached. Thus, for example, if T4 (min) is 1 day, and T4 (final) is 7 days, the value of T4 may vary as follows once the stimulation sessions begin: T4=1 day, 2 days, 4 days and 7 days.

Overview

Disclosed herein is an implantable, self-contained, leadless electroacupuncture (EA) device having at least two electrode contacts mounted on the surface of its housing. The EA device disclosed herein is adapted to treat chronic low back pain in a patient. In one embodiment, the electrodes on the surface of the EA device include a central cathode electrode on a bottom side of the housing, and an annular anode electrode that surrounds the cathode. In another embodiment, the anode annular electrode is a ring electrode placed around the perimeter edge of the coin-shaped housing.

The EA device can be leadless. This means there are no leads or electrodes at the distal end of leads (common with most implantable electrical stimulators) that have to be positioned and anchored at a desired stimulation site. Also, because there are no leads, no tunneling through body tissue or blood vessels is required in order to provide a path for the leads to return and be connected to a tissue stimulator (also common with most electrical stimulators).

Alternatively, in order to improve the ability of the IEAD to direct the stimulation precisely to a desired target stimulation site, e.g., between specified lumbar vertebra, the EA device may stimulate using a distal electrode at the end of a relatively short, e.g., 50 mm long, monopolar lead attached to the IEAD and a reference, or return, electrode formed on the case of the IEAD. Such monopolar lead may be permanently attached to the IEAD, or detachably connected to the IEAD. If detachably connected, the connection may be made directly at a header assembly mounted onto a perimeter edge of the IEAD, or at a distal connector of a short pigtail lead that has its proximal end permanently attached to the IEAD.

The EA device is adapted to be implanted through a very small incision, e.g., less than 2-3 cm in length, directly adjacent to a selected target stimulation site, e.g., an acupuncture site ("acupoint") known to affect a chronic low back pain condition of a patient.

The EA device is self-contained. It includes a primary battery to provide its operating power. It includes all of the circuitry it needs, in addition to the battery, to allow it to perform its intended function for several years. Once implanted, the patient will not even know it is there, except for a slight tingling that may be felt when the device is delivering stimulus pulses during a stimulation session. Also, once implanted, the patient can just forget about it. There are no complicated user instructions that must be followed. Just turn it on. No maintenance is needed. Moreover, should the patient want to disable the EA device, i.e., turn it OFF, or change stimulus intensity, he or she can do so using, e.g., an external magnet.

The EA device can operate for several years because it is designed to be very efficient. Stimulation pulses applied by the EA device at a selected target stimulation site, e.g., a specified acupoint, through its electrodes formed on its case are applied at a very low duty cycle in accordance with a specified stimulation regimen. The stimulation regimen applies EA stimulation during a stimulation session that lasts at least 10 minutes, typically 30 minutes, and rarely longer than 60 minutes. These stimulation sessions, however, occur at a very low duty cycle. In one exemplary treatment regimen, for example, a stimulation session having a duration of 30 minutes is applied to the patient just once a week. The stimulation regimen, and the selected acupoint at which the stimulation is applied, are designed and selected to provide efficient and effective EA stimulation for the treatment of the patient's chronic low back pain.

The EA device is, compared to most implantable medical devices, relatively easy to manufacture and uses few components. This not only enhances the reliability of the device, but keeps the manufacturing costs low, which in turn allows the device to be more affordable to the patient. One exemplary feature included in the mechanical design of the EA device is the use of a radial feed-through assembly to connect the electrical circuitry inside of its housing to one of the electrodes on the outside of the housing. The design of this radial feed-through pin assembly greatly simplifies the manufacturing process. The process places the temperature sensitive hermetic bonds used in the assembly—the bond between a pin and an insulator and the bond between the insulator and the case wall—away from the perimeter of the housing as the housing is hermetically sealed at the perimeter with a high temperature laser welding process, thus preserving the integrity of the hermetic bonds that are part of the feed-through assembly.

In operation, the EA device is safe to use. There are no horrific failure modes that could occur. Because it operates at a very low duty cycle (i.e., it is OFF much, much more than it is ON), it generates little heat. Even when ON, the amount of heat it generates is not much, less than 1 mW, and is readily dissipated. Should a component or circuit inside of the EA device fail, the device will simply stop working. If needed, the EA device can then be easily explanted.

Another exemplary feature included in the design of the EA device is the use of a commercially-available battery as its primary power source. Small, thin, disc-shaped batteries, also known as "coin cells," are quite common and readily available for use with most modern electronic devices. Such batteries come in many sizes, and use various configurations and materials. However, insofar as the inventors or Applicant are aware, such batteries have never been used in implantable medical devices previously. This is because their internal impedance is, or has always thought to have been, much too high for such batteries to be of practical use within an implantable medical device where power consumption must be carefully monitored and managed so that the device's battery will last as long as possible, and so that dips in the battery output voltage (caused by any sudden surge in instantaneous battery current) do not occur that could compromise the performance of the device. Furthermore, the energy requirements of other active implantable therapies are far greater than can be provided by such coin cells without frequent replacement.

The EA device disclosed herein advantageously employs power-monitoring and power-managing circuits that prevent any sudden surges in battery instantaneous current, or the resulting drops in battery output voltage, from ever occurring, thereby allowing a whole family of commercially-available, very thin, high-output-impedance, relatively low capacity, small disc batteries (or "coin cells") to be used as the EA device's primary battery without compromising the EA device's performance. As a result, instead of specifying that the EA device's battery must have a high capacity, e.g., greater than 200 mAh, with an internal impedance of, e.g., less than 5 ohms, which would either require a thicker battery and/or preclude the use of commercially-available coin-cell batteries, the EA device of the present systems and methods can readily employ a battery having a relatively low capacity, e.g., less than 60 mAh, and a high battery impedance, e.g., greater than 5 ohms.

Moreover, the power-monitoring, power-managing, as well as the pulse generation, and control circuits used within the EA device are relatively simple in design, and may be readily fashioned from commercially-available integrated circuits (IC's) or application-specific integrated circuits (ASIC's), supplemented with discrete components, as needed. In other words, the electronic circuits employed within the EA device need not be complex nor expensive, but are simple and inexpensive, thereby making it easier to manufacture and to provide it to patients at an affordable cost.

An exemplary application for an EA device made in accordance with the teachings presented herein is to treat chronic low back pain. Thus, the description that follows describes in much more detail an EA device that is especially suited to be used to treat chronic low back pain. However, it is to be understood that the systems and methods described herein are not limited to treating only chronic low back pain.

In at least one embodiment, the EA device has a short lead attached to one of its electrodes, e.g., the cathode electrode. This makes it possible in some situations where chronic low back pain is being treated, to position a unipolar electrode, typically a unipolar cathode electrode, closer to the lumbar nerve and dorsal roots while the housing of the EA device remains subcutaneously positioned at a desired acupoint.

In another embodiment, the short lead attached to the IEAD is detachably connected via a connector included within a header assembly mounted on a peripheral edge of the IEAD.

Definitions

As used herein, "annular", "circumferential", "circumscribing", "surrounding" or similar terms used to describe an electrode or electrode array, or electrodes or electrode arrays, (where the phrase "electrode or electrode array," or "electrodes or electrode arrays," is also referred to herein as "electrode/array," or "electrodes/arrays," respectively) refers to an electrode/array shape or configuration that surrounds or encompasses a point or object, such as another electrode, without limiting the shape of the electrode/array or electrodes/arrays to be circular or round. In other words, an "annular" electrode/array (or a "circumferential" electrode/array, or a "circumscribing" electrode/array, or a "surrounding" electrode/array), as used herein, may be many shapes, such as oval, polygonal, starry, wavy, and the like, including round or circular.

An "implantable electroacupuncture device", or "IEAD", refers to a thin, coin-sized, self-contained, neural stimulator that can be implanted subcutaneously at or near a desired target stimulation site, e.g., a specified acupoint. An IEAD may sometimes be referred to herein as a subcutaneous neural stimulator (SNS) device. An exemplary IEAD or SNS is leadless, but some embodiments may include a short monopolar lead.

"Nominal" or "about" when used with a mechanical dimension, e.g., a nominal diameter of 23 mm, means that there is a tolerance associated with that dimension of no more than plus or minus (+/−) 5%. Thus, a dimension that is nominally 23 mm means a dimension of 23 mm+/−1.15 mm (0.05×23 mm=1.15 mm). "Nominal" when used to specify a battery voltage is the voltage by which the battery is specified and sold. It is the voltage you expect to get from the battery under typical conditions, and it is based on the battery cell's chemistry. Most fresh batteries will produce a voltage slightly more than their nominal voltage. For example, a new nominal 3 volt lithium coin-sized battery will measure more than 3.0 volts, e.g., up to 3.6 volts under the right conditions. Since temperature affects chemical reactions, a fresh warm battery will have a greater maximum voltage than a cold one. For example, as used herein, a "nominal 3 volt" battery voltage is a voltage that may be as high as 3.6 volts when the battery is brand new, but is typically between 2.7 volts and 3.4 volts, depending upon the load applied to the battery (i.e., how much current is being drawn from the battery) when the measurement is made and how long the battery has been in use.

As explained in more detail below, an electroacupunture modulation scheme need not be continuous, thereby allowing the implanted EA device to use a small, high density, power source to provide such non-continuous EA modulation. (Here, it should be noted that "EA modulation," as that phrase is used herein, is the application of electrical stimulation pulses, at low intensities, low frequencies and low duty cycles, to at least one of the target stimulation sites, e.g., an acupuncture site that has been identified as affecting a particular condition, e.g., chronic low back pain, of the patient. As a result, the EA device can be very small. And, because the electrodes form an integral part of the housing of the EA device, the EA device may thus be implanted directly at (or very near to) the desired target tissue location, e.g., the target stimulation site, such as the target acupoint.

In summary, and as explained more fully below in conjunction with the description of the treatment method for treating chronic low back pain, the basic approach of EA stimulation includes: (1) identify an acupoint(s) or other target stimulation site that may be used to treat or mediate the particular illness, condition or deficiency that has manifest itself in the patient, e.g., chronic low back pain; (2) implant an EA device, made as described herein, so that its electrodes are located to be near or on the identified acupoint (s) or other target stimulation site; (3) apply EA modulation, having a low intensity, low frequency, and low duty cycle through the electrode(s) of the EA device so that electrical stimulation pulses flow through the tissue at the target stimulation site following a prescribed stimulation regimen over several weeks or months or years. At any time during this EA stimulation regimen, the patient's illness, condition or deficiency may be evaluated and, as necessary, the parameters of the EA modulation applied during the EA stimulation regimen may be adjusted or "tweaked" in order to improve the results obtained from the EA modulation.

Conditions Treated

Low back pain is a major health problem in western nations causing high medical expenses, absenteeism in the workplace and disablement. Low back pain is characterized as chronic when it persists for at least three months; otherwise, it is called "acute."

The present methods and systems treat patients with chronic low back pain. However, the cause of such pain may vary from patient to patient and it may yet be determined that a certain origin of chronic low back pain is more treatable with the present methods and systems than another. For example, it is known that in a selection of patients with a duration of low back pain of at least 6 weeks and a baseline visual analogue scale of 50 mm, acupuncture applied in the chosen region was successful. See, Molsberger, A. F., Mau, J., Pawelec, D. B., & Winkler, J. (2002). Does acupuncture improve the orthopedic management of chronic low back pain—a randomized, blinded, controlled trial with 3 months fellow up. *Pain*, 99(3), 579-587 (hereafter, "Molsberger 2002").

Additionally, it has been reported in the acupuncture literature that patients with a low back pain origin of intervertebral disk profusion have been treated successfully by applying conventional acupuncture in the lumbar region about 1.5 inches lateral to the posterior median line See, Zhou, X. P., & Huang, C. J. (2010). Influence of acupuncture plus LONG's manual manipulations on functional improvement in lumbar intervertebral disc protrusion. *Journal of Acupuncture and Tuina Science*, 8, 375-379. For a study showing success in patients with relapsed lumbar disk herniation after disc surgery, see, Wu, Y. C., Wang, C. M., Zhang, J. F., & Li, S. S. (2010). Clinical observation on the treatment of relapsed lumbar disc herniation after disc surgery by acupuncture plus medication. *Journal of Acupuncture and Tuina Science*, 8, 315-317.

It has also been shown that acupuncture in the region brought about positive results in patients with pain due to lumbar strain and hyperplastic spondylitis. See, Lian, N., Liu, J. B., Torres, F., Yan, Q. M., & Guerra, E. (2005). Improvement of dermal needle and body acupuncture on pain due to lumbar strain and hyperplastic spondylitis.

Patients with low back pain second to degenerative disk disease have been successfully treated with a similar treatment modality. See, Ghoname, E. A., Craig, W. F., White, P. F., Ahmed, H. E., Hamza, M. A., Henderson, B. N., . . . & Gatchel, R. J. (1999). Percutaneous electrical nerve stimulation for low back pain: a randomized crossover study. *JAMA: the journal of the American Medical Association*, 281(9), 818-823.

It has also been shown that acupuncture applied in the lumbar region has been shown to bring about significant positive benefit in patients with a long history of low back pain (e.g. 10 years on average). See, Molsberger 2002. See also, Yeung, C. K., Leung, M. C., & Chow, D. H. (2003). The use of electro-acupuncture in conjunction with exercise for the treatment of chronic low-back pain. *The Journal of Alternative & Complementary Medicine*, 9(4), 479-490.

Applicant believes the mechanism of action achieved through use of the methods and systems described herein is both central and local in nature. In a study published in 1984, electroacupuncture in the identified region was performed and tests were designed to determine whether a central mechanism of action existed, thus improving both low back pain and experimental pain in the forearms, or whether a local mechanism of action existed, thus only reducing the low back pain. See, Price, D. D., Rafii, A., Watkins, L. R., & Buckingham, B. (1984). A psychophysical analysis of acupuncture analgesia, *Pain*, 19(1), 27-42. It was determined that both mechanisms were present based upon patient response to experimental pain and report of low back pain.

Furthermore, the involvement of opioid receptors and opiate peptides has been put forth as highly relevant to the mechanism. In one study, it was shown that low frequency electroacupuncture that reduced pain in ten patients was also associated with increases in beta endorphin levels found in the cerebrospinal fluid (CSF). It is suggested that the analgesia observed may be mediated by the release into the CSF of the endogenous opiate, beta-endorphin. See, Clement- Jones, V., Tomlin, S., Rees, L., Mcloughlin, L., Besser, G. M., & Wen, H. L. (1980). Increased β-endorphin but not met-enkephalin levels in human cerebrospinal fluid after acupuncture for recurrent pain. *The Lancet*, 316(8201), 946-949.

In another study published in Korean with an English abstract, it was similarly seen that acupuncture produced an analgesic effect and increased beta-endorphin levels in chronic low back pain patients. Additionally, cortisol and ACTH levels changed 60 minutes following acupucnture. See, Song, J. G., Lim, G. S., & Kim, K. S. (1989). Effects of acupuncture on the plasma levels of β endorphine, ACTH and cortisol in chronic low back pain. The Journal of Korean Acupuncture & Moxibustion Society, 6, 63-82.

There is some evidence in humans, other than experimental pain tests, that the mechanism may be partially central in nature. In a study performed by a group frequently cited in this application, electroacupuncture was performed on a region of the back similar to the acupoints described by in this application but for the treatment of neck pain. The electroacupuncture was successful, suggesting that a central mechanism might be involved. See, White 2000.

Furthermore, an important player in acupuncture research on pain, J S Han, has written about the involvement of opioid receptors and their chemicals, namely, dynorphins and enkaphalins. See, Han, J. S. (2011). Acupuncture analgesia: areas of consensus and controversy. *Pain*, 152(3), S41-S48. See also, Sjölund, B., Terenius, L, & Eriksson, M. (1977). Increased Cerebrospinal Fluid Levels of Endorphins after Electro-Acupuncture. *Acta Physiologica Scandinavica*, 100(3), 382-384. In general, the writings of Han suggest that the mechanism of action for reduction of pain by acupuncture likely involves modulation of opioid receptors and their chemicals.

Locations Stimulated and Stimulation Paradigms/Regimens

Acupuncture for low back pain historically utilizes acupoints (sometimes referred to as "points") located throughout the body with particular focus on the back region. As Traditional Chinese Medicine prescribes, the individual is treated as a whole based on the particularity of his symptoms. Thus, traditionally, about a dozen points are utilized in a single acupuncture session.

Applicant, however, was determined to narrow the necessary points. It did so based on identification and analysis of the most commonly utilized points, and a thorough comparison of successful acupuncture studies utilizing a small number of points in order to determine which points were most responsible for the positive effect.

Applicant has identified a handful of points most appropriate as the target location for stimulation, all laying on a single meridian called "bladder" and identified by the two letters, "B-L" or alternatively, called "urinary bladder" and identified by the two letters, "U-B". Points on this meridian are bilateral acupoints, meaning that there are two points for each name or number combination, e.g., BL22 is located on either side of the spine. Applicant identifies the following acupoints located along the bladder meridian in the lumbar region and within close proximity of one another: BL22 ("Sanjiaoshu"), BL23 ("Shenshu"), BL24 ("Qihaishu"), BL25 ("Dachangshu"), and BL26 ("Guanyuanshu"). Each acupoint may have a number of names to identify the point. As a general rule, one or two letters usually signifies the meridian and then a number to identify where the acupoint falls on that meridian.

In one electroacupuncture study for the treatment of low back pain where success was found, the points stimulated are relatively few. See, Yeung, C. K, Leung, M. C., & Chow, D. H. (2003). The use of electro-acupuncture in conjunction with exercise for the treatment of chronic low-back pain. *The Journal of Alternative & Complementary Medicine*, 9(4), 479-490 (hereafter, "Yeung 2003").

Most impressively, however, is the commonality of the acupoints BL23 and BL25 with more than a handful of studies identified by Applicant as sufficiently rigorous, successful, and supportive of its methods and systems.

Those two acupoints are found to be most commonly utilized for the treatment of low back pain. See, Xia, Y., & Wu, G. (Eds.). (2010). *Acupuncture therapy for neurological diseases: a neurobiological view*. Springer (hereafter, "Xia 2010").

For example, a large number of patients, several hundred, with low back pain were treated successfully with just three acupoints on the back including BL23 and BL25. See, Wang J. (1996). The Effect of Acupuncture on 492 Cases of Lumbago. *Shanghai Acupuncture Journal*, 15(5): 28-29 (In Chinese with English translation).

The location of the chosen sites for stimulation, identified by theft acupoints, is next described. "BL22" is located in the lumbar region at the same level as the inferior border of the spinous process of the first lumbar vertebra (L1), about 1.5 inches lateral to the posterior median line.

"BL23" is located in the lumbar region at the same level as the inferior border of the spinous process of the second lumbar vertebra (L2), about 1.5 inches lateral to the posterior median line.

"BL24" is located in the lumbar region at the same level as the inferior border of the spinous process of the third lumbar vertebra (L3), about 1.5 inches lateral to the posterior median line.

"BL25" is located in the lumbar region at the same level as the inferior border of the spinous process of the fourth lumbar vertebra (L4), about 1.5 inches lateral to the posterior median line.

"BL26" is located in the lumbar region at the same level as the inferior border of the spinous process of the fifth lumbar vertebra (L5), about 1.5 inches lateral to the posterior median line.

The electrical paradigm for use as part of the present methods and systems is one allowing for the use of low frequency, alternating low frequencies, alternating low and high frequency, and alternating medium frequencies. For paradigms requiring alternating frequencies, for example, 15/30 Hz, means that stimulation is provided with 15 Hz for approximately three to six seconds and then it is alternated with 30 Hz for approximately three to six seconds. See, Xiao-Hong, C., Su-Fong, G., Chung-Gwo, C., & JI-SHENG, H. (1994). Optimal conditions for eliciting maximal electroacupuncture analgesia with dense-and-disperse mode stimulation. *American journal of acupuncture*, 22(1), 47-53.

The pulse width should be approximately 0.5 ms for the recruitment of desired nerve fibers. The optimal pulse width might vary from approximately 0.2 ms to 0.7 ms as seen in electroacupuncture studies identified by Applicant for treatment of chronic low back pain. See Yeung 2003 (for an example of 0.5 ms pulse width); White, P. F., El-sayed, A. G., Ahmed, H. E., Hamza, M. A., Craig, W. F., & Vakharia, A. S. (2001), The effect of montage on the analgesic response to percutaneous neuromodulation therapy. *Anesthesia & Analgesia*, 92(2), 483-487; Chen X., Han J S. (1992). $2/15$ Hz Electrical Stimulation Induced an Increase of Both Met-enkephalin-Arg-Phe and Dynorphin from Spinal Cord in Humans, Journal of Beijing Medical University, 80 (In Chinese with English translation) (hereafter, "Chen 1992").

Unlike present state neuromodulation technologies, in particular spinal cord stimulation for treatment of pain, the methods and systems described herein use short duration of stimulation. The duration of stimulation should be approximately 30 minutes, but may be between fifteen minutes and one hour, with a rate of occurrence between once and five times weekly. The prescribed duration of stimulation follows a 2000 year history of acupuncture that indicates approximately 30 minute acupuncture sessions one time a week can provide sufficient benefit to a patient. More narrowly, every acupuncture or stimulation study on which Applicant relies for the methods and systems described herein utilize limited durations and a similar rate of occurrence. In fact, it is determined that 30 and 45 minute stimulation sessions for the treatment of low back pain with acupuncture-like stimulation on or near the region Applicant has identified is better than sessions of only 15 minutes of stimulation. See, Hamza, M. A., El-sayed, A, G., White, P. F., Craig, W, F., Ahmed, H. E., Gajraj, N. M., . . . & Noe, C, E. (1999). Effect of the duration of electrical stimulation on the analgesic response in patients with low back pain. *Anesthesiology*, 91(6), 1622 (hereafter, "Hamza 1999").

In one study comparing the response to stimulation at or near our target points utilizing different frequencies, it was determined that an alternating frequency of 15 Hz and 30 Hz was most efficacious (as to the extent of the effect and its long-lasting effect) than 0 Hz, 4 Hz, or 100 Hz. See, Ghoname, E. S., Craig, W. F., White, P. F., Ahmed, H. E., Hamza, M. A., Gajraj, N. M., . . . & Noe, C. E. (1999). The effect of stimulus frequency on the analgesic response to percutaneous electrical nerve stimulation in patients with chronic low back pain, *Anesthesia and analgesia*, 88(4). 841-846 (hereafter, "Ghoname 1999").

In three other studies performed by the same group, similar results utilizing an alternating frequency of 15 Hz and 30 Hz were found. See, White, P. F., Craig, W. F., Vakharia, A. S., El-sayed, A. G., Ahmed, H. E., & Hamza, M. A. (2000). Percutaneous neuromodulation therapy: does the location of electrical stimulation effect the acute analgesic response?. *Anesthesia & Analgesia*, 91(4), 949-954 (hereafter, "White 2000"); Ghoname 1999; White, P. F., El-sayed, A. G., Ahmed, H. E., Hamza, M. A., Craig, W. F., & Vakharia, A. S. (2001). The effect of montage on the analgesic response to percutaneous neuromodulation therapy. *Anesthesia & Analgesia*, 92(2), 483-487 (hereafter, "White 2001"); Hamza 2999.

Applicant believes that alternating frequencies of 2 Hz and 15 Hz will also provide adequate or even optimum clinical benefit. See also, Xao-Hong, C., Su-Fong, G., Chung-Gwo, C., & JI-SHENG, H. (1994). Optimal conditions for eliciting maximal electroacupuncture analgesia with dense-and-disperse mode stimulation. *American journal of acupuncture*, 22(1), 47-53 (hereafter, "Xao-Hong 1994"); Chen 1992; Tsui; M. L, & Cheing, G. L. (2004). The effectiveness of electroacupuncture versus electrical heat acupuncture in the management of chronic low-back pain. *Journal of Alternative & Complementary Medicine*, 10(5), 803-809 (hereafter, "Tsui 2004"); Carlsson, C. P., & Sjölund, B. H. (2001). Acupuncture for chronic low back pain: a randomized placebo-controlled study with long-term follow-up. *The Clinical journal of pain*, 17(4), 296-305 (hereafter, "Carlsson 2002").

There is significant work suggesting that low frequency stimulation of the chosen locations produces improvement in pain condition of chronic low back pain patients. Applicant herein identifies seven studies in which low frequency stimulation is utilized with success. See, Yeung 2003; Xin B, Zhu ZC. (2005). Observation on Therapeutic Effect of Electro-acupuncture in the Treatment of Chronic Low Back Pain: A Report of 30 Cases. *J Acupunct Tuina* (hereafter, "Xin 2005"); Strauss, A. J., & Xue, C. C. (2001). Acupuncture for chronic non-specific low back pain: A case series study. *Chinese Journal of Integrated Traditional and Western Medicine*, 7(3), 190-194 (hereafter, "Strauss 2001"); Wu, Y. C., Wang, C. M., Zhang, J. F., & Li, S. S. (2010). Clinical observation on the treatment of relapsed lumbar disc herniation after disc surgery by acupuncture plus medication. *Journal of Acupuncture and Tuina Science*, 8, 315-317 (hereafter, "Wu 2010"); Tsukayama, H., Yamashita, H., Amagai, H., & Tanno, Y. (2002). Randomised controlled trial comparing the effectiveness of electroacupuncture and TENS for low back pain: a preliminary study for a pragmatic trial. *Acupuncture in Medicine*, 20(4), 175-180 (hereafter, "Tsukayama 2002"); Ghoname, E. A., Craig, W. F., White, P. F., Ahmed, H. E., Hamza, M. A., Henderson, B. N., . . . & Gatchel, R. J. (1999). Percutaneous electrical nerve stimulation for low back pain: a randomized crossover study. *JAMA: the journal of the American Medical Association,* 281(9), 818-823 (*hereafter, "Ghoname* 1999"); and, Sakai, T. O. M. O. M. I., Tsutani, K. I. I. C. H. I. R. O., Tsukayama, H. I. R. O. S. H. I., Nakamura, T. A. T. S. U. Z. O., Ikeuchi, R., Kawamoto, M. A. S. A. Z. U. M. I., & Kasuya, D. A. I. C. H. I. (2001). Multi-center randomized, controlled trial of acupuncture with electric stimulation and acupuncture-like transcutaneous electrical nerve stimulation for lumbago. *J Japan Soc Acupunct Moxibustion,* 51, 175-84 (hereafter, "Sakai 2001").

The intensity of stimulation should be sufficient to activate the underlying nerves without causing discomfort. In electroacupuncture, sometimes this is identified by muscle twitching or maximal comfort level. Such intensity will vary depending upon the depth of insertion of the device and differences in anatomy. As a general guide, intensity should vary between about 2 mA and 37 mA.

Mechanical Design

A perspective view of an exemplary embodiment of an implantable electroacupuncture device (IEAD) 100 that may be used for the purposes described herein is shown in FIG. 1. The IEAD 100 may also sometimes be referred to as an implantable electroacupuncture stimulator (IEAS). As seen in FIG. 1, the IEAD 100 has the appearance of a disc or coin, having a front side 106, a back side 102 (not visible in FIG. 1) and an edge side 104.

As used herein, the "front" side of the IEAD 100 is the side that is positioned so as to face the target stimulation point (e.g., the desired acupoint) where EA stimulation is to be applied when the IEAD is implanted. The front side 106 may also be referred to herein as the "cathode side" 106. The "back" side 102 is the side opposite the front side and is the side farthest away from the target stimulation point when the IEAD is implanted. The "back" side 102 may also be referred to herein as the "skin" side 102. The "edge" of the IEAD is the side that connects or joins the front side to the back side. In FIG. 1, the IEAD 100 is oriented to show the front side 106 and a portion of the edge side 104.

Many of the features associated with the mechanical design of the IEAD 100 shown in FIG. 1 are the subject of a prior U.S. Provisional patent application, entitled "Radial Feed-Through Packaging for An Implantable Electroacupuncture Device", Application No. 61/676,275, filed 26 Jul. 2012, which application is incorporated here by reference.

It should be noted here that throughout this application, the terms IEAD 100, IEAD housing 100, bottom case 124, can 124, or IEAD case 124, or similar terms, are used to describe the housing structure of the EA device. In some instances it may appear these terms are used interchangeably. However, the context should dictate what is meant by these terms. As the drawings illustrate, particularly FIG. 7, there is a bottom case 124 that comprises the "can" or "container" wherein the components of the IEAD 100 are first placed and assembled during manufacture of the IEAD 100. When all of the components are assembled and placed within the bottom case 124, a cover plate 122 is welded to the bottom case 124 to form the hermetically-sealed housing of the IEAD. The cathode electrode 110 is attached to the outside of the bottom case 124 (which is the front side 106 of the device), and the ring anode electrode 120 is attached, along with its insulating layer 129, around the perimeter edge 104 of the bottom case 124. Finally, a layer of silicone molding 125 covers the IEAD housing except for the outside surfaces of the anode ring electrode and the cathode electrode.

Figure 7:
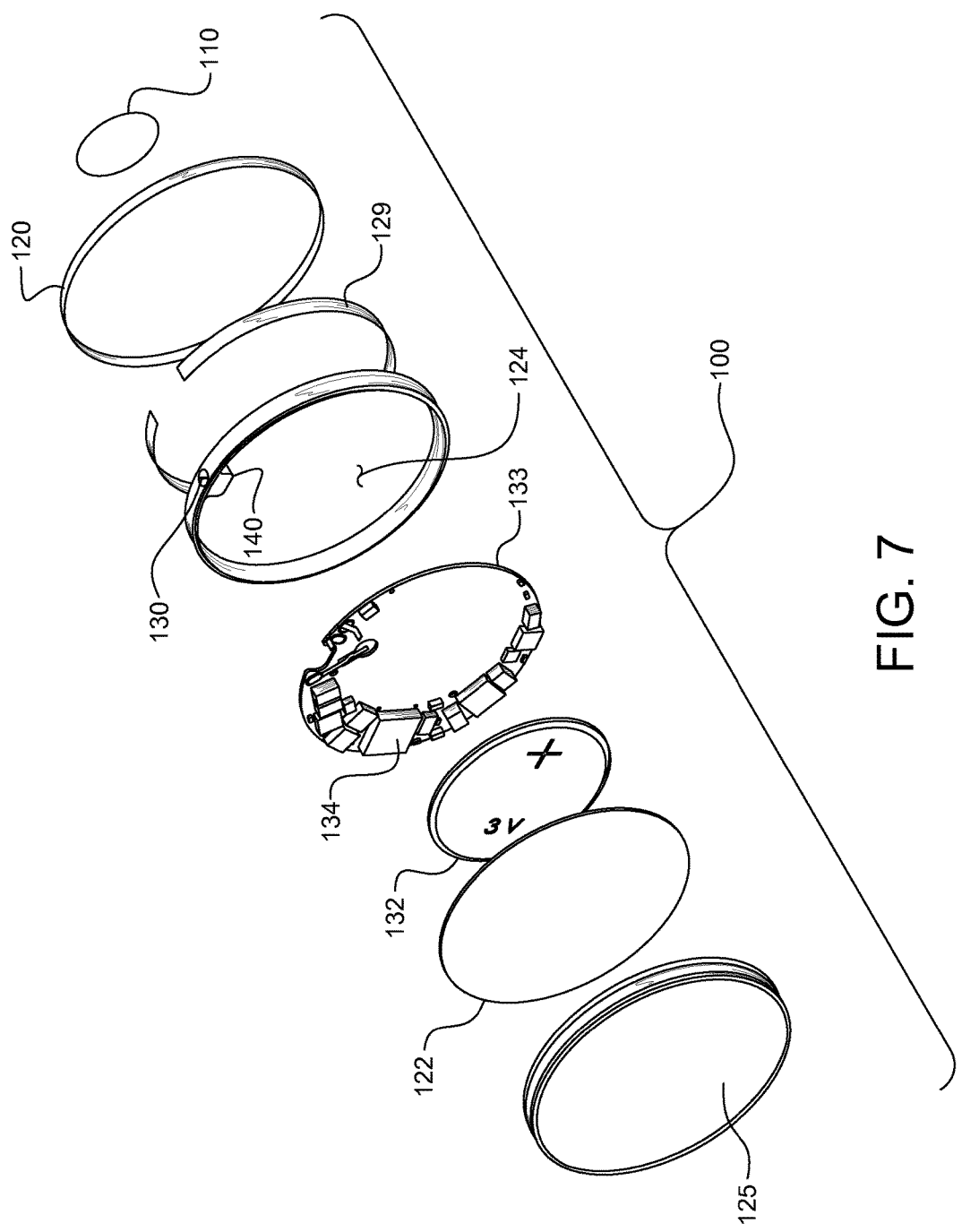
FIG. 7 is an exploded view of the IEAD assembly of the IEAD of FIG. 1, illustrating its constituent parts.

The embodiment of the IEAD 100 shown in FIG. 1 utilizes two electrodes, a cathode electrode 110 that is centrally positioned on the front side 106 of the IEAD 100, and an anode electrode 120. The anode electrode 120 is a ring electrode that fits around the perimeter edge 104 of the IEAD 100. Not visible in FIG. 1, but which is described hereinafter in connection with the description of FIG. 7, is a layer of insulating material 129 that electrically insulates the anode ring electrode 120 from the perimeter edge 104 of the housing or case 124.

Not visible in FIG. 1, but an exemplary feature of the mechanical design of the IEAD 100, is the manner in which an electrical connection is established between the ring electrode 120 and electronic circuitry carried inside of the IEAD 100. This electrical connection is established using a radial feed-through pin that fits within a recess formed in a segment of the edge of the case 124, as explained more fully below in connection with the description of FIGS. 5, 5A, 5B and 7.

In contrast to the feed-through pin that establishes electrical contact with the anode electrode, electrical connection with the cathode electrode 110 is established simply by forming or attaching the cathode electrode 110 to the front surface 106 of the IEAD case 124. In order to prevent the entire case 124 from functioning as the cathode (which is done to better control the electric fields established between the anode and cathode electrodes), the entire IEAD housing is covered in a layer of silicone molding 125 (see FIG. 7), except for the outside surface of the anode ring electrode 120 and the cathode electrode 110.

The advantage of using a central cathode electrode and a ring anode electrode is described in U.S. Provisional Patent Application No. 61/672,257, filed 6 Mar. 2012, entitled "Electrode Configuration for Implantable Electroacupuncture Device", which application is incorporated herein by reference. One significant advantage of this electrode configuration is that it is symmetrical. That is, when implanted, the surgeon or other medical personnel performing the implant procedure, need only assure that the cathode side of the IEAD 100, which (for the embodiment shown in FIGS. 1-7) is the front side of the device, faces the target tissue location that is to be stimulated. In addition, the IEAD must be implanted over the desired acupoint, or other tissue location, that is intended to receive the electroacupuncture (EA) stimulation. The orientation of the IEAD 100 is otherwise not important.

Figure 1C:
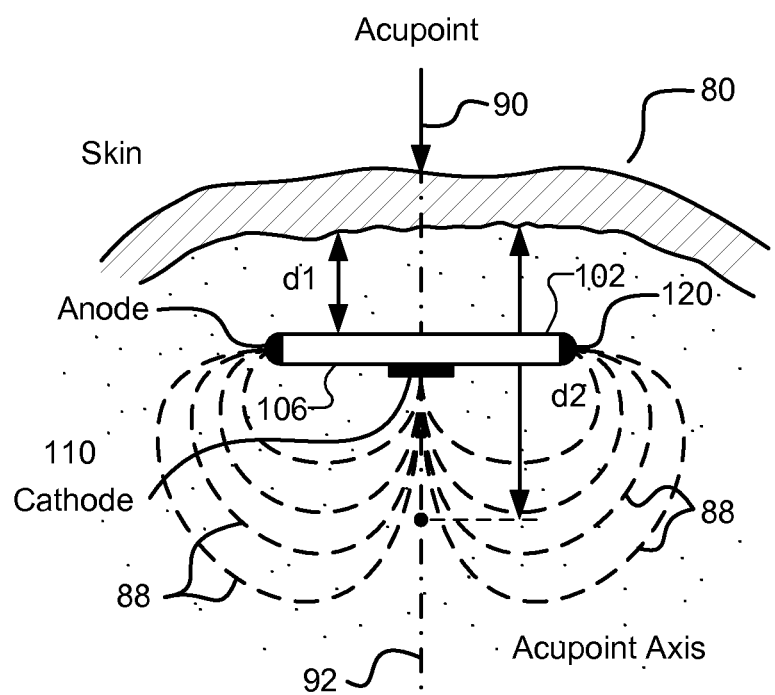
FIG. 1C shows a sectional view of an IEAD implanted at a selected target stimulation site, and illustrates the electric field gradient lines created when an electroacupuncture (EA) pulse is applied to the tissue through the central electrode and ring electrode attached to the bottom surface and perimeter edge, respectively, of the IEAD housing.
Figure 1A:
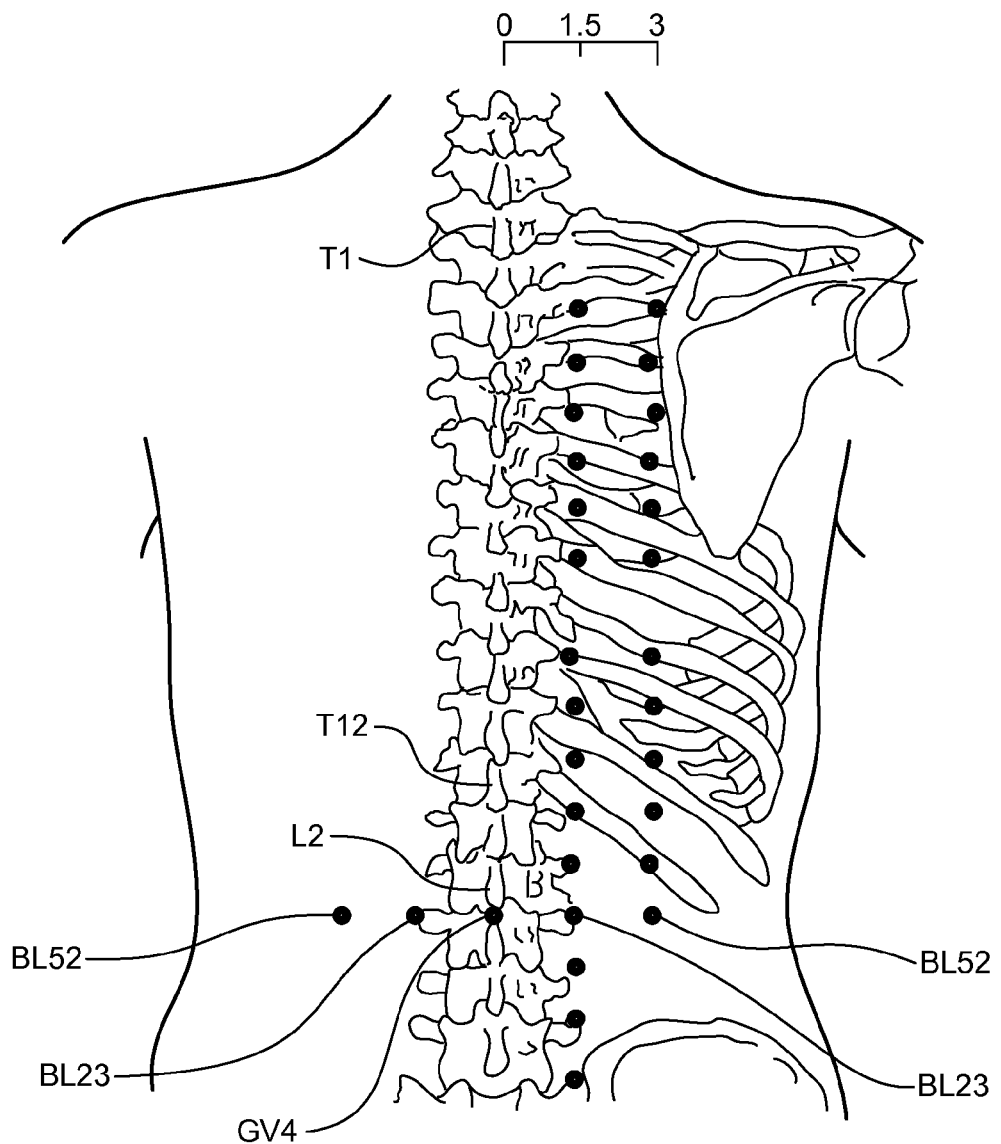
FIG. 1A illustrates the lumbar region of a patient and shows the location of some representative acupoints in that region, e.g., BL52 (also sometimes referred to as acupoint Zhishi), BL23 (also sometimes referred to as acupoint Shenshu) and GV4 (also sometimes referred to as acupoint Mingmen).

FIG. 1A illustrates the lumbar region of a patient and shows the location of some representative acupoints in that region, e.g., BL52 (also sometimes referred to as acupoint Zhishi), BL23 (also sometimes referred to as acupoint Shenshu) and GV4 (also sometimes referred to as acupoint Mingmen).

Figure 1B:
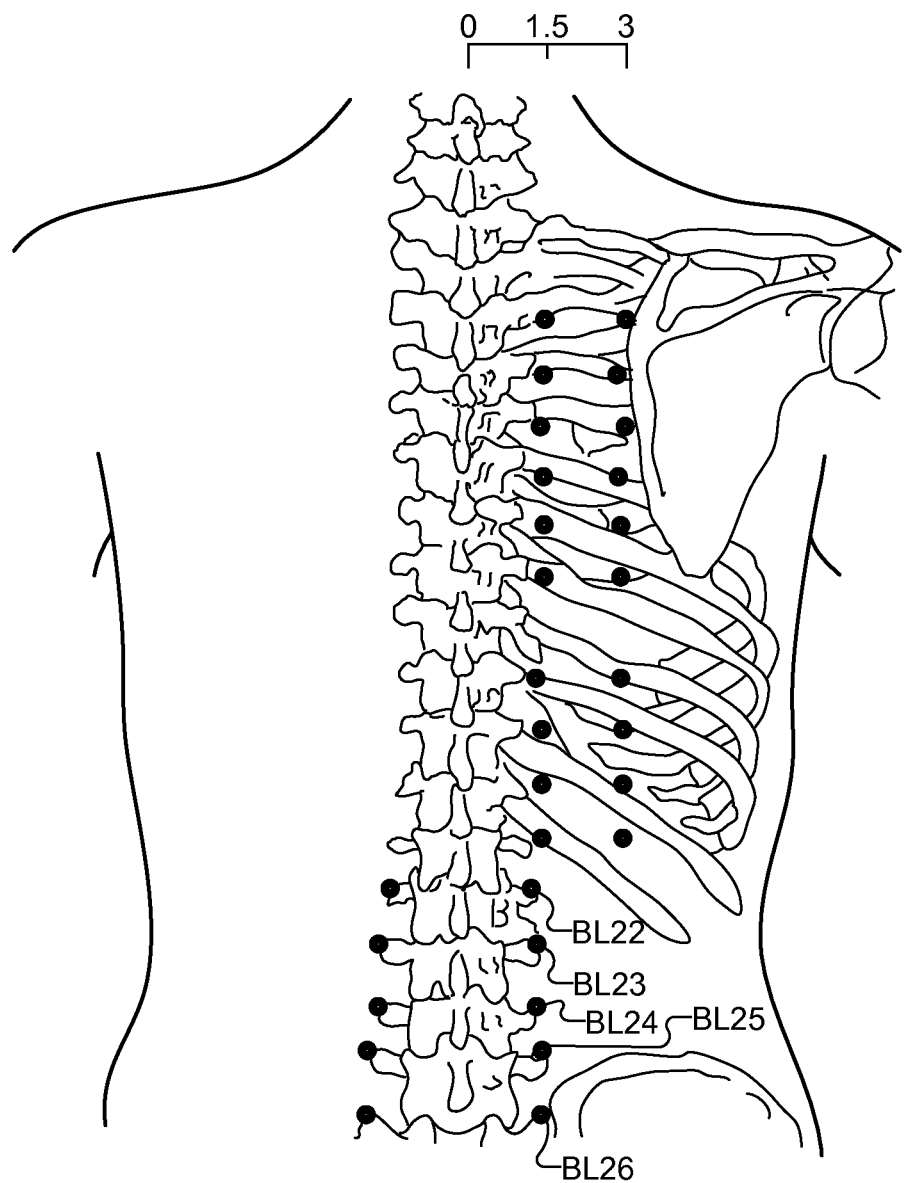
FIG. 1B illustrates the location of acupoints BL22, BL23, BL24, BL25 and BL26, any one of which, or any combination of which, may serve as a target stimulation site(s) at which an IEAD may be implanted for the treatment of chronic low back pain.

FIG. 1B also illustrates the lumbar region of a patient and shows the location of acupoints BL22, BL23, BL24, BL25 and BL26, any one of which, or any combination of which, may serve as a target stimulation site(s) at which an IEAD 100 may be implanted for the treatment of chronic low back pain as taught herein.

As seen in FIG. 1A, the acupoint BL23, for example, resides in the lumbar region, at the same level as the inferior border of the spinous process of the second lumbar vertebra (L2), about 1.5 B-cun lateral to the posterior median line. The measurement system using units of "B-cun" is a proportional bone (skeletal) measurement system described in the *WHO Standard Acupuncture Point Locations* 2008 reference book cited above. See, in particular, pages 2, 11-13 and 20-21 of that reference book, especially FIG. 20, on page 20, and FIG. 21, on page 21 (which *WHO Standard Acupuncture Point Locations* 2008 reference book is incorporated herein by reference in its entirety). However, for an average-sized adult, a measurement of 1.5 B-cun may be considered to be approximately 1.5 inches.

FIG. 1B shows that the location of acupoints BL22, BL23, BL24, BL25 and BL26 within the lumbar region are located at approximately the same lateral position as is acupoint BL23, but at different levels relative to the vertebra. BL22, for example, is between the first lumbar vertebra (L1) and the second lumbar vertebra (L2). BL23 is between the second lumbar vertebra (L2) and the third lumbar vertebra (L3), BL24 is between the third lumbar vertebra (L3) and the fourth lumbar vertebra (L4), BL25 is between the fourth lumbar vertebra (L4) and the fifth lumbar vertebra (L5), and BL26 is just below the fifth lumbar vertebra (L5).

An implanted leadless IEAD 100 is illustrated generally in FIG. 1C, which shows a sectional view of body tissue 80 of the patient wherein a representative acupoint 90 has been identified that is to receive acupuncture treatment (in this case electroacupuncture, or EA, treatment). An incision (not shown in FIG. 1B) is made into the body tissue 80 a short distance, e.g., 10-15 mm, away from the acupoint 90. As necessary, the surgeon may form a pocket under the skin at the acupoint location. The IEAD 100, with its top side 102 being closest to the skin, is then carefully inserted through the incision into the pocket so that the center of the IEAD is located under the acupoint 90 on the skin surface. With the IEAD 100 in place, the incision is sewn or otherwise closed, leaving the IEAD 100 under the skin 80 at the location of the acupoint 90 where electroacupuncture (EA) stimulation is desired.

In this regard, it should be noted that while the target stimulation point is generally identified by an "acupoint," which is typically shown in drawings and diagrams as residing on the surface of the skin, the surface of the skin is not the actual target stimulation point. Rather, whether such stimulation comprises manual manipulation of a needle inserted through the skin at the location on the skin surface identified as an "acupoint", or whether such stimulation comprises electrical stimulation applied through an electrical field oriented to cause stimulation current to flow through the tissue at a prescribed depth below the acupoint location on the skin surface, the actual target tissue point to be stimulated is located beneath the skin at a depth $d_2$ below or underlying the acupoint 90, where the depth $d_2$ varies depending on the particular acupoint location. When stimulation is applied at the target tissue point, such stimulation is effective at treating a selected condition of the patient, e.g., chronic low back pain, because there is something in the tissue at that target location, or in the vicinity of that target location, such as a nerve, a tendon, a muscle, or other type of tissue, that responds to the applied stimulation in a manner that contributes favorably to the treatment of the condition experienced by the patient.

FIG. 1C illustrates a sectional view of the IEAD 100 implanted so as to be centrally located under the skin at the selected acupoint 90, and aligned with an acupoint axis line 92. Usually, for most patients, the IEAD 100 is implanted at a depth d1 of approximately 2-4 mm under the skin. The top (or "back") side 102 of the IEAD is nearest to the skin 80 of the patient. The bottom (or "cathode") side 106 of the IEAD, which is the side on which the central cathode electrode 110 resides, is farthest from the skin. Because the cathode electrode 110 is centered on the bottom of the IEAD, and because the IEAD 100 is implanted so as to be centered under the location on the skin where the acupoint 90 is located, the cathode 110 is also centered over the acupoint axis line 92.

FIG. 1C further illustrates the electric field gradient lines 88 that are created in the body tissue 86 surrounding the acupoint 90 and the acupoint axis line 92. (Note: for purposes herein, when reference is made to providing EA stimulation at a specified acupoint, it is understood that the EA stimulation is provided at a depth of approximately d2 below the location on the skin surface where the acupoint is indicated as being located.) As seen in FIG. 1C, the electric field gradient lines are strongest along a line that coincides with, or is near to, the acupoint axis line 92. It is thus seen that one of the main advantages of using a symmetrical electrode configuration that includes a centrally located electrode surrounded by an annular electrode is that the precise orientation of the IEAD within its implant location is not important. So long as one electrode is centered over the desired target location, and the other electrode surrounds the first electrode (e.g., as an annular electrode), a strong electric field gradient is created that is aligned with the acupoint axis line. This causes the EA stimulation current to flow along (or very near) the acupoint axis line 92, and will result in the desired EA stimulation in the tissue at a depth d2 below the acupoint location indicated on the skin.

FIG. 2 shows a plan view of the "cathode" (or "front") side 106 of the IEAD 100. As seen in FIG. 2, the cathode electrode 110 appears as a circular electrode, centered on the front side, having a diameter D1. The IEAD housing has a diameter D2 and an overall thickness or width W2. For the exemplary embodiment shown in these figures, D1 is about 4 mm, D2 is about 23 mm and W2 is a little over 2 mm (2.2 mm).

FIG. 2A shows a side view of the IEAD 100. The ring anode electrode 120, best seen in FIG. 2A, has a width W1 of about 1.0 mm, or approximately ½ of the width W2 of the IEAD.

FIG. 3 shows a plan view of the "back" (or "skin") side 102 of the IEAD 100. As will be evident from subsequent figure descriptions, e.g., FIGS. 5A and 5B, the back side 102 of the IEAD 100 comprises a cover plate 122 that is welded in place once the bottom case 124 has all of the electronic circuitry, and other components, placed inside of the housing.

FIG. 3A is a sectional view of the IEAD 100 of FIG. 1 taken along the line A-A of FIG. 3. Visible in this sectional view is the feed-through pin 130, including the distal end of the feed-through pin 130 attached to the ring anode electrode 120. Also visible in this section view is an electronic assembly 133 on which various electronic components are mounted, including a disc-shaped battery 132. FIG. 3A further illustrates how the cover plate 122 is welded, or otherwise bonded, to the bottom case 124 in order to form the hermetically-sealed IEAD housing 100.

Figure 4:
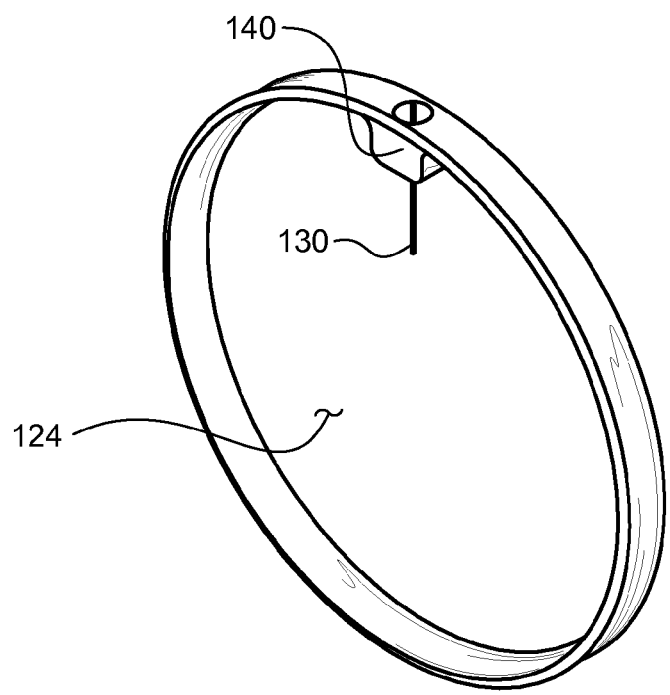
FIG. 4 is a perspective view of the IEAD housing, including a feed-through pin, before the electronic components are placed therein, and before being sealed with a cover plate.

FIG. 4 shows a perspective view of the IEAD case 124, including the feed-through pin 130, before the electronic components are placed therein, and before being sealed with the a cover plate 122. The case 124 is similar to a shallow "can" without a lid, having a short side wall around its perimeter. Alternatively, the case 124 may be viewed as a short cylinder, closed at one end but open at the other. (Note, in the medical device industry the housing of an implanted device is often referred to as a "can".) The feed-through pin 130 passes through a segment of the wall of the case 124 that is at the bottom of a recess 140 formed in the wall. The use of this recess 140 to hold the feed-through pin 130 may keep the temperature-sensitive portions of the feed-through assembly (those portions that could be damaged by excessive heat) away from the thermal shock and residual weld stress inflicted upon the case 124 when the cover plate 122 is welded thereto.

Figure 4A:
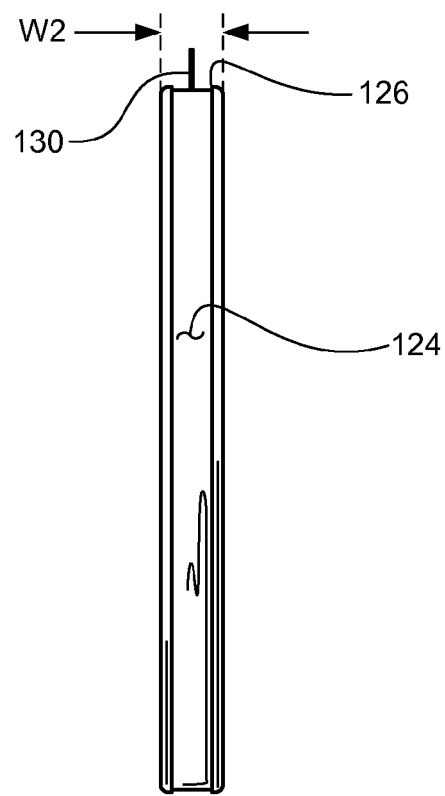
FIG. 4A is a side view of the IEAD housing of FIG. 4.

FIG. 4A is a side view of the IEAD case 124, and shows an annular rim 126 formed on both sides of the case 124. The ring anode electrode 120 fits between these rims 126 once the ring electrode 120 is positioned around the edge of the case 124. (This ring electrode 120 is, for most configurations, used as an anode electrode. Hence, the ring electrode 120 may sometimes be referred to herein as a ring anode electrode. However, it is noted that the ring electrode could also be employed as a cathode electrode, if desired.) A silicone insulator layer 129 (see FIG. 7) is placed between the backside of the ring anode electrode 120 and the perimeter edge of the case 124 where the ring anode electrode 120 is placed around the edge of the case 124.

FIG. 5 shows a plan view of the empty IEAD case 124 shown in the perspective view of FIG. 4. An outline of the recess cavity 140 is also seen in FIG. 5, as is the feed-through pin 130. A bottom edge of the recess cavity 140 is located a distance D5 radially inward from the edge of the case 124. In one embodiment, the distance D5 is between about 2.0 to 2.5 mm. The feed-through pin 130, which is just a piece of solid wire, is shown in FIG. 5 extending radially outward from the case 124 above the recess cavity 140 and radially inward from the recess cavity towards the center of the case 124. The length of this feed-through pin 130 is trimmed, as needed, when a distal end (extending above the recess) is connected (welded) to the anode ring electrode 120 (passing through a hole in the ring electrode 120 prior to welding) and when a proximal end of the feed-through pin 130 is connected to an output terminal of the electronic assembly 133.

FIG. 5A depicts a sectional view of the IEAD housing 124 of FIG. 5 taken along the section line A-A of FIG. 5. FIG. 5B shows an enlarged view or detail of the portion of FIG. 5A that is encircled with the line B. Referring to FIGS. 5A and 5B jointly, it is seen that the feed-through pin 130 is embedded within an insulator material 136, which insulating material 136 has a diameter of D3. The feed-through pin assembly (which pin assembly comprises the combination of the pin 130 embedded into the insulator material 136) resides on a shoulder around an opening or hole formed in the bottom of the recess 140 having a diameter D4. For the embodiment shown in FIGS. 5A and 5B, the diameter D3 is 0.95-0.07 mm, where the −0.07 mm is a tolerance. (Thus, with the tolerance considered, the diameter D3 may range from 0.88 mm to 0.95 mm.) The diameter D4 is 0.80 mm with a tolerance of −0.06 mm. (Thus, with the tolerance considered, the diameter D4 could range from 0.74 mm to 0.80 mm.)

The feed-through pin 130 may be made of pure platinum 99.95%. An exemplary material for the insulator material 136 is Ruby or alumina. The IEAD case 124, and the cover 122, may be made from titanium. The feed-through assembly, including the feed-through pin 130, ruby/alumina insulator 136 and the case 124 are hermetically sealed as a unit by gold brazing. Alternatively, active metal brazing can be used. (Active metal brazing is a form of brazing which allows metal to be joined to ceramic without metallization.)

The hermeticity of the sealed IEAD housing is tested using a helium leak test, as is common in the medical device industry. The helium leak rate should not exceed $1 \times 10^{-9}$ STD cc/sec at 1 atm pressure. Other tests are performed to verify the case-to-pin resistance (which should be at least $15 \times 10^6$ Ohms at 100 volts DC), the avoidance of dielectric breakdown or flashover between the pin and the case 124 at 400 volts AC RMS at 60 Hz and thermal shock.

One advantage provided by the feed-through assembly shown in FIGS. 4A, 5, 5A and 5B is that the feed-through assembly made from the feed-through pin 130, the ruby insulator 136 and the recess cavity 140 (formed in the case material 124) may be fabricated and assembled before any other components of the IEAD 100 are placed inside of the IEAD case 124. This advantage greatly facilitates the manufacture of the IEAD device.

Additional details associated with the radial feed-through pin 130, and its use within an electronic package, such as the IEAD 100 described herein, may be found in Applicant's co-pending patent application, "Radial Feed Through Packaging for an Implantable Electroacupuncture Device", application Ser. No. 13/777,901, filed Feb. 26, 2013, which application is incorporated herein by reference.

Turning next to FIG. 6, there is shown a perspective view of an electronic assembly 133. The electronic assembly 133 includes a multi-layer printed circuit (pc) board 138, or equivalent mounting structure, on which a battery 132 and various electronic components 134 are mounted. This assembly is adapted to fit inside of the empty bottom housing 124 of FIG. 4 and FIG. 5.

FIGS. 6A and 6B show a plan view and side view, respectively, of the electronic assembly 133 shown in FIG. 6. The electronic components are assembled and connected together so as to perform the circuit functions needed for the IEAD 100 to perform its intended functions. These circuit functions are explained in more detail below under the sub-heading "Electrical Design". Additional details associated with these functions may also be found in Applicant's earlier application, application Ser. No. 13/598,582, filed Aug. 29, 2012.

FIG. 7 shows an exploded view of the complete IEAD 100, illustrating its main constituent parts. As seen in FIG. 7, the IEAD 100 includes, starting on the right and going left, a cathode electrode 110, a ring anode electrode 120, an insulating layer 129, the bottom case 124 (the "can" portion of the IEAD housing, and which includes the feed-through pin 130 which passes through an opening in the bottom of the recess 140 formed as part of the case, but wherein the feed-through pin 130 is insulated and does not make electrical contact with the metal case 124 by the ruby insulator 136), the electronic assembly 133 (which includes the battery 132 and various electronic components 134 mounted on a PC board 138) and the cover plate 122. The cover plate 122 is welded to the edge of the bottom case 124 using laser beam welding, or some equivalent process, as one of the final steps in the assembly process.

Other components included in the IEAD assembly, but not necessarily shown or identified in FIG. 7, include adhesive patches for bonding the battery 132 to the pc board 138 of the electronic assembly 133, and for bonding the electronic assembly 133 to the inside of the bottom of the case 124. To prevent high temperature exposure of the battery 132 during the assembly process, conductive epoxy is used to connect a battery terminal to the pc board 138. Because the curing temperature of conductive epoxy is 125° C., the following process is used: (a) first cure the conductive epoxy of a battery terminal ribbon to the pc board without the battery, (b) then glue the battery to the pc board using room temperature cure silicone, and (c) laser tack weld the connecting ribbon to the battery.

Also not shown in FIG. 7 is the manner of connecting the proximal end of the feed-through pin 130 to the pc board 138, and connecting a pc board ground pad to the case 124. An exemplary method of making these connections is to use conductive epoxy and conductive ribbons, although other connection methods known in the art may also be used.

Further shown in FIG. 7 is a layer of silicon molding 125 that is used to cover all surfaces of the entire IEAD 100 except for the anode ring electrode 120 and the circular cathode electrode 110. An over-molding process is used to accomplish this, although over-molding using silicone LSR 70 (curing temperature of 120° C.) with an injection molding process cannot be used. Over-molding processes that may be used include: (a) molding a silicone jacket and gluing the jacket onto the case using room temperature cure silicone (RTV) inside of a mold, and curing at room temperature; (b) injecting room temperature cure silicone in a PEEK or Teflon® mold (silicone will not stick to the Teflon® or PEEK material); or (c) dip coating the IEAD 100 in room temperature cure silicone while masking the electrode surfaces that are not to be coated. (Note: PEEK is a well known semicrystalline thermoplastic with excellent mechanical and chemical resistance properties that are retained at high temperatures.)

When assembled, the insulating layer 129 is positioned underneath the ring anode electrode 120 so that the anode electrode does not short to the case 124. The only electrical connection made to the anode electrode 120 is through the distal tip of the feed-through pin 130. The electrical contact with the cathode electrode 110 is made through the case 124. However, because the entire IEAD is coated with a layer of silicone molding 125, except for the anode ring electrode 120 and the circular cathode electrode 110, all stimulation current generated by the IEAD 100 must flow between the exposed surfaces of the anode and cathode.

It is noted that while the exemplary configuration described herein uses a ring anode electrode 120 placed around the edges of the IEAD housing, and a circular cathode electrode 110 placed in the center of the cathode side of the IEAD case 124, such an arrangement could be reversed, i.e., the ring electrode could be the cathode, and the circular electrode could be the anode.

Moreover, the location and shape of the electrodes may be configured differently than is shown in the exemplary embodiment described above in connection with FIGS. 1, and 2-7. For example, the ring anode electrode 120 need not be placed around the perimeter of the device, but such electrode may be a flat circumferential electrode that assumes different shapes (e.g., round or oval) that is placed on the front or back surface of the IEAD so as to surround the central electrode. Further, for some embodiments, the surfaces of the anode and cathode electrodes may have convex surfaces.

It is also noted that while an exemplary embodiment has been disclosed herein that incorporates a round, or short cylindrical-shaped housing, also referred to as a coin-shaped housing, the methods and systems described herein do not require that the case 124 (which may also be referred to as a "container"), and its associated cover plate 122, be round. The case could just as easily be an oval-shaped, rectangular-shaped (e.g., square with smooth corners), polygonal-shaped (e.g., hexagon-, octagon-, pentagon-shaped), button-shaped (with convex top or bottom for a smoother profile) device. Any of these alternate shapes, or others, would still permit the basic principles of the methods and systems described herein to be used to provide a robust, compact, thin, case to house the electronic circuitry and power source described herein; as well as to help protect a feed-through assembly from being exposed to excessive heat during assembly, and to allow the thin device to provide the benefits described herein related to its manufacture, implantation and use. For example, as long as the device remains relatively thin, e.g., no more than about 2-3 mm, and does not have a maximum linear dimension greater than about 25 mm, then the device can be readily implanted in a pocket over the tissue area where the selected acupuoint(s) is located. As long as there is a recess in the wall around the perimeter of the case wherein the feed-through assembly may be mounted, which recess effectively moves the wall or edge of the case inwardly into the housing a safe thermal distance, as well as a safe residual weld stress distance, from the perimeter wall where a hermetically-sealed weld occurs, the principles of the methods and systems described herein apply.

Further, it should be noted that while the exemplary configuration of the IEAD described herein utilizes a central electrode on one of its surfaces that is round, having a diameter of nominally 4 mm, such central electrode need not necessarily be round. It could be oval shaped, polygonal-shaped, or shaped otherwise, in which case its size is best defined by its maximum width, which will generally be no greater than about 7 mm.

Finally, it is noted that the electrode arrangement may be modified somewhat, and the desired attributes of the methods and systems described herein may still be achieved. For example, as indicated previously, an exemplary electrode configuration for use with the methods and systems described herein utilizes a symmetrical electrode configuration, e.g., an annular electrode of a first polarity that surrounds a central electrode of a second polarity. Such a symmetrical electrode configuration makes the implantable electroacupuncture device (IEAD) relatively immune to being implanted in an improper orientation relative to the body tissue at the selected acupoint(s) that is being stimulated. However, an electrode configuration that is not symmetrical may still be used and many of the therapeutic effects of the methods and systems described herein may still be achieved. For example, two spaced-apart electrodes on a front surface of the housing, one of a first polarity, and a second of a second polarity, could still, when oriented properly with respect to a selected acupoint tissue location, provide some desired therapeutic results.

Applicant's earlier-filed application, application Ser. No. 13/598,582, filed Aug. 29, 2012, and its appendices, schematically illustrate some alternative electrode configurations that may be used with the methods and systems described herein. All of these alternative electrode configurations, shown, e.g., in FIG. 7A of the Applicant's earlier-filed application, and the accompanying text that describes these alternative electrode configurations, as well as in the appendices of the earlier-filed application, are incorporated herein by reference.

Note, as has already been described above, the phrase "electrode or electrode array," or "electrodes or electrode arrays," may also be referred to herein as "electrode/array" or "electrodes/arrays," respectively. For the ease of explanation, when an electrode array is referred to herein that comprises a plurality (two or more) of individual electrodes of the same polarity, the individual electrodes of the same polarity within the electrode array may also be referred to as "individual electrodes", "segments" of the electrode array, "electrode segments", or just "segments".

The alternate electrode configurations shown in Applicant's earlier-filed application, and its appendices, are only representative of a few electrode configurations that may be used with the present methods and systems described herein. Further, it is to be noted that a central electrode/array need not have the same number of electrode segments as does a surrounding electrode/array. Typically, a central electrode/array of a first polarity will be a single electrode; whereas the surrounding electrode/array of a second polarity may have n individual electrode segments, where n is an integer that can vary from 1, 2, 3, . . . n. Thus, for a circumferential electrode array where n=4, there are four electrode segments of the same polarity arranged in circumferential pattern around a central electrode/array. If the circumferential electrode array with n=4 is a symmetrical electrode array, then the four electrode segments will be spaced apart equally in a circumferential pattern around a central electrode/array. When n=1, the circumferential electrode array reduces to a single circumferential segment or a single annular electrode that surrounds a central electrode/array.

Additionally, the polarities of the electrode/arrays may be selected as needed. That is, while a central electrode/array is typically a cathode (−), and a surrounding electrode/array is typically an anode (+), these polarities may be reversed.

It should be noted that the shape of the circumferential electrode/array, whether circular, oval, or other shape, need not necessarily be the same shape as the IEAD housing, unless the circumferential electrode/array is attached to a perimeter edge of the IEAD housing. The IEAD housing may be round, or it may be oval, or it may have a polygon shape, or other shape, as needed to suit the needs of a particular manufacturer and/or patient.

For a more thorough description of the electrode materials best suited for the cathode electrode 110 and the anode electrode 120, as well as the surface area required for these electrodes, see Applicant's co-pending patent application, "Electrode Configuration for an Implantable Electroacupuncture Device", application Ser. No. 13/776,155, filed Feb. 25, 2013, which application is incorporated hereby by reference.

Additional electrode configurations, both symmetrical electrode configurations and non-symmetrical electrode configurations, that may be used with an EA stimulation device as described herein, are illustrated in the appendices of Applicant's earlier-filed application, U.S. application Ser. No. 13/598,582, filed Aug. 29, 2012, previously incorporated herein by reference.

One of the advantages of the IEAD 100 shown in FIG. 1 is that it is leadless. However, this advantage can sometimes create a difficulty when the desired tissue stimulation point does not allow the IEAD 100 to be placed sufficiently near the specified target stimulation point in order to stimulate such target point with the needed intensity. To overcome this difficulty, an alternative embodiment of the IEAD housing—shown in FIGS. 7A, 7B, 7C and 7D—uses a short lead attached to, e.g., the cathode, that allows the cathode to be placed closer to the target stimulation site than otherwise would be possible. For treating lower back pain, this means the alternative embodiment of the IEAD housing shown in FIG. 7A, 7B, 7C, or 7D may be used to place the cathode closer to the lumbar nerve, and dorsal roots.

Thus, shown in FIGS. 7A-7D, is an example of an alternate housing configuration that may be used in order to place a unipolar electrode, typically the cathode electrode, closer to the desired target stimulation point, e.g., a specified acupoint, than is possible using only the IEAD 100 shown in FIG. 1.

As seen in FIGS. 7A-7D, a short monopolar lead 340, having its proximal end mechanically attached to the IEAD housing and electrically connected to electrical circuitry within the IEAD that would normally be connected to one of the two electrodes formed on the case of the IEAD if the IEAD were leadless, allows the positioning of the electrode not on the case of the IEAD to be more precisely placed than might otherwise be achievable. In this alternate configuration, stimulation pulses are applied to target tissue by energizing the two electrodes, one on the case of the IEAD, the other at the distal end of the short lead 340. Such stimulation is referred to as "monopolar" stimulation because it occurs between an electrode(s) having a single polarity at the end of the lead 340 and an electrode(s) having a single (and opposite) polarity at the case of the IEAD. A lead with a single-polarity electrode at its distal end may also sometimes be referred to as a "unipolar" lead.

Figure 7A:
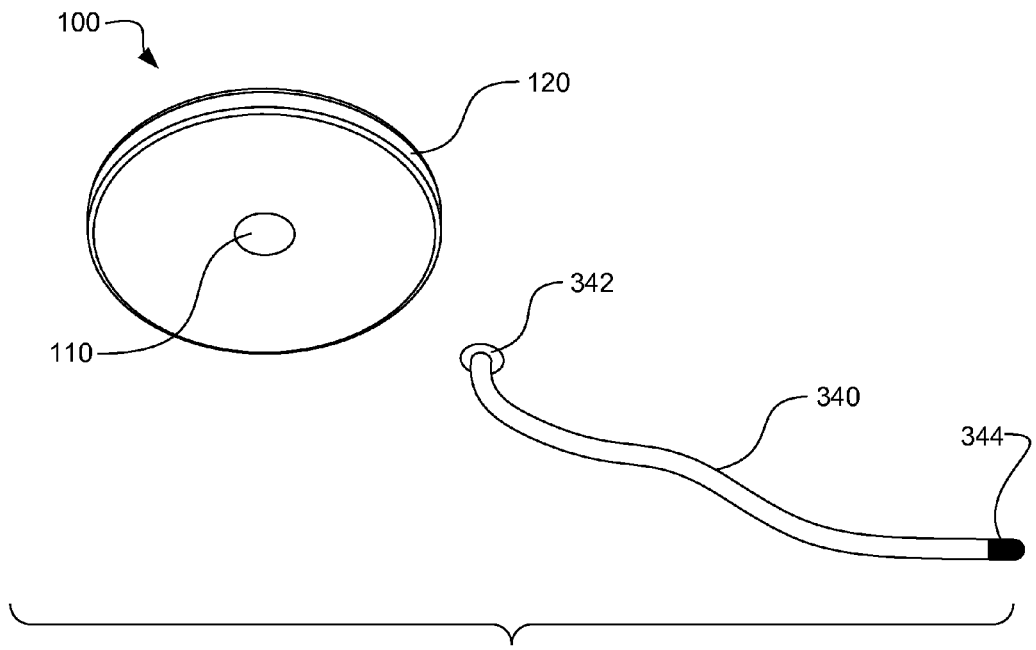
FIG. 7A shows an alternative embodiment of the IEAD housing adapted to have a short extension lead affixed to the cathode electrode located on the housing, with a distal cathode electrode located at the distal end of the extension lead.

FIG. 7A illustrates the main components of the alternative embodiment of the IEAD housing described above. As seen in FIG. 7A, these components include (1) a leadless IEAD device 100 of the type described previously in connection with FIGS. 1-7; and (2) a smooth and relatively short lead 340. For purposes herein, the lead 340 comprises a conductive wire or cable placed inside of a smooth non-conductive catheter. In other words the lead 340 may be thought of as a catheter lead, or a flexible, insulated, unipolar extension lead. The conductive wire or a cable, comprising several conductive wire fibers wound together, is exposed electrically to the tissue through an electrode interface at a distal end 344 of the catheter lead 340. The length of the catheter lead 340 is typically no more than about 50 mm, and may be as short as 10 mm.

Figure 7B:
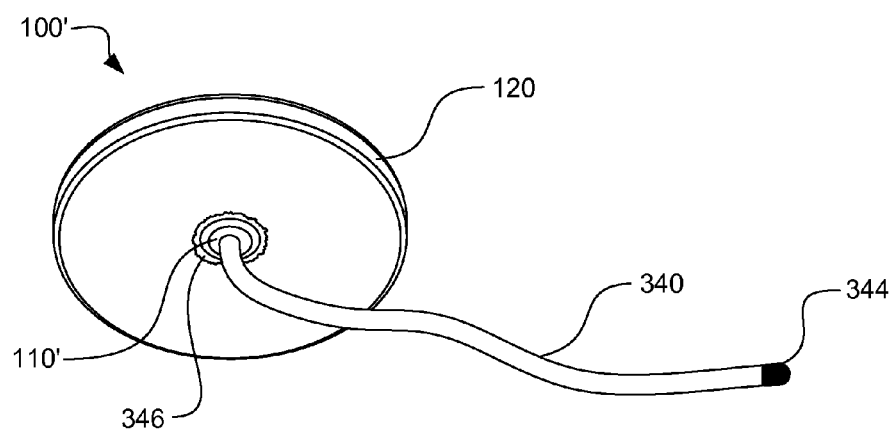
FIG. 7B shows a proximal end of the short extension lead of FIG. 7A attached to the central cathode electrode located on the IEAD housing, whereby the combination of the IEAD housing and extension lead allow the cathode electrode (located at the distal end of the extension lead) to be positioned closer to a desired target location.

FIG. 7B shows a configuration wherein the conductive wire cable at the proximal end 342 of the extension lead 340 is welded, or otherwise bonded to, the surface of the housing of the IEAD 100. Once so attached, the entire surface of the IEAD housing is overmolded, painted or otherwise covered, with a layer 346 of silicon, or other suitable insulator, so that an electrical connection can be made with the catheter electrode only through the exposed electrode interface at the distal end 344 of the short lead 340 conductive wire. The extension catheter lead 340 thus effectively relocates or transfers the position of the catheter electrode from a surface of the IEAD housing to the distal end 344 of the catheter lead. A suitable conductive electrode surface, e.g., in the form of a cap, may be formed at the distal end of the catheter lead 344, as needed or desired using electrode interface materials such as platinum or platinum iridium alloy.

FIG. 7B thus shows a modified EA device 100', having the proximal end of an extension cable 340 attached to its housing 120, thereby effectively relocating the position of the cathode electrode to the distal end 344 of the catheter lead.

Figure 7C:
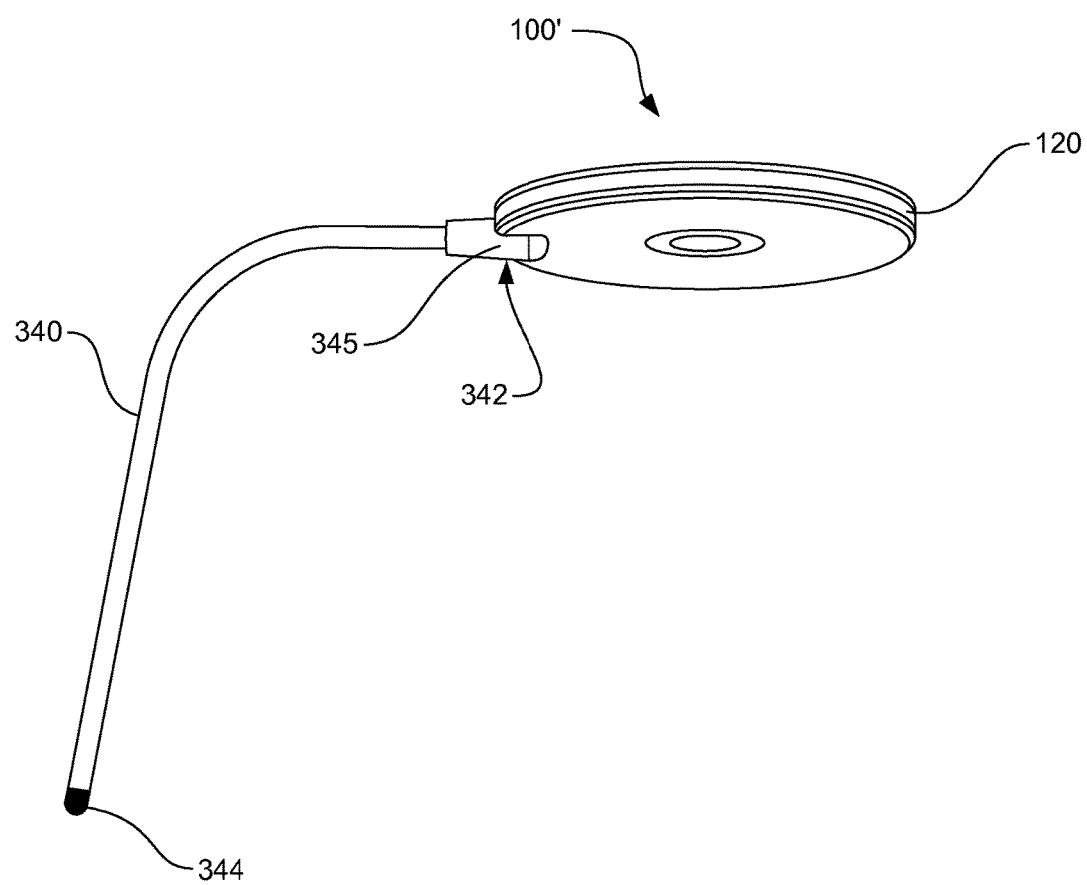
FIG. 7C shows a proximal end of the short extension lead of FIG. 7A attached to the perimeter edge of the IEAD housing, and includes the use of a strain gauge to help better secure the proximal end of the lead to its desired attachment location on the perimeter edge.

FIG. 7C shows a proximal end 342 of the short extension lead of FIG. 7A attached to the perimeter edge of the IEAD housing, and includes the use of a strain gauge 345 to help better secure the proximal end of the lead to its desired attachment location on the perimeter edge. When so attached, the proximal end of the short extension lead 340 is most easily attached to the ring electrode 120 that is located on the perimeter edge of the modified IEAD housing 100'. As needed, this ring electrode 120 may act as the cathode electrode, while the central electrode 110 (which is usually the cathode electrode) could, in this instance, be the anode electrode.

Figure 7D:
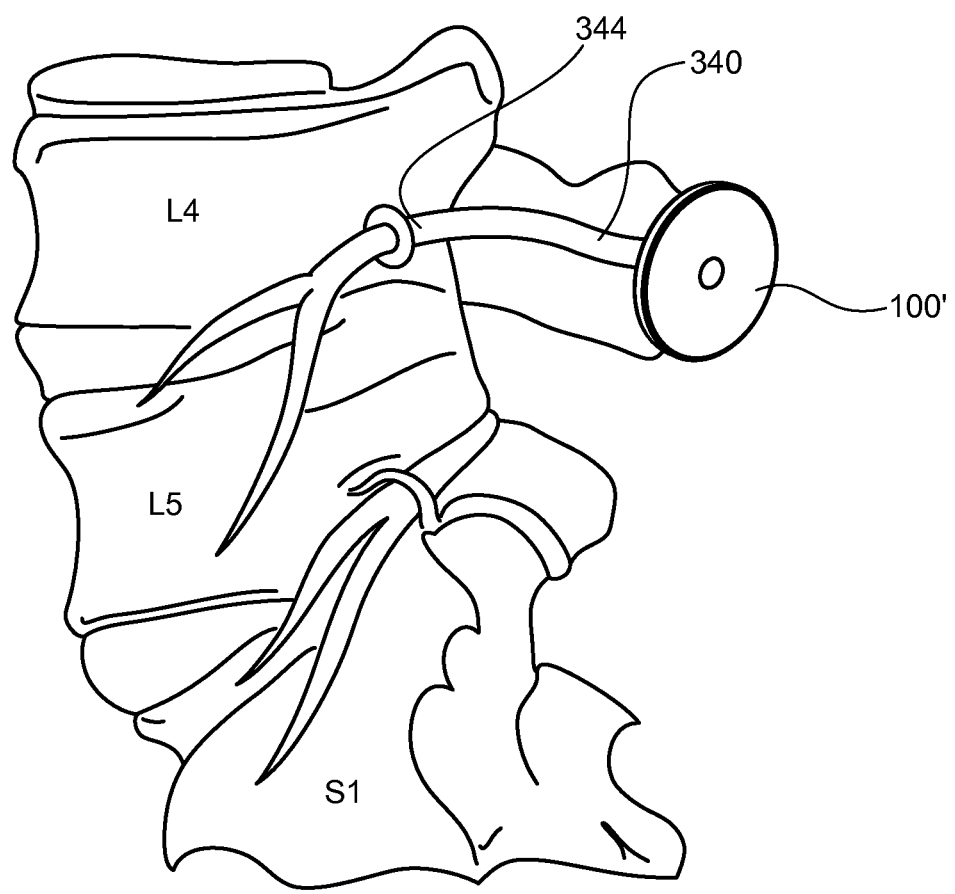
FIG. 7D schematically illustrates the IEAD of FIG. 7B or 7C positioned so as to place the cathode electrode closer to the lumbar nerve and dorsal roots while the IEAD housing remains subcutaneously positioned at a desired acupoint.

FIG. 7D schematically illustrates an exemplary use of the modified IEAD housing 100' of FIG. 7B or 7C positioned so as to place the cathode electrode, i.e., the distal end 344 of the catheter lead 340, closer to the lumbar nerve and dorsal roots while the IEAD housing 100' remains subcutaneously positioned at a desired acupoint, e.g., at acupoint BL22, BL23, BL24, BL25 or BL26. However, even though the IEAD 100' is positioned at the desired acupoint, the lead 340 provides an easily removed unipolar, smooth catheter that is routed so as to position its distal tip electrode 344 within a few millimeters of the lumbar nerve or dorsal root ganglion. This routing is chosen to avoid lead migration, and is accomplished using a relatively non-invasive injection method.

One way of accomplishing a non-invasive injection method is to use a split-able insertion catheter, similar to what is shown in U.S. Pat. No. 5,322,512 (used with epidural needles) or U.S. Pat. No. 4,411,654 (used with catheters). These two patents, U.S. Pat. No. 5,322,512 and U.S. Pat. No. 4,411,654 are incorporated herein by reference. Here, an introducer needle with a peel-able over lumen would be inserted down to be close to the lumbar nerve and/or dorsal root ganglion. The introducer would then be removed and the lead 340 from the IEAD 100 would then be passed down and through the remaining lumen. Once positioned, the sides of the lumen hub would be pulled apart to draw the lumen out of the tissue, leaving the lead 340 in place.

It should be noted that one of the advantages of using a modified IEAD housing 100' of the type shown in FIG. 7B, 7C or 7D is that the modification is achieved relatively simply and inexpensively starting with a leadless IEAD housing 100 of the type shown in FIG. 1. However, for those situations where the desired target tissue to be stimulated is not easily accessed by a leadless device, being able to add a short unipolar lead of the type described above in connection with FIGS. 7A through 7C adds more flexibility in the locations that can be effectively stimulated to treat lower back pain using an IEAD 100 or 100' as taught herein.

Figure 7E:
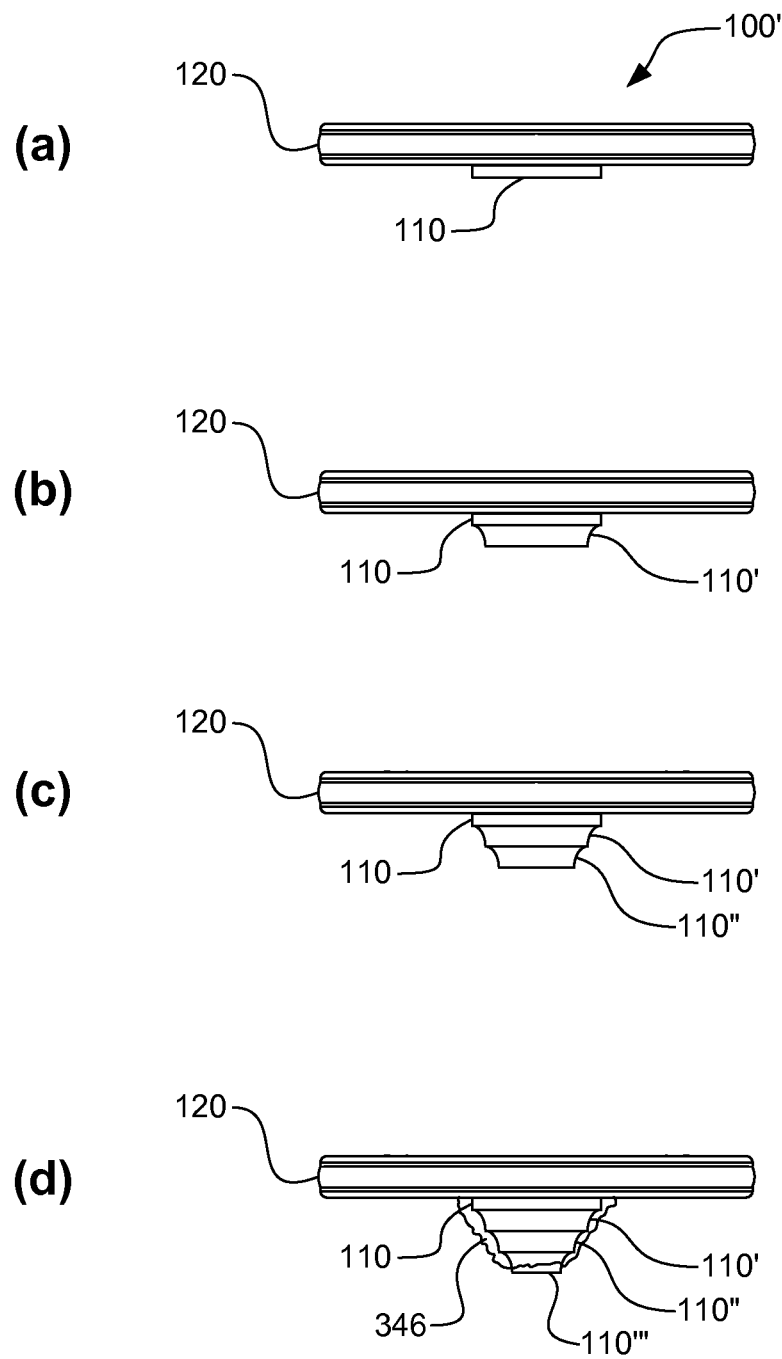
FIG. 7E includes a series of figures, (a), (b), (c) and (d), that show one process that may be used to "grow" or extend a short extension lead on the central cathode electrode on the IEAD housing using a deposition or equivalent process.

One possible way to create a very short extension catheter lead 340, or the equivalent of a very short catheter lead, is to extend or "grow" the existing catheter electrode 110 in small increments. Such process results in a stiff, or non-flexible lead, but a lead that can nonetheless be inserted into the tissue, like the point of a thumbtack, to place the electrode closer to the desired stimulation target. This process is illustrated in the series of sketches (a), (b), (c) and (d) shown in FIG. 7E. In FIG. 7E(a), a side view of the housing of the EA device 110' is shown, including a central cathode electrode 110 and an annular ring anode electrode 120. A suitable deposition process is then used to increase the height (or thickness) of the electrode 110, as shown in FIG. 7E(b). The additional height, or thickness, of the cathode electrode 110 is shown in FIG. 7E as 110'. This deposition process continues again, as shown in FIG. 7E(c), where the additional thickness is depicted as 110". The process may be repeated, as needed, until the desired extension length has been achieved, as depicted in FIG. 7E(d), where the additional thickness or length of the catheter lead 340 is shown as 110'''.

One deposition process that may be used to form the short catheter lead shown in FIG. 7E(d) is using what is commonly described and known as a 3-D "printing" process. Other suitable processes may, of course, also be used. Once the desired length of the catheter lead has been achieved, all but the distal tip 344 of the lead is covered with a suitable insulation material, such as an over-mold non-conductive material 346.

The extension or "growing" process associated with forming the catheter lead shown in FIG. 7E (a), (b), (c) and (d) is best used for very short catheter leads, e.g., leads having a length on the order of 5-10 mm.

It should also be noted that the use of implanted leaded devices to provide electrical stimulation to body tissue have existed for many, many years. Thus, there are numerous other ways and designs that could be used to provide a leaded device useable to treat lower back pain through electroacupuncture stimulation, as taught herein, at the specified lumbar nerve and dorsal roots near the acupoints BL22, BL23, BL24, BL25 or BL26. The present patent application is intended to cover such "other ways and designs" associated with a leaded device to the extent that all the other elements of the invention claimed herein, including limitations directed to electrical circuitry, battery impedance, stimulation regimen, stimulation location, and the like, are also present.

Exemplary Leaded Design

An exemplary design of a leaded device useable to treat lower back pain will next be described in connection with FIGS. 17A through 22C.

Figure 17A:
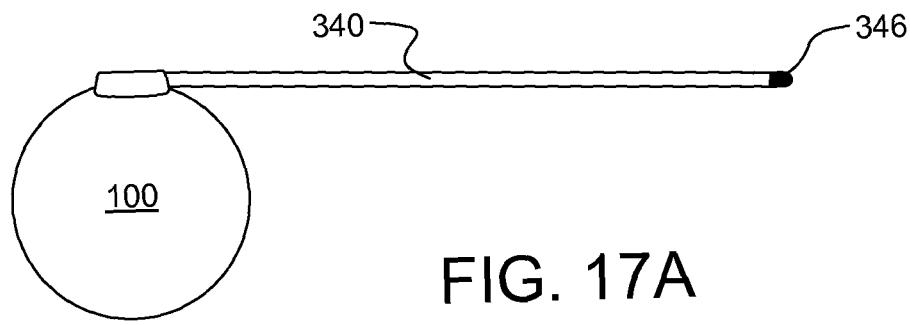
FIGS. 17A, 17B, and 17C respectively show three lead configurations that may be used with an IEAD in accordance with the teachings presented herein.
Figure 17B:
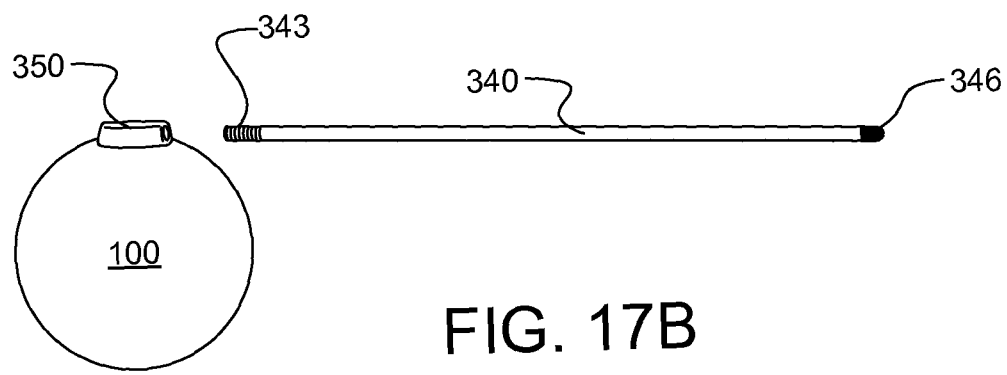
Figure 17C:
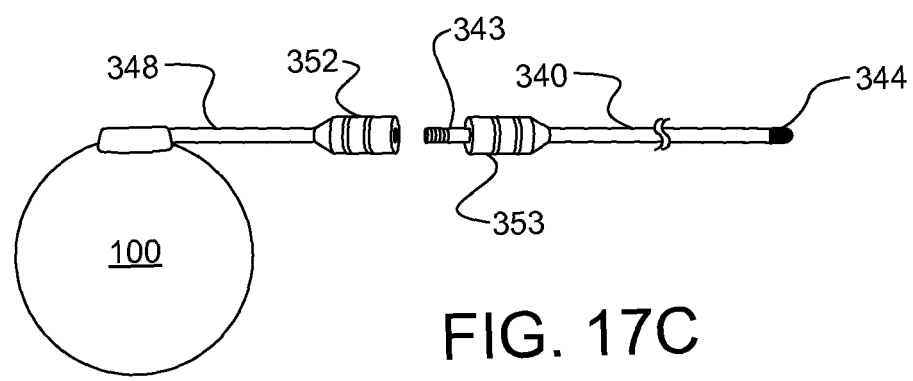

FIGS. 17A, 17B, and 17C respectively show three basic lead configurations that may be used with an IEAD in accordance with the teachings presented herein. A first lead configuration, shown in FIG. 17A, includes a flexible lead 340 permanently attached to a perimeter edge of an IEAD 100. The lead 340 has a unipolar electrode 346 located at its distal end. This first configuration is essentially the same as that which is shown and was previously described in connection with FIG. 7C.

A second lead configuration, shown in FIG. 17B, includes a flexible lead 340 detachably connected to a connector 350 located on a perimeter edge of an IEAD 100. The lead 340 has a conductive ring or sleeve 343 located at its proximal end. This proximal ring or sleeve 343 is electrically connected to the electrode 346 located at the distal end of the lead 340. The ring or sleeve 343 is adapted to be inserted and detachably secured (e.g., with a set screw) into the connector 350. When secured into the connector 350, the ring or sleeve 343 makes secure electrical connection with the radial feed through pin 130 (see FIGS. 4 and 4A), or more precisely with a wired connection between the tip of the feed through pin 130 and a receiving metal sleeve 158 (not visible in FIG. 17B) into which the ring or sleeve 343 resides when the proximal ring 343 is inserted the connector 350, thereby electrically connecting the radial feed through pin 130 with the distal electrode 346. Thus, use of the connector 350 allows the lead 340 to be selectively attached, or detached, from the IEAD 100 by selectively inserting, or removing, the proximal end of the lead 340 from the connector 350. This type of connection, which can be selectively attached or detached, is referred to as "detachably connecting", and a lead which can be thus selectively attached and detached is referred to as a "detachable" lead.

A third lead configuration, shown in FIG. 17C, includes a short pigtail lead 348 that has a wire therein having its proximal end permanently attached to the IEAD 100 (or, more precisely, to the radial feed though pin 130 that is connected to electrical circuitry within the IEAD 100) and its distal end terminated within a connector 352. The lead 340 includes a distal electrode 344 and a proximal ring 343 that are electrically connected to each other via a wire(s) inside of the lead 340. When the proximal end 343 of the lead 340 is inserted into the connector 352, an electrical connection is established between the proximal ring 343 and the conductive wire inside of the lead 340, thereby establishing electrical connection between the circuits within the IEAD 100 and the distal electrode 344. A suitable connector cover 353 may be used to help seal and hold closed the connection between the connector 352 and the proximal end 343 of the lead 340.

FIG. 18A shows an IEAD 100 that has a proximal end of a detachable lead 340 inserted into a connector built into a header assembly 352 mounted on a perimeter edge of the IEAD 100. The lead is relatively short, having a length that is typically no greater than about 50 mm, but in some instances could be as long as 100 mm.

FIG. 18B shows the embodiment shown in FIG. 18A, but with the detachable lead 340 being detached from the header assembly 352. As seen in FIG. 18B, the header assembly includes a septum 357 through which a set screw 358 may be selectively inserted, tightened or loosened. Such set screw is used to securely fasten or unfasten the proximal ring 343 of the lead 340 within the header assembly 352.

FIG. 18C shows a sectional side view taken along the line 18C-18C of the IEAD shown in FIG. 18B.

Figure 18D:
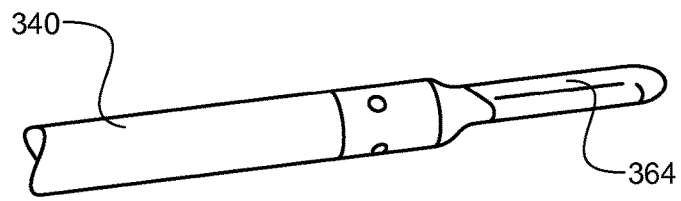
FIG. 18D shows a perspective view of the electrode at the distal end the detachable lead used in FIG. 18B.

FIG. 18D shows a perspective view of the electrode 346 at the distal end the detachable lead 340 used in FIGS. 18A and 18B. As seen in FIG. 18D, the distal electrode 346 has the general shape of a duckbill. This duckbill shape advantageously allows the electrode to be more easily positioned and secured at the desired stimulation sites near the lumbar nerve and dorsal roots.

Figure 19:
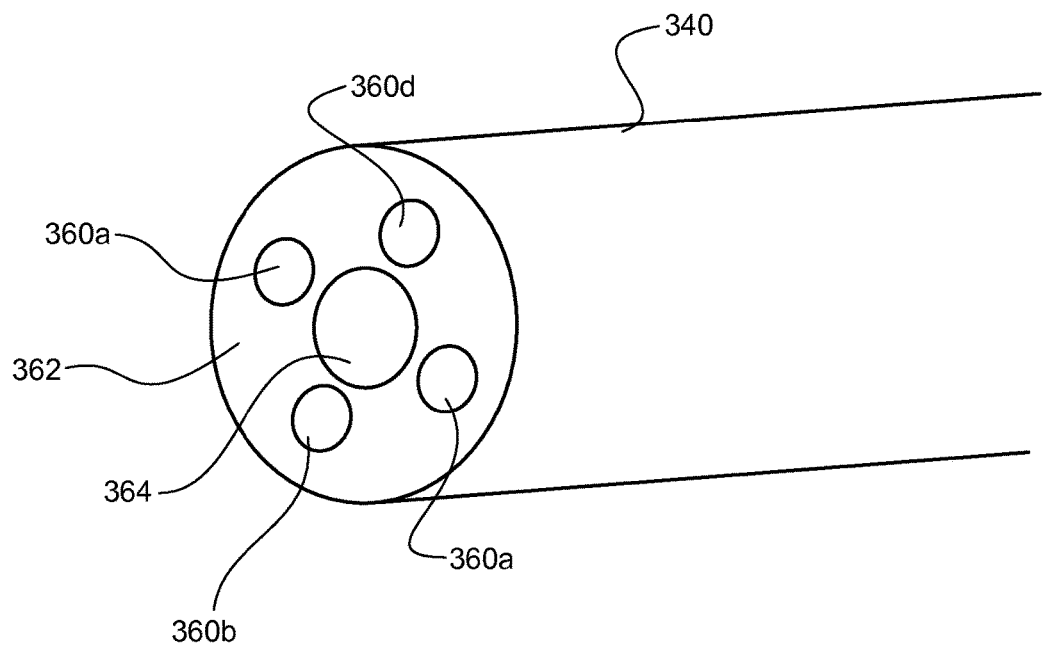
FIG. 19 illustrates a cross-sectional view of the detachable lead used in FIG. 18B.

FIG. 19 illustrates a cross-sectional view of the detachable lead 340 used, e.g., in FIGS. 18A and 18B. The exemplary lead 340 utilizes four conductive wires 360a, 360b, 360c and 360d. These four wires are embedded within a suitable insulative material 362, being more or less equi-distantly separated from each other. However, in operation, the four wires are electrically connected together so they function as a single conductor. A hole, tunnel or lumen 364 passes through almost the entire length of the lead 340 from the proximal end up to the location where the distal electrode 346 is located. This lumen 364 provides a pathway through which a semi-stiff stylet may be inserted, as needed, to help position the distal electrode 346 at its desired location.

Figure 20A:
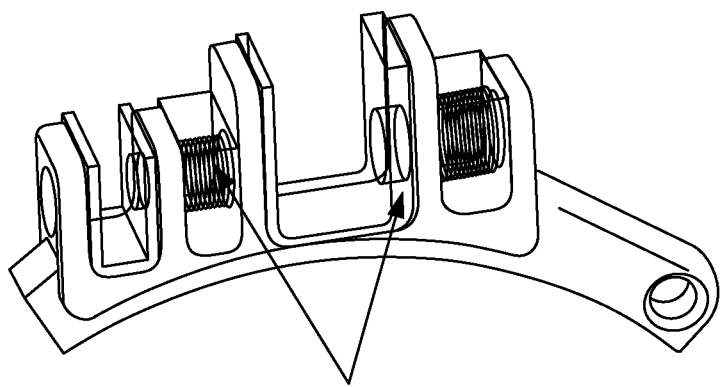
Figure 20B:
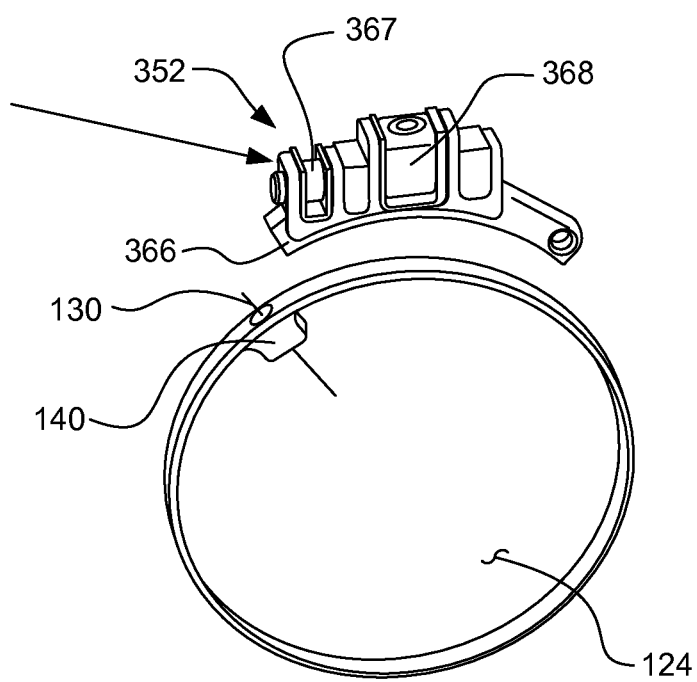
Figure 20C:
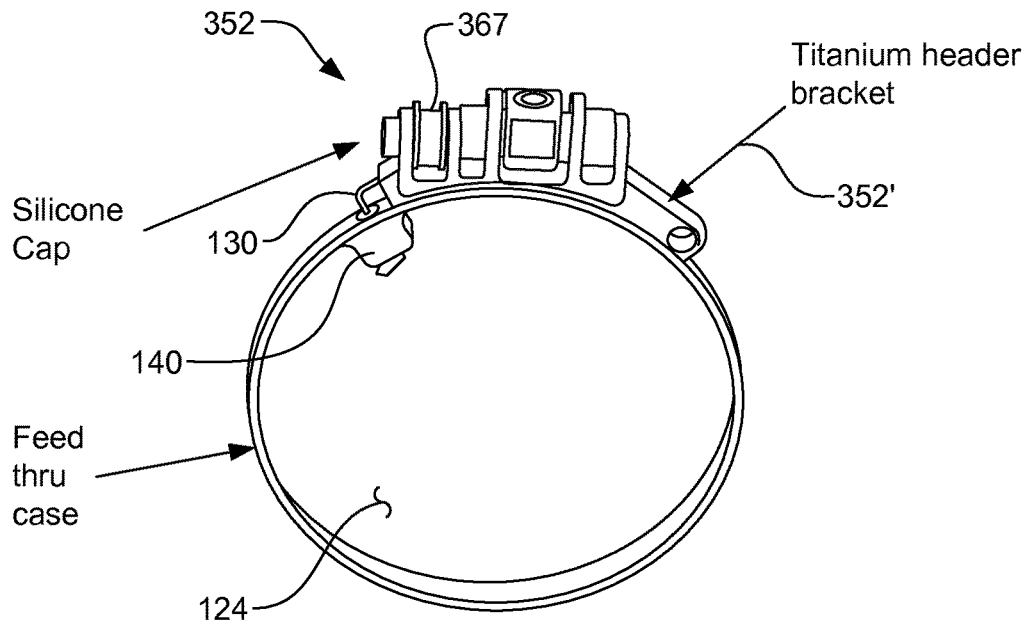

FIGS. 20A, 20B and 20C show a sequence of views associated with mounting the header assembly 352 to the perimeter edge of the case 124 of the IEAD 100. More particularly, FIG. 20A depicts the header assembly 352 prior to mounting it on the perimeter edge of the IEAD case 124. The header assembly is made principally from Titanium. It has a lumen 361 formed through its various elements that receive the proximal end of the lead 340. It also includes silicone insulation 363 and lumen seals 365 which are over-molded on the titanium header.

FIG. 20B illustrates the location on the perimeter edge of the IEAD case 124 where the header assembly 352 is mounted relative to the location of the radial feed-through pin 130. As shown and oriented in FIG. 20B, the feed through pin 130 is to the left of the left end 366 of the header assembly 352. The header assembly 352 shown in FIG. 20B also includes a Bal Seal 367 and a connector block 368.

FIG. 20C shows the header assembly after being mounted on the perimeter edge of the IEAD case 124. As seen in FIG. 20C, the feedthrough pin 130 is bent to connect with the header assembly 352, which (as indicated) is made primarily from a titantium bracket 352'. The attachment is realized by welding the header assembly onto the perimeter edge of the case 124.

Figure 21:
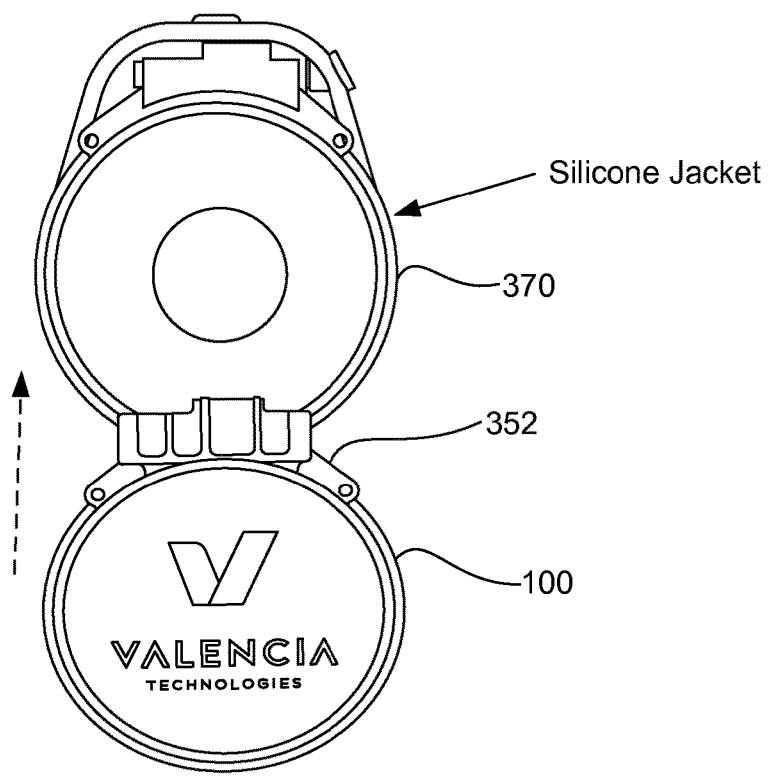
FIG. 21 illustrates the silicone jacket that is placed over the IEAD and header assembly once the header assembly has been mounted to the assembled IEAD case.

FIG. 21 illustrates a silicone jacket 370 that is placed over the IEAD 100 and header assembly 352 once the header assembly has been mounted (welded) to the assembled IEAD case 124.

Figure 22B:
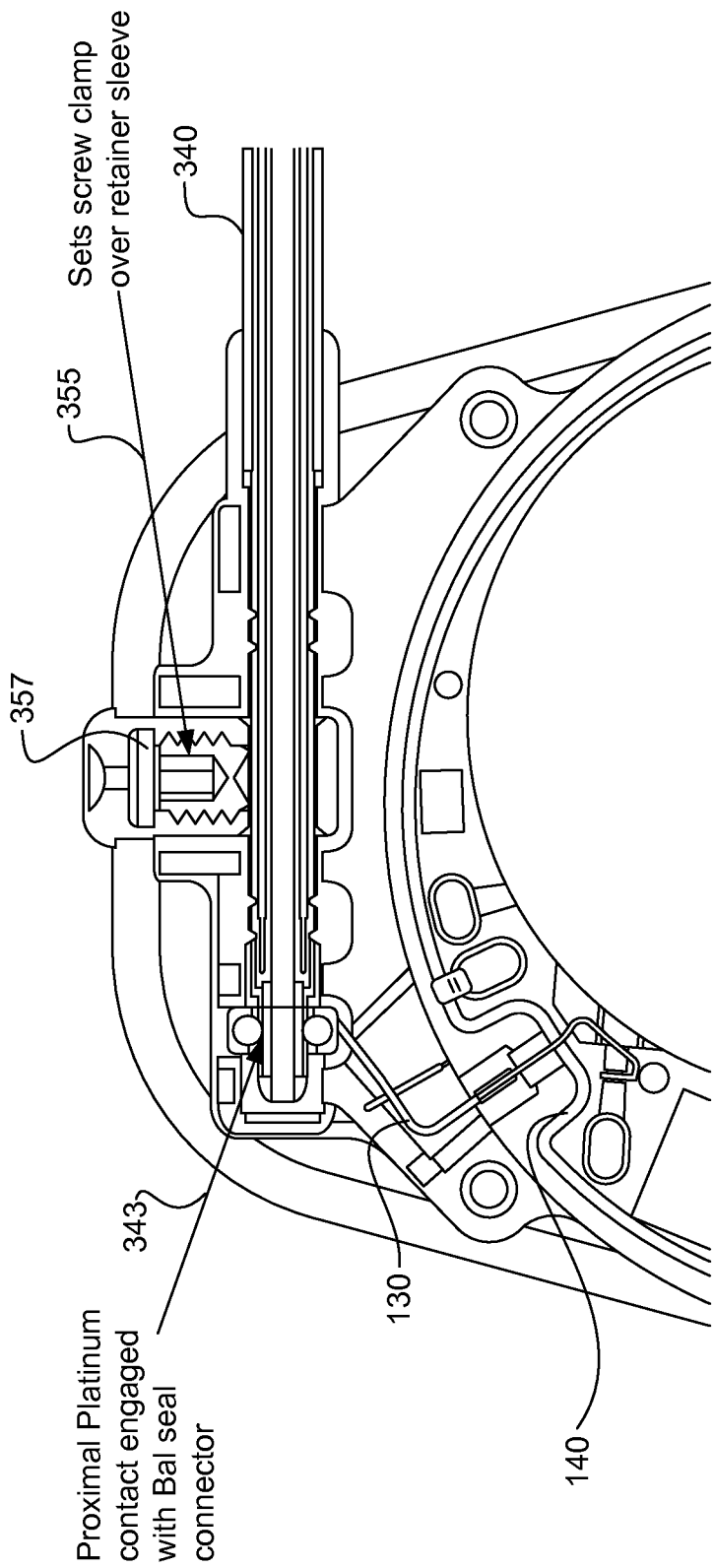

FIGS. 22A and 22B respectively illustrate sectional views of the header assembly mounted on the edge of the assembled IEAD when the proximal end of the detachable lead is not inserted into the header assembly (FIG. 22A) and when the proximal end of the detachable lead is inserted into the header assembly (FIG. 22B).

As seen in FIGS. 22A and 22B, details of the header assembly 352 are shown in sectional view. A Bal seal 367 includes a coiled wire 381 nested within a conductive ring or grove around the inside periphery of a hole of a doughnut-shaped conductive ring. The Bal seal 367 is further shown, in perspective view, in FIG. 22C. The distal tip of the feed through wire 130 is welded, or otherwise permanently bonded to, the case of the Bal seal 367. Thus, when the conductive proximal end 343 of a detachable lead is inserted into the header assembly, a secure electrical connection is realized between the feed through wire 130 and the conductive proximal end 343. The conductive proximal end 343 is, in turn, connected to the wires 360a, 360b, 360c and 360d (see FIG. 19) that pass through the body of the lead 340 to the conductive distal tip 346 of the lead.

Other details associated with the header assembly 352 are also shown in FIGS. 22A and 22B. For example, a titanium set screw 355, accessible for turning through a septum 357, allows the proximal end of the lead to be firmly secured within the header assembly, once inserted therein. This same set screw 355, of course, may be loosened should the need arise to detach the lead from the header assembly.

FIG. 22C shows a perspective view of a Bal Seal 367 used within the header assembly. The Bal Seal 367 includes coiled and flexible wires 381 inserted into an annular inner edge or grove (not visible in FIG. 22C) of the Bal Seal 367 that provide a secure electrical connection between the Bal Seal body and the conductive proximal end of a detachable lead, when inserted into the header assembly so that the proximal end passes through the Bal Seal coiled wires 381. A Bal Seal 367 of the type shown in FIG. 22C may be purchased commercially from several vendors.

Electrical Design

Next, with reference to FIGS. 8A-16, the electrical design and operation of the circuits employed within the IEAD 100 will be described, whether that IEAD is used as a leadless device (i.e., the IEAD 100 shown in FIG. 1) or a leaded device (i.e., the IEAD 100' shown in FIGS. 7B and 7C). More details associated with the design of the electrical circuits described herein may be found in Applicant's earlier application, application Ser. No. 13/598,582, filed Aug. 29, 2012. Also, additional details regarding the electrical design and operation may be gleaned from Applicant's co-pending patent application, "Circuits and Methods for Using a High Impedance, Thin, Coin-cell Type Battery in an Implantable Electroacupuncture Device," application Ser. No. 13/769, 699, filed Feb. 18, 2013, which application is incorporated herein by reference.

Figure 8A:
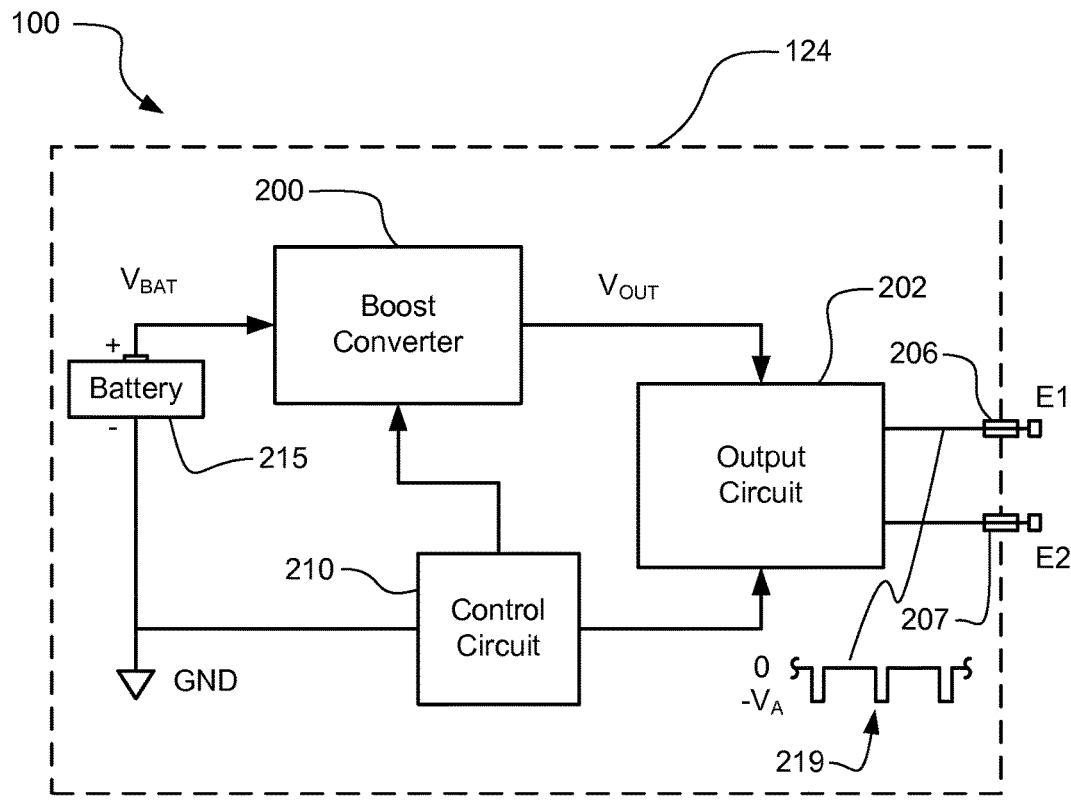
FIG. 8A illustrates a functional block diagram of the electronic circuits used within an IEAD of the type described herein.

FIG. 8A shows a functional block diagram of an IEAD 100 made in accordance with the teachings disclosed herein. As seen in FIG. 8A, the IEAD 100 uses an implantable battery 215 having a battery voltage $V_{BAT}$. Also included within the IEAD 100 is a Boost Converter circuit 200, an Output Circuit 202 and a Control Circuit 210. The battery 115, boost converter circuit 200, output circuit 202 and control circuit 210 are all housed within an hermetically sealed housing 124.

As controlled by the control circuit 210, the output circuit 202 of the IEAD 100 generates a sequence of stimulation pulses that are delivered to electrodes E1 and E2, through feed-through terminals 206 and 207, respectively, in accordance with a prescribed stimulation regimen. A coupling capacitor $C_C$ is also employed in series with at least one of the feed-through terminals 206 or 207 to prevent DC (direct current) current from flowing into the patient's body tissue.

As explained more fully below in connection with the description of FIGS. 15A and 15B, and as can also be seen from the waveform 219 shown in the lower right corner of FIG. 8A, the prescribed stimulation regimen typically comprises a continuous stream of stimulation pulses having a fixed amplitude, e.g., $V_A$ volts, a fixed pulse width, e.g., 0.5 millisecond, and at a fixed frequency, e.g., 2 Hz, during each stimulation session. The stimulation session, also as part of the stimulation regimen, is generated at a very low duty cycle, e.g., for 30 minutes once each week. Other stimulation regimens may also be used, e.g., using a variable frequency for the stimulus pulse during a stimulation session rather than a fixed frequency. Also, the rate of occurrence of the stimulation session may be varied from as short as, e.g., 1 day, to as long as, e.g., 14 days.

The electrodes E1 and E2 form an integral part of the housing 124. That is, electrode E2 may comprise a circumferential anode electrode that surrounds a cathode electrode E1. The cathode electrode E1, for the embodiment described here, is electrically connected to the case 124 (thereby making the feed-through terminal 206 unnecessary).

In a second exemplary embodiment, particularly well-suited for implantable electrical stimulation devices, the anode electrode E2 is electrically connected to the case 124 (thereby making the feed-through terminal 207 unnecessary). The cathode electrode E1 is electrically connected to the circumferential electrode that surrounds the anode electrode E2. That is, the stimulation pulses delivered to the target tissue location (i.e., to the selected acupoint) through the electrodes E1 and E2 are, relative to a zero volt ground (GND) reference, negative stimulation pulses, as shown in the waveform diagram near the lower right hand corner of FIG. 8A.

Thus, in the embodiment described in FIG. 8A, it is seen that during a stimulation pulse the electrode E2 functions as an anode, or positive (+) electrode, and the electrode E1 functions as a cathode, or negative (−) electrode.

The battery 115 provides all of the operating power needed by the EA device 100. The battery voltage $V_{BAT}$ is not the optimum voltage needed by the circuits of the EA device, including the output circuitry, in order to efficiently generate stimulation pulses of amplitude, e.g., $-V_A$ volts. The amplitude $V_A$ of the stimulation pulses is typically many times greater than the battery voltage $V_{BAT}$. This means that the battery voltage must be "boosted", or increased, in order for stimulation pulses of amplitude $V_A$ to be generated. Such "boosting" is done using the boost converter circuit 200. That is, it is the function of the Boost Converter circuit 200 to take its input voltage, $V_{BAT}$, and convert it to another voltage, e.g., $V_{OUT}$, which voltage $V_{OUT}$ is needed by the output circuit 202 in order for the IEAD 100 to perform its intended function.

The leadless IEAD 100 shown in FIG. 8A, and packaged as described above in connection with FIGS. 1-7, advantageously provides a tiny self-contained, coin-sized stimulator that may be implanted in a patient at or near a specified acupoint in order to favorably treat a condition or disease of a patient. Moreover, the leaded IEAD, as packaged and described above in connection with FIGS. 7A-7D and/or FIGS. 17A-22C,—which leaded IEAD is realized by making only modest changes to the packaging of the leadless IEAD—also provides a tiny self-contained, coin-sized stimulator that may be implanted near a desired target stimulation site, but wherein the actual stimulation site may be selected more precisely by positioning the distal tip of the detachable lead 340 right next to, or even touching, the target stimulation site. Regardless of whether the leaded or leadless configuration in employed, the coin-sized stimulator advantageously applies electrical stimulation pulses at very low levels and low duty cycles in accordance with specified stimulation regimens through electrodes that form an integral part of the housing of the stimulator. A tiny battery inside of the coin-sized stimulator provides enough energy for the stimulator to carry out its specified stimulation regimen over a period of several years. Thus, the coin-sized stimulator, once implanted, provides an unobtrusive, needleless, long-lasting, safe, elegant and effective mechanism for treating certain conditions and diseases that have long been treated by acupuncture or electroacupuncture.

Figure 8B:
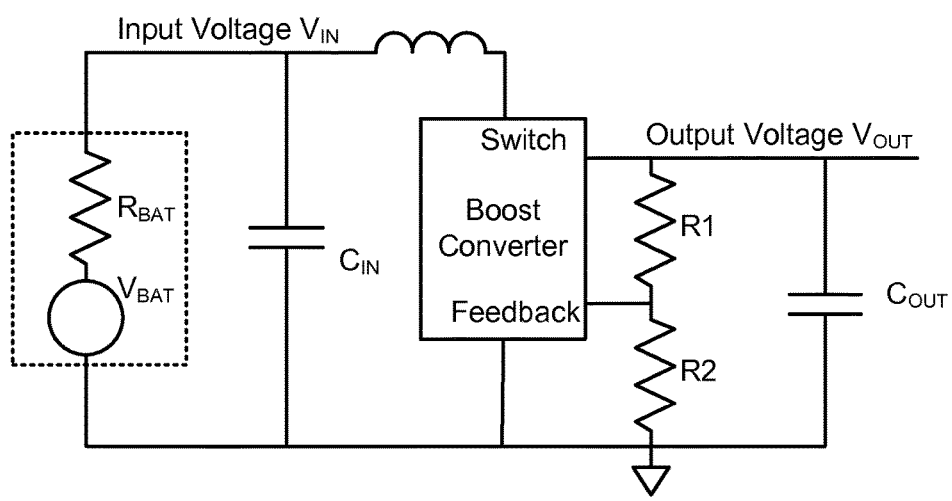
FIG. 8B shows a basic boost converter circuit configuration, and is used to model how the impedance of the battery $R_{BAT}$ can affect its performance.

A boost converter integrated circuit (IC) typically draws current from its power source in a manner that is proportional to the difference between the actual output voltage $V_{OUT}$ and a set point output voltage, or feedback signal. A representative boost converter circuit that operates in this manner is shown in FIG. 8B. At boost converter start up, when the actual output voltage is low compared to the set point output voltage, the current drawn from the power source can be quite large. Unfortunately, when batteries are used as power sources, they have internal voltage losses (caused by the battery's internal impedance) that are proportional to the current drawn from them. This can result in under voltage conditions when there is a large current demand from the boost converter at start up or at high instantaneous output current. Current surges and the associated under voltage conditions can lead to undesired behavior and reduced operating life of an implanted electroacupuncture device.

In the boost converter circuit example shown in FIG. 8A, the battery is modeled as a voltage source with a simple series resistance. With reference to the circuit shown in FIG. 8A, when the series resistance $R_{BAT}$ is small (5 Ohms or less), the boost converter input voltage $V_{IN}$, output voltage $V_{OUT}$ and current drawn from the battery, $I_{BAT}$, typically look like the waveform shown in FIG. 9A, where the horizontal axis is time, and the vertical axis on the left is voltage, and the vertical axis of the right is current.

Figure 9A:
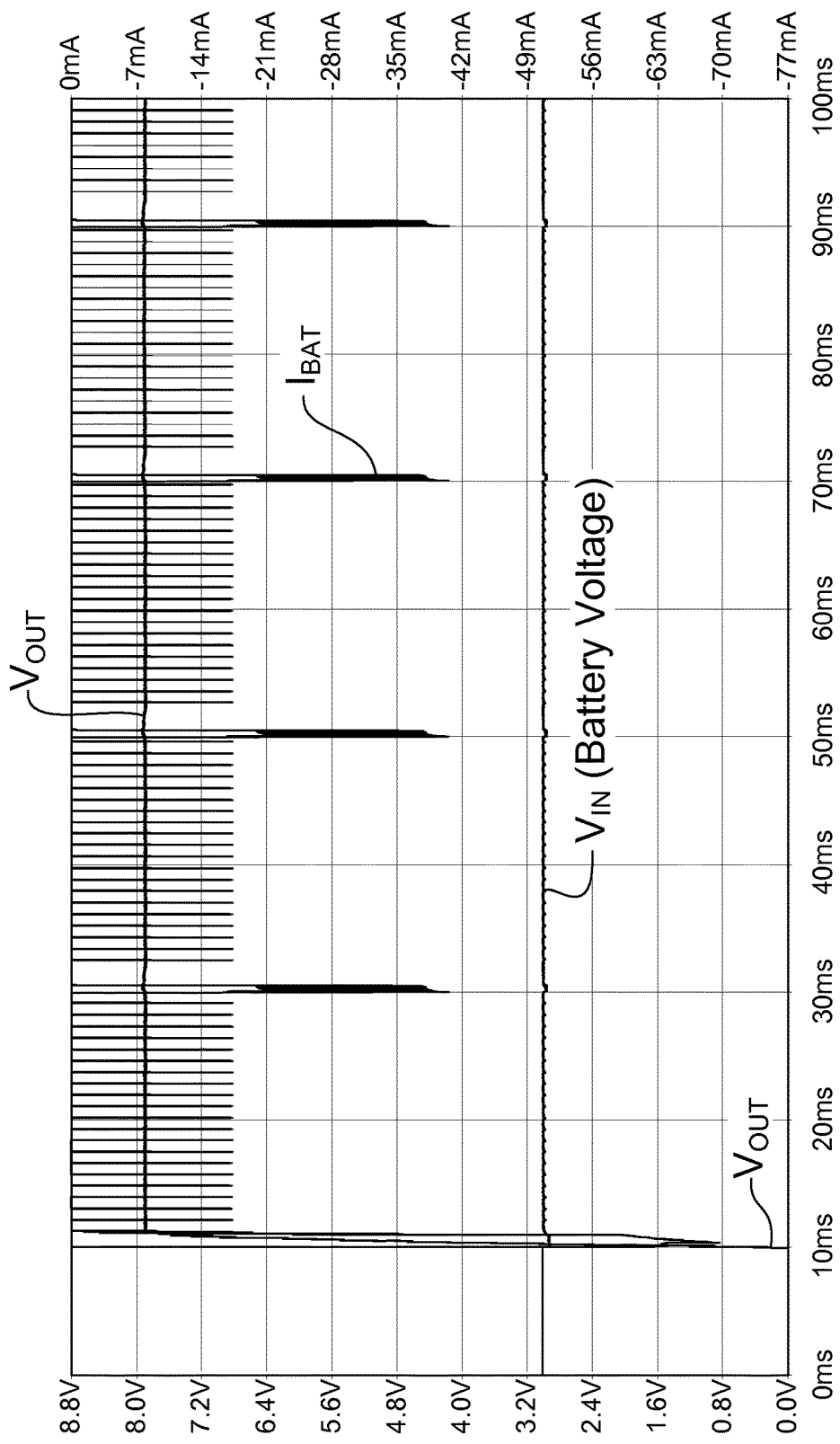
FIG. 9A illustrates a typical voltage and current waveform for the circuit of FIG. 8 when the battery impedance $R_{BAT}$ is small.

Referring to the waveform in FIG. 9A, at boost converter startup (10 ms), there is 70 mA of current drawn from the battery with only ~70 mV of drop in the input voltage $V_{IN}$. Similarly, the instantaneous output current demand for electro-acupuncture pulses draws up to 40 mA from the battery with an input voltage drop of ~40 mV.

Figure 9B:
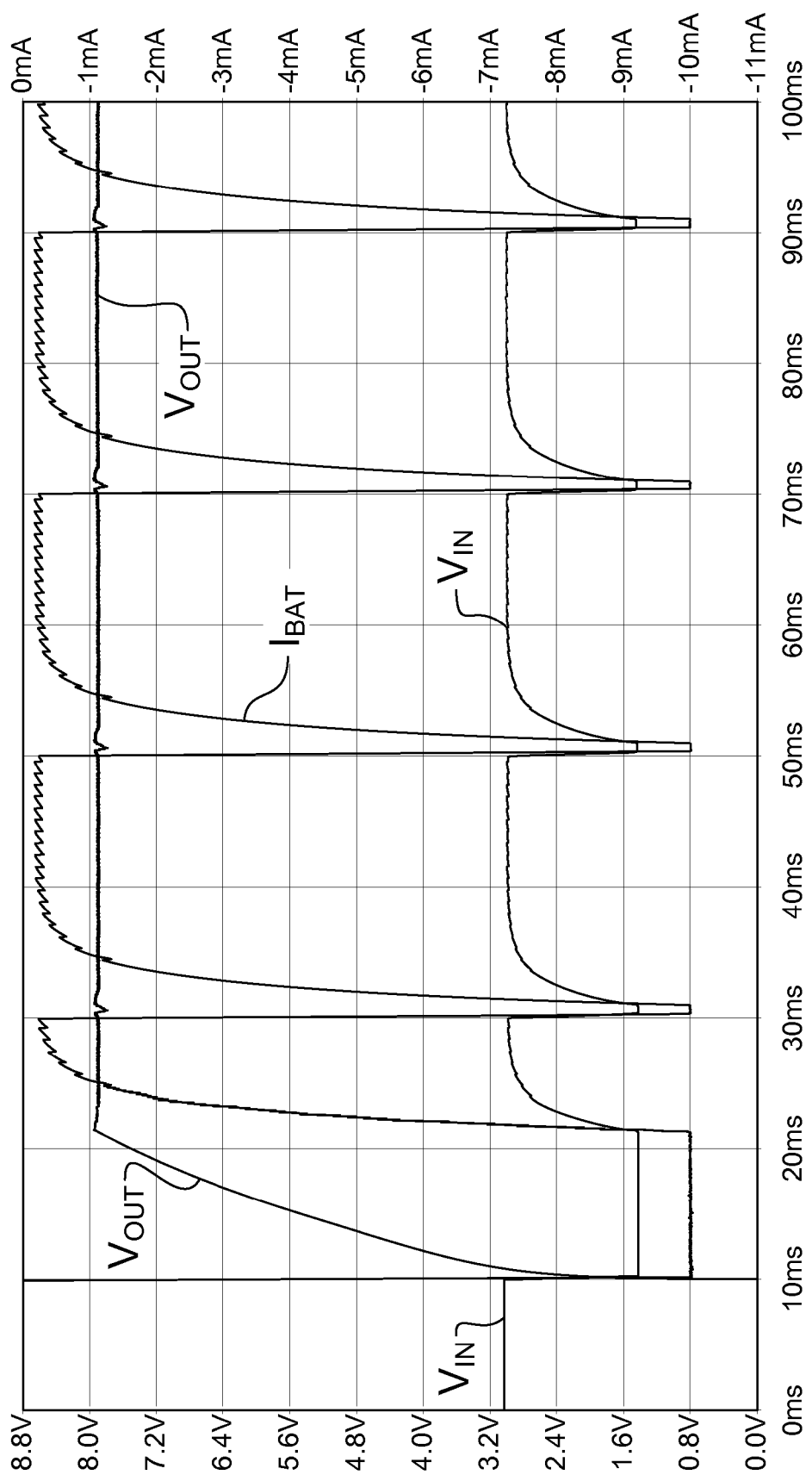
FIG. 9B shows the voltage and current waveform for the circuit of FIG. 8B when the battery impedance $R_{BAT}$ is large.

Disadvantageously, however, a battery with higher internal impedance (e.g., 160 Ohms), cannot source more than a milliampere or so of current without a significant drop in output voltage. This problem is depicted in the timing waveform diagram shown in FIG. 9B. In FIG. 9B, as in FIG. 9A, the horizontal axis is time, the left vertical axis is voltage, and the right vertical axis is current.

As seen in FIG. 9B, as a result of the higher internal battery impedance, the voltage at the battery terminal ($V_{IN}$) is pulled down from 2.9 V to the minimum input voltage of the boost converter (~1.5 V) during startup and during the instantaneous output current load associated with electro-acupuncture stimulus pulses. The resulting drops in output voltage $V_{OUT}$ are not acceptable in any type of circuit except an uncontrolled oscillator circuit.

Also, it should be noted that although the battery used in the boost converter circuit is modeled in FIG. 8B as a simple series resistor, battery impedance can arise from the internal design, battery electrode surface area and different types of electrochemical reactions. All of these contributors to battery impedance can cause the voltage of the battery at the battery terminals to decrease as the current drawn from the battery increases.

In a suitably small and thin implantable electroacupuncture device (IEAD) of the type disclosed herein, it is desired to use a higher impedance battery in order to assure a small and thin device, keep costs low, and/or to have low self-discharge rates. The battery internal impedance also typically increases as the battery discharges. This can limit the service life of the device even if a new battery has acceptably low internal impedance. Thus, it is seen that for the IEAD 100 disclosed herein to reliably perform its intended function over a long period of time, a circuit design is needed for the boost converter circuit that can manage the instantaneous current drawn from $V_{IN}$ of the battery. Such current management is needed to prevent the battery's internal impedance from causing $V_{IN}$ to drop to unacceptably low levels as the boost converter circuit pumps up the output voltage $V_{OUT}$ and when there is high instantaneous output current demand, as occurs when EA stimulation pulses are generated.

Figure 10:
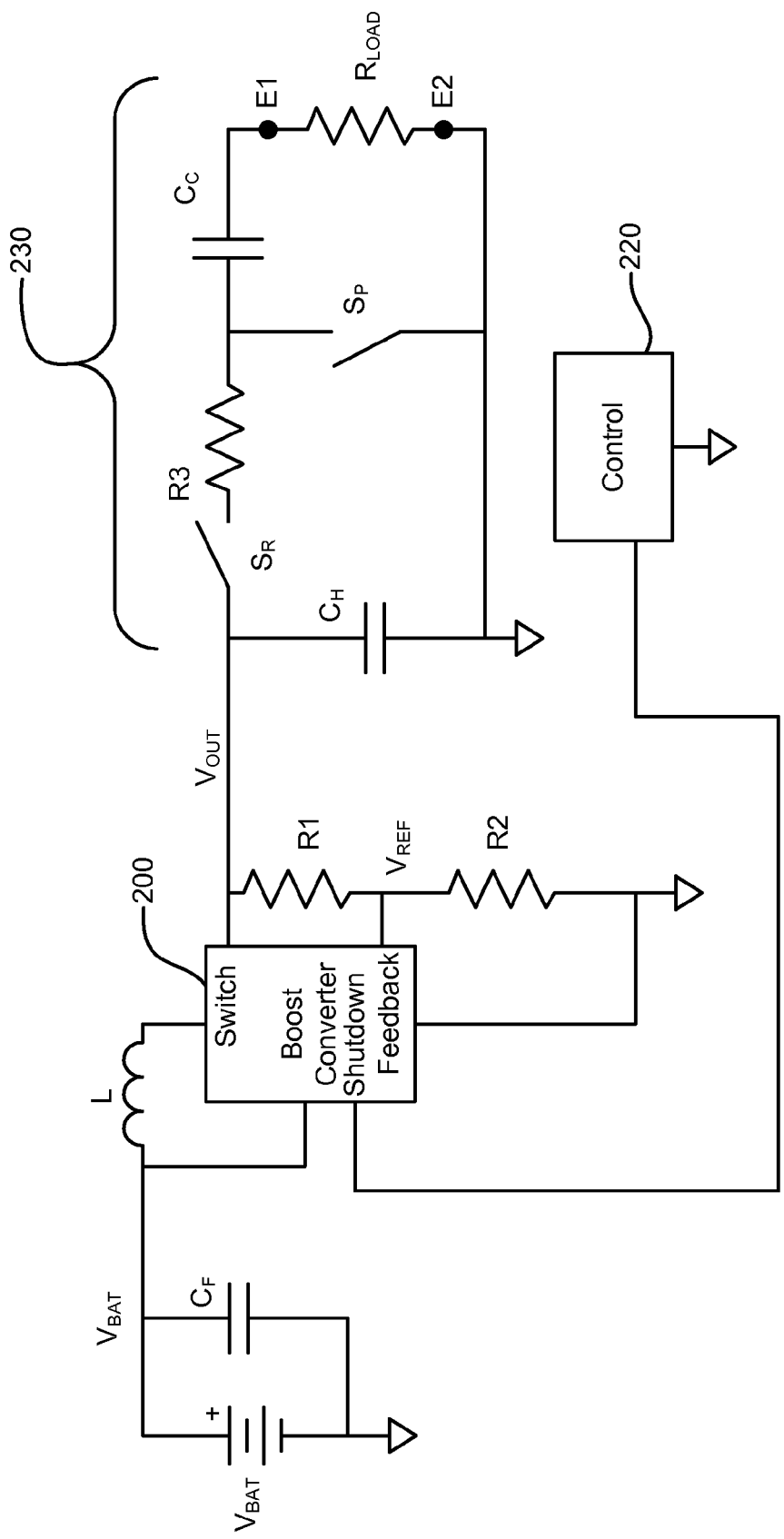
FIG. 10 shows an exemplary boost converter circuit and a functional pulse generation circuit configuration for use within the IEAD.

To provide this needed current management, the IEAD 100 disclosed herein employs electronic circuitry as shown in FIG. 10, or equivalents thereof. Similar to what is shown in FIG. 8B, the circuitry of FIG. 10 includes a battery, a boost converter circuit 200, an output circuit 230, and a control circuit 220. The control circuit 220 generates a digital control signal that is used to duty cycle the boost converter circuit 200 ON and OFF in order to limit the instantaneous current drawn from the battery. That is, the digital control signal pulses the boost converter ON for a short time, but then shuts the boost converter down before a significant current can be drawn from the battery. In conjunction with such pulsing, an input capacitance $C_F$ is used to reduce the ripple in the input voltage $V_{IN}$. The capacitor $C_F$ supplies the high instantaneous current for the short time that the boost converter is ON and then recharges more slowly from the battery during the interval that the boost converter is OFF.

In the circuitry shown in FIG. 10, it is noted that the output voltage $V_{OUT}$ generated by the boost converter circuit 200 is set by the reference voltage $V_{REF}$ applied to the set point or feedback terminal of the boost converter circuit 200. For the configuration shown in FIG. 10, $V_{REF}$ is proportional to the output voltage $V_{OUT}$, as determined by the resistor dividing network of R1 and R2.

The switches $S_P$ and $S_R$, shown in FIG. 10 as part of the output circuit 230, are also controlled by the control circuit 220. These switches are selectively closed and opened to form the EA stimulation pulses applied to the load, $R_{LOAD}$.

Before a stimulus pulse occurs, switch $S_R$ is closed sufficiently long for the circuit side of coupling capacitor $C_C$ to be charged to the output voltage, $V_{OUT}$. The tissue side of Cc is maintained at 0 volts by the cathode electrode E2, which is maintained at ground reference. Then, for most of the time between stimulation pulses, both switches $S_R$ and $S_P$ are kept open, with a voltage approximately equal to the output voltage $V_{OUT}$ appearing across the coupling capacitor $C_C$.

At the leading edge of a stimulus pulse, the switch $S_P$ is closed, which immediately causes a negative voltage $-V_{OUT}$ to appear across the load, $R_{LOAD}$, causing the voltage at the anode E1 to also drop to approximately $-V_{OUT}$, thereby creating the leading edge of the stimulus pulse. This voltage starts to decay back to 0 volts as controlled by an RC (resistor-capacitance) time constant that is long compared with the desired pulse width. At the trailing edge of the pulse, before the voltage at the anode E1 has decayed very much, the switch $S_P$ is open and the switch $S_R$ is closed. This action causes the voltage at the anode E1 to immediately (relatively speaking) return to 0 volts, thereby defining the trailing edge of the pulse. With the switch $S_R$ closed, the charge on the circuit side of the coupling capacitor $C_C$ is allowed to charge back to $V_{OUT}$ within a time period controlled by a time constant set by the values of capacitor $C_C$ and resistor R3. When the circuit side of the coupling capacitor $C_C$ has been charged back to $V_{OUT}$, then switch $S_R$ is opened, and both switches $S_R$ and $S_P$ remain open until the next stimulus pulse is to be generated. Then the process repeats each time a stimulus pulse is to be applied across the load.

Thus, it is seen that in one embodiment of the electronic circuitry used within the IEAD 100, as shown in FIG. 10, a boost converter circuit 200 is employed which can be shut down with a control signal. The control signal is ideally a digital control signal generated by a control circuit 220 (which may be realized using a microprocessor or equivalent circuit). The control signal is applied to the low side (ground side) of the boost converter circuit 200 (identified as the "shutdown" terminal in FIG. 10). A capacitor $C_F$ supplies instantaneous current for the short ON time that the control signal enables the boost converter circuit to operate. And, the capacitor CF is recharged from the battery during the relatively long OFF time when the control signal disables the boost converter circuit.

Figure 11:
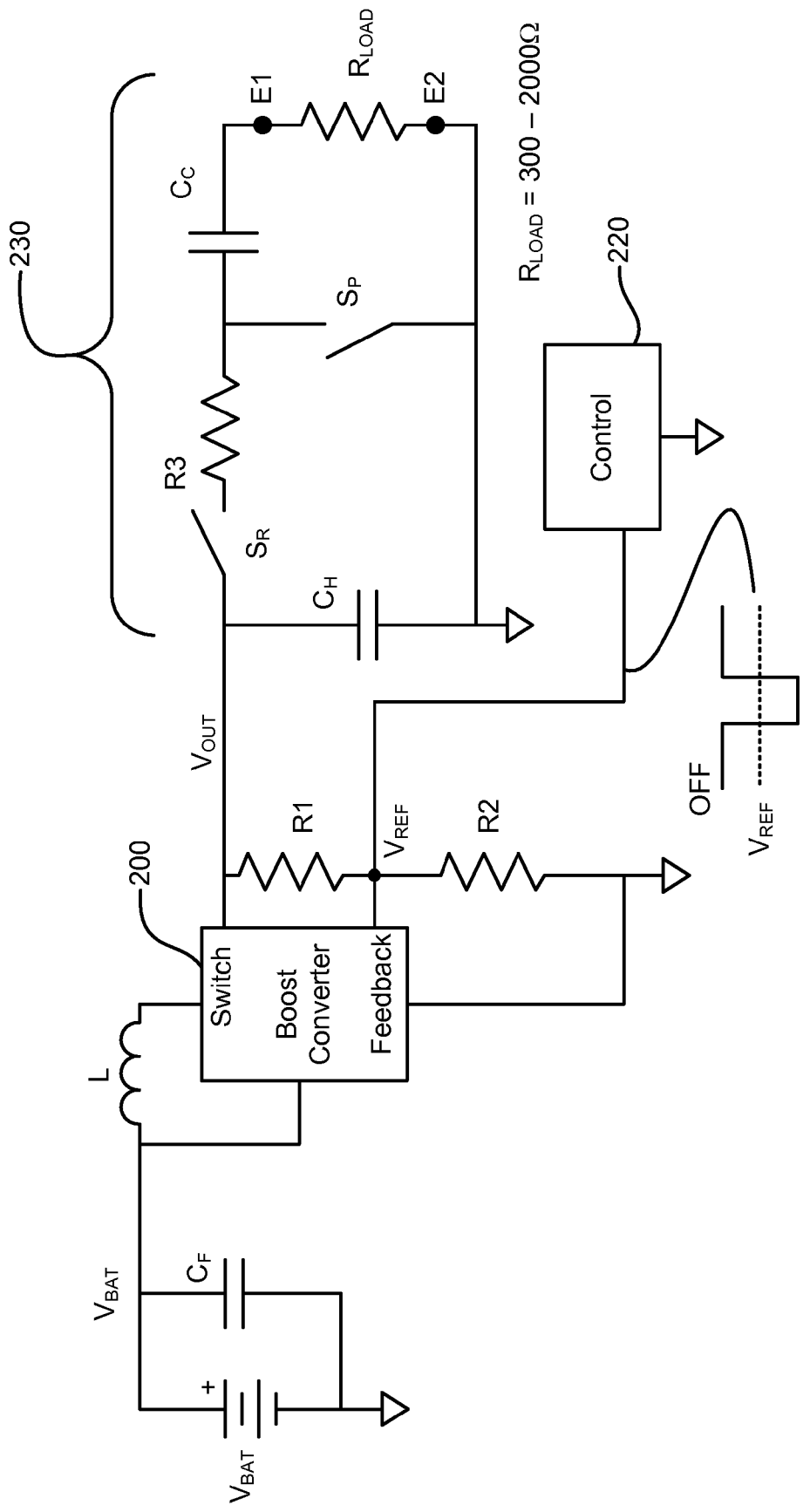
FIG. 11 shows an alternate boost converter circuit configuration and a functional pulse generation circuit for use within the IEAD.

An alternate embodiment of the electronic circuitry that may be used within the IEAD 100 is shown in FIG. 11. This circuit is in most respects the same as the circuitry shown in FIG. 10. However, in this alternate embodiment shown in FIG. 11, the boost converter circuit 200 does not have a specific shut down input control. Rather, as seen in FIG. 11, the boost converter circuit is shut down by applying a control voltage to the feedback input of the boost converter circuit 200 that is higher than $V_{REF}$. When this happens, i.e., when the control voltage applied to the feedback input is greater than $V_{REF}$, the boost converter will stop switching and draws little or no current from the battery. The value of $V_{REF}$ is typically a low enough voltage, such as a 1.2 V band-gap voltage, that a low level digital control signal can be used to disable the boost converter circuit. To enable the boost converter circuit, the control signal can be set to go to a high impedance, which effectively returns the node at the $V_{REF}$ terminal to the voltage set by the resistor divider network formed from R1 and R2. Alternatively the control signal can be set to go to a voltage less than $V_{REF}$.

A low level digital control signal that performs this function of enabling (turning ON) or disabling (turning OFF) the boost converter circuit is depicted in FIG. 11 as being generated at the output of a control circuit 220. The signal line on which this control signal is present connects the output of the control circuit 220 with the $V_{REF}$ node connected to the feedback input of the boost converter circuit. This control signal, as suggested by the waveform shown in FIG. 11, varies from a voltage greater than $V_{REF}$, thereby disabling or turning OFF the boost converter circuit, to a voltage less than $V_{REF}$, thereby enabling or turning the boost converter circuit ON.

Figure 12:
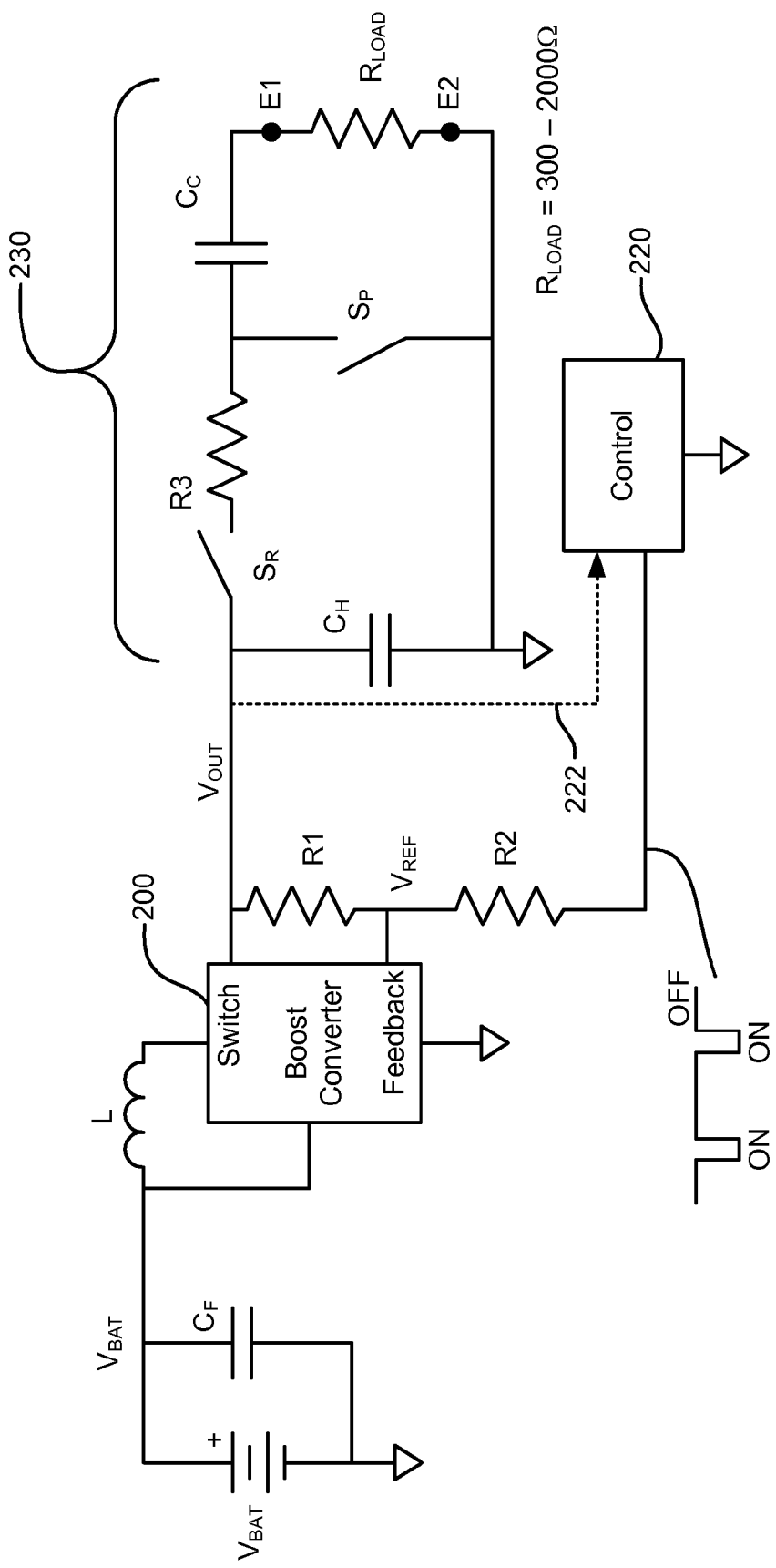
FIG. 12 shows a refinement of the circuit configuration of FIG. 11.

A refinement to the alternate embodiment shown in FIG. 11 is to use the control signal to drive the low side of R2 as shown in FIG. 12. That is, as shown in FIG. 12, the boost converter circuit 200 is shut down when the control signal is greater than $V_{REF}$ and runs when the control signal is less than $V_{REF}$. A digital control signal can be used to perform this function by switching between ground and a voltage greater than $V_{REF}$. This has the additional possibility of delta-sigma modulation control of $V_{OUT}$ if a measurement of the actual $V_{OUT}$ is available for feedback, e.g., using a signal line 222, to the controller.

Figure 13A:
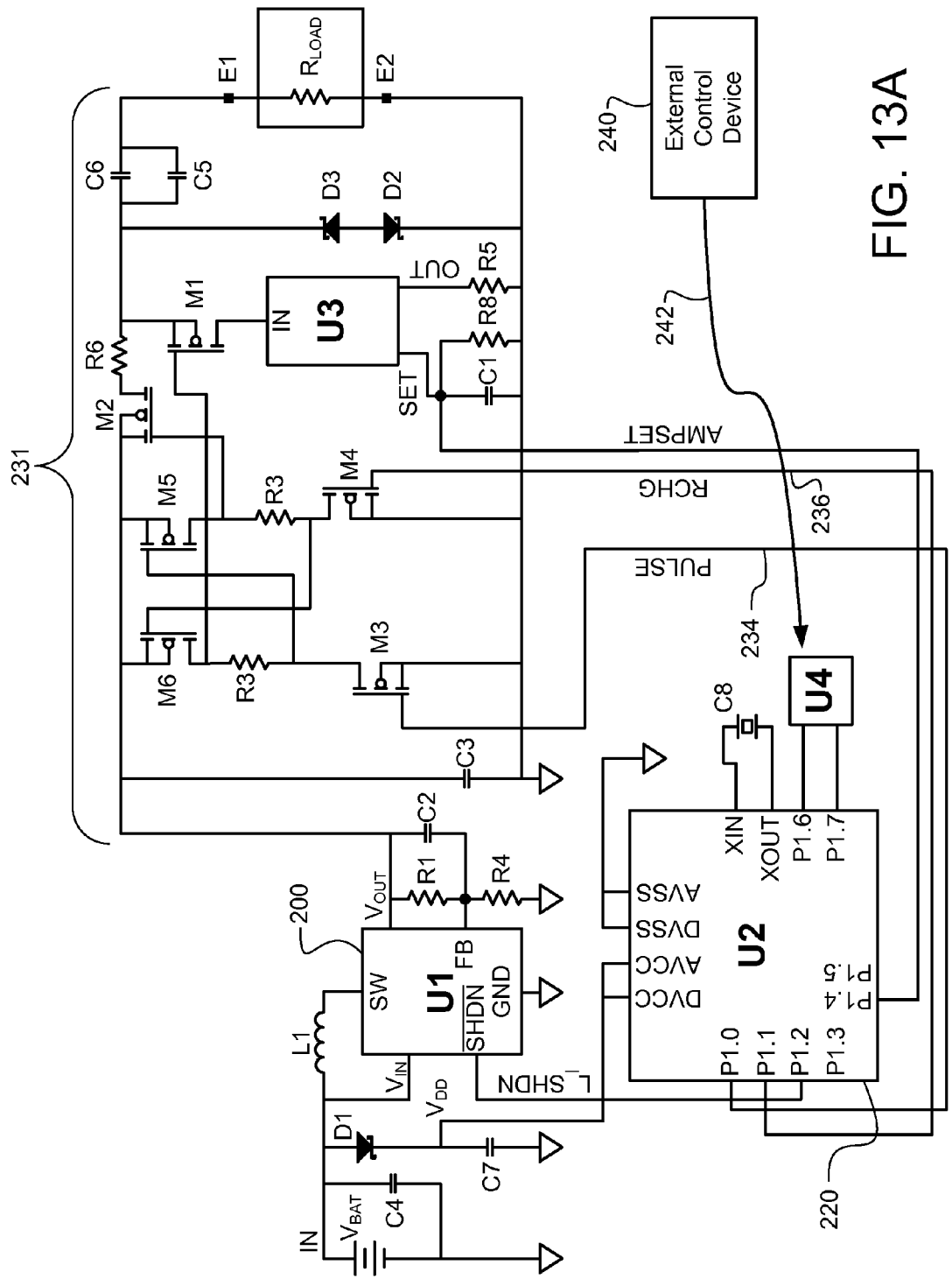
FIG. 13A shows an exemplary schematic configuration for an implantable electroacupuncture device (IEAD) that utilizes the boost converter configuration shown in FIG. 10.

One exemplary embodiment of the circuitry used in an implantable electroacupuncture device (IEAD) 100 that employs a digital control signal as taught herein is shown in the schematic diagram shown in FIG. 13A. In FIG. 13A, there are basically four integrated circuits (ICs) used as the main components. The IC U1 is a boost converter circuit, and performs the function of the boost converter circuit 200 described previously in connection with FIGS. 8B, 10, 11 and 12.

The IC U2 is a micro-controller IC and is used to perform the function of the control circuit 220 described previously in connection with FIGS. 10, 11 and 12. An exemplary IC for this purpose is a MSP430G24521 micro-controller chip made by Texas Instruments. This chip includes 8 KB of Flash memory. Having some memory included with the micro-controller may allow the parameters associated with a selected stimulation regimen to be defined and stored. One of the advantages of the IEAD described herein is that it provides a stimulation regimen that can be defined with just 5 parameters, as taught below in connection with FIGS. 15A and 15B. This allows the programming features of the micro-controller to be carried out in a simple and straight-forward manner.

The micro-controller U2 primarily performs the function of generating the digital signal that shuts down the boost converter to prevent too much instantaneous current from being drawn from the battery $V_{BAT}$. The micro-controller U2 also controls the generation of the stimulus pulses at the desired pulse width and frequency. It further keeps track of the time periods associated with a stimulation session, i.e., when a stimulation session begins and when it ends.

The micro-controller U2 also controls the amplitude of the stimulus pulse. This is done by adjusting the value of a current generated by a Programmable Current Source U3. In one embodiment, U3 is realized with a voltage controlled current source IC. In such a voltage controlled current source, the programmed current is set by a programmed voltage appearing across a fixed resistor R5, i.e., the voltage appearing at the "OUT" terminal of U3. This programmed voltage, in turn, is set by the voltage applied to the "SET" terminal of U3. That is, the programmed current source U3 sets the voltage at the "OUT" terminal to be equal to the voltage applied to the "SET" terminal. The programmed current that flows through the resistor R5 is then set by Ohms Law to be the voltage at the "set" terminal divided by R5. As the voltage at the "set" terminal changes, the current flowing through resistor R5 at the "OUT" terminal changes, and this current is essentially the same as the current pulled through the closed switch M1, which is essentially the same current flowing through the load $R_{LOAD}$. Hence, whatever current flows through resistor R5, as set by the voltage across resistor R5, is essentially the same current that flows through the load $R_{LOAD}$. Thus, as the micro-controller U2 sets the voltage at the "set" terminal of U3, on the signal line labeled "AMPSET", it controls what current flows through the load $R_{LOAD}$. In no event can the amplitude of the voltage pulse developed across the load $R_{LOAD}$ exceed the voltage $V_{OUT}$ developed by the boost converter less the voltage drops across the switches and current source.

The switches $S_R$ and $S_P$ described previously in connection with FIGS. 10, 11 and 12 are realized with transistor switches M1, M2, M3, M4, M5 and M6, each of which is controlled directly or indirectly by control signals generated by the micro-controller circuit U2. For the embodiment shown in FIG. 13A, these switches are controlled by two signals, one appearing on signal line 234, labeled PULSE, and the other appearing on signal line 236, labeled RCHG (which is an abbreviation for "recharge"). For the circuit configuration shown in FIG. 13A, the RCHG signal on signal line 236 is always the inverse of the PULSE signal appearing on signal line 234. This type of control does not allow both switch M1 and switch M2 to be open or closed at the same time. Rather, switch M1 is closed when switch M2 is open, and switch M2 is closed, when switch M1 is open. When switch M1 is closed, and switch M2 is open, the stimulus pulse appears across the load, $R_{LOAD}$, with the current flowing through the load, $R_{LOAD}$, being essentially equal to the current flowing through resistor R5. When the switch M1 is open, and switch M2 is closed, no stimulus pulse appears across the load, and the coupling capacitors C5 and C6 are recharged through the closed switch M2 and resistor R6 to the voltage $V_{OUT}$ in anticipation of the next stimulus pulse.

The circuitry shown in FIG. 13A is only exemplary of one type of circuit that may be used to control the pulse width, amplitude, frequency, and duty cycle of stimulation pulses applied to the load, $R_{LOAD}$. Any type of circuit, or control, that allows stimulation pulses of a desired magnitude (measured in terms of pulse width, frequency and amplitude, where the amplitude may be measured in current or voltage) to be applied through the electrodes to the patient at the specified acupoint at a desired duty cycle (stimulation session duration and frequency) may be used. However, for the circuitry to perform its intended function over a long period of time, e.g., years, using only a small energy source, e.g., a small coin-sized battery having a high battery impedance and a relatively low capacity, the circuitry must be properly managed and controlled to prevent excessive current draw from the battery.

In some examples, the circuitry used in the IEAD 100, e.g., the circuitry shown in FIGS. 10, 11, 12, 13A, or equivalents thereof, have some means for controlling the stimulation current that flows through the load, $R_{LOAD}$, which load may be characterized as the patient's tissue impedance at and around the acupoint being stimulated. This tissue impedance, as shown in FIGS. 11 and 12, may typically vary from between about 300 ohms to 2000 ohms. Moreover, it not only varies from one patient to another, but it varies over time. Hence, there is a need to control the current that flows through this variable load, $R_{LOAD}$. One way of accomplishing this goal is to control the stimulation current, as opposed to the stimulation voltage, so that the same current will flow through the tissue load regardless of changes that may occur in the tissue impedance over time. The use of a voltage controlled current source U3, as shown in FIG. 13A, is one way to satisfy this need.

Still referring to FIG. 13A, a fourth IC U4 is connected to the micro-controller U2. For the embodiment shown in FIG. 13A, the IC U4 is an electromagnetic field sensor, and it allows the presence of an externally-generated (non-implanted) electromagnetic field to be sensed. An "electromagnetic" field, for purposes of this application includes magnetic fields, radio frequency (RF) fields, light fields, and the like. The electromagnetic sensor may take many forms, such as any wireless sensing element, e.g., a pickup coil or RF detector, a photon detector, a magnetic field detector, and the like. When a magnetic sensor is employed as the electromagnetic sensor U4, the magnetic field is generated using an External Control Device (ECD) 240 that communicates wirelessly, e.g., through the presence or absence of a magnetic field, with the magnetic sensor U4. (A magnetic field, or other type of field if a magnetic field is not used, is symbolically illustrated in FIG. 13A by the wavy line 242.) In its simplest form, the ECD 240 may simply be a magnet, and modulation of the magnetic field is achieved simply by placing or removing the magnet next to or away from the IEAD. When other types of sensors (non-magnetic) are employed, the ECD 240 generates the appropriate signal or field to be sensed by the sensor that is used.

Use of the ECD 240 provides a way for the patient, or medical personnel, to control the IEAD 100 after it has been implanted (or before it is implanted) with some simple commands, e.g., turn the IEAD ON, turn the IEAD OFF, increase the amplitude of the stimulation pulses by one increment, decrease the amplitude of the stimulation pulses by one increment, and the like. A simple coding scheme may be used to differentiate one command from another. For example, one coding scheme is time-based. That is, a first command is communicated by holding a magnet near the IEAD 100, and hence near the magnetic sensor U4 contained within the IEAD 100, for differing lengths of time. If, for example, a magnet is held over the IEAD for at least 2 seconds, but no more than 7 seconds, a first command is communicated. If a magnet is held over the IEAD for at least 11 seconds, but no more than 18 seconds, a second command is communicated, and so forth.

Another coding scheme that could be used is a sequence-based coding scheme. That is, application of 3 magnetic pulses may be used to signal one external command, if the sequence is repeated 3 times. A sequence of 2 magnetic pulses, repeated twice, may be used to signal another external command. A sequence of one magnetic pulse, followed by a sequence of two magnetic pulses, followed by a sequence of three magnetic pulses, may be used to signal yet another external command.

Other simple coding schemes may also be used, such as the letters AA, RR, HO, BT, KS using international Morse code. That is, the Morse code symbols for the letter "A" are dot dash, where a dot is a short magnetic pulse, and a dash is a long magnetic pulse. Thus, to send the letter A to the IEAD 100 using an external magnet, the user would hold the magnet over the area where the IEAD 100 is implanted for a short period of time, e.g., one second or less, followed by holding the magnet over the IEAD for a long period of time, e.g., more than one second.

More sophisticated magnetic coding schemes may be used to communicate to the micro-controller chip U2 the operating parameters of the IEAD 100. For example, using an electromagnet controlled by a computer, the pulse width, frequency, and amplitude of the EA stimulation pulses used during each stimulation session may be pre-set. Also, the frequency of the stimulation sessions can be pre-set. Additionally, a master reset signal can be sent to the device in order to re-set these parameters to default values. These same operating parameters and commands may be re-sent at any time to the IEAD 100 during its useful lifetime should changes in the parameters be desired or needed.

Figure 13B:
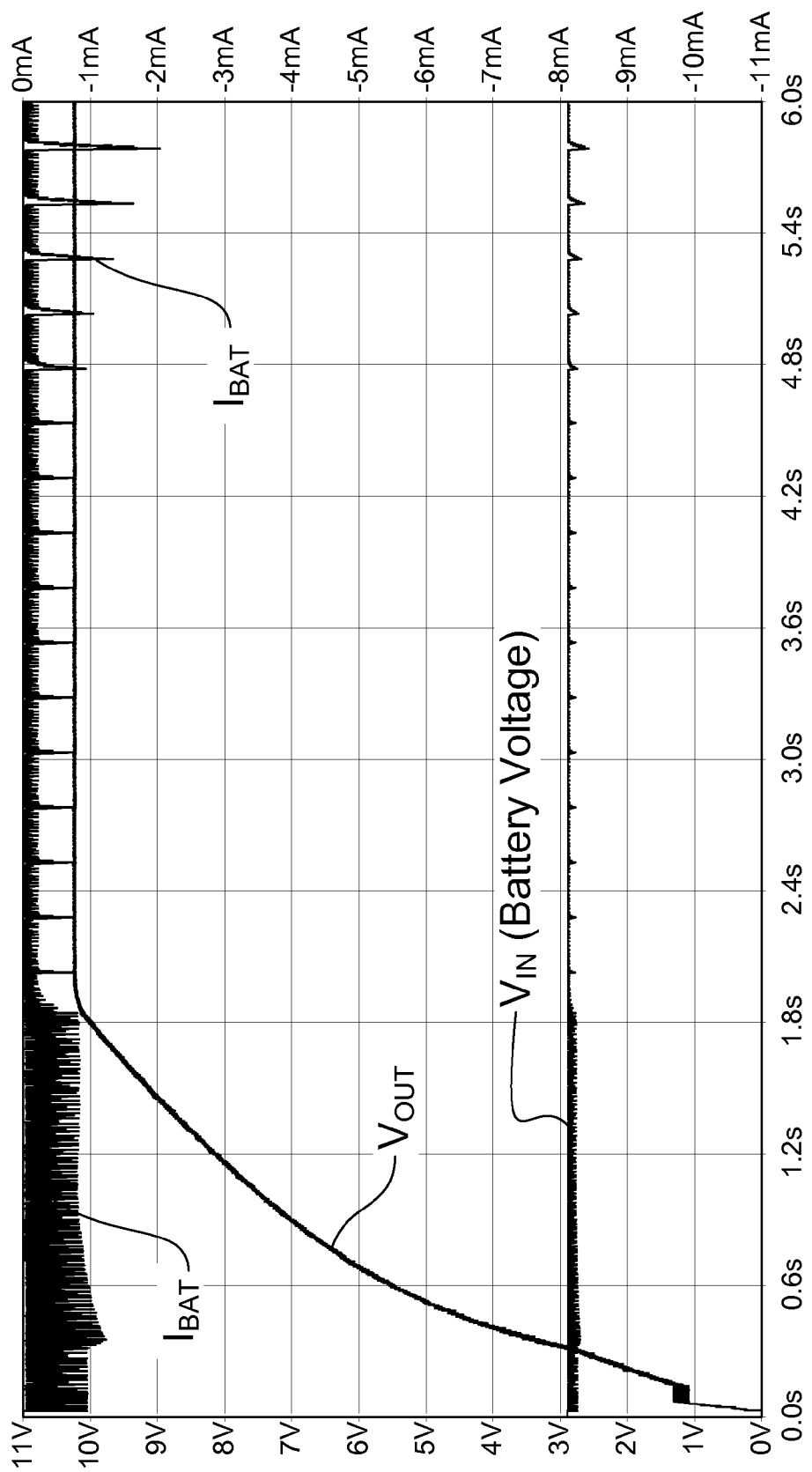
FIG. 13B shows current and voltage waveforms associated with the operation of the circuit shown in FIG. 13A.

The current and voltage waveforms associated with the operation of the IEAD circuitry of FIG. 13A are shown in FIG. 13B. In FIG. 13B, the horizontal axis is time, the left vertical axis is voltage, and the right vertical axis is current. The battery in this example has 160 Ohms of internal impedance.

Referring to FIGS. 13A and 13B, during startup, the boost converter ON time is approximately 30 microseconds applied every 7.8 milliseconds. This is sufficient to ramp the output voltage $V_{OUT}$ up to over 10 V within 2 seconds while drawing no more than about 1 mA from the battery and inducing only 150 mV of input voltage ripple.

The electroacupuncture (EA) simulation pulses resulting from operation of the circuit of FIG. 13A have a width of 0.5 milliseconds and increase in amplitude from approximately 1 mA in the first pulse to approximately 15 mA in the last pulse. The instantaneous current drawn from the battery is less than 2 mA for the EA pulses and the drop in battery voltage is less than approximately 300 mV. The boost converter is enabled (turned ON) only during the instantaneous output current surges associated with the 0.5 milliseconds wide EA pulses.

Figure 14:
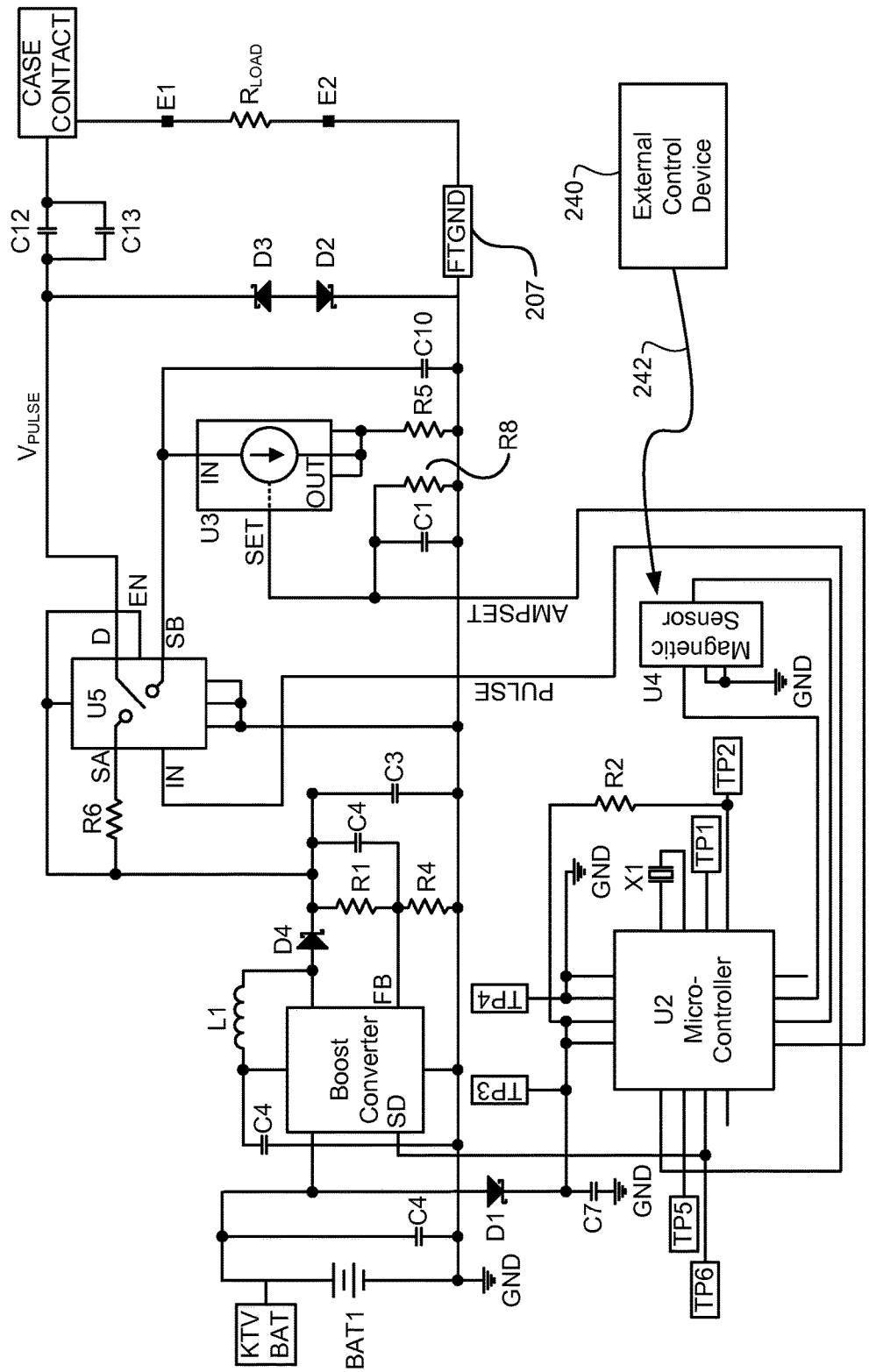
FIG. 14 shows another exemplary schematic configuration for an IEAD similar to that shown in FIG. 13A, but which uses an alternate output circuitry configuration for generating the stimulus pulses.

Another exemplary embodiment of the circuitry used in an implantable electroacupuncture device (IEAD) 100 that employs a digital control signal as taught herein is shown in the schematic diagram of FIG. 14. The circuit shown in FIG. 14 is, in most respects, very similar to the circuit described previously in connection with FIG. 13A. What is new in FIG. 14 is the inclusion of a Schottky diode D4 at the output terminal LX of the boost convertor U1 and the inclusion of a fifth integrated circuit (IC) U5 that essentially performs the same function as the switches M1-M6 shown in FIG. 13A.

The Schottky diode D4 helps isolate the output voltage $V_{OUT}$ generated by the boost converter circuit U1. This is advantageous in applications where the boost converter circuit U1 is selected and operated to provide an output voltage $V_{OUT}$ that is four or five times as great as the battery voltage, $V_{BAT}$. For example, in the embodiment for which the circuit of FIG. 14 is designed, the output voltage $V_{OUT}$ is designed to be nominally 15 volts using a battery that has a nominal battery voltage of only 3 volts. (In contrast, the embodiment shown in FIG. 13A is designed to provide an output voltage that is nominally 10-12 volts, using a battery having a nominal output voltage of 3 volts.)

The inclusion of the fifth IC U5 in the circuit shown in FIG. 14 is, as indicated, used to perform the function of a switch. The other ICs shown in FIG. 14, U1 (boost converter), U2 (micro-controller), U3 (voltage controlled programmable current source) and U4 (electromagnetic sensor) are basically the same as the IC's U1, U2, U3 and U4 described previously in connection with FIG. 13A.

The IC U5 shown in FIG. 14 functions as a single pole/double throw (SPDT) switch. Numerous commercially-available ICs may be used for this function. For example, an ADG1419 IC, available from Analog Devices Incorporated (ADI) may be used. In such IC U5, the terminal "D" functions as the common terminal of the switch, and the terminals "SA" and "SB" function as the selected output terminal of the switch. The terminals "IN" and "EN" are control terminals to control the position of the switch. Thus, when there is a signal present on the PULSE line, which is connected to the "IN" terminal of U5, the SPDT switch U5 connects the "D" terminal to the "SB" terminal, and the SPDT switch U5 effectively connects the cathode electrode E1 to the programmable current source U3. This connection thus causes the programmed current, set by the control voltage AMPSET applied to the SET terminal of the programmable current source U3, to flow through resistor R5, which in turn causes essentially the same current to flow through the load, $R_{LOAD}$, present between the electrodes E1 and E2. When a signal is not present on the PULSE line, the SPDT switch U5 effectively connects the cathode electrode E1 to the resistor R6, which allows the coupling capacitors C12 and C13 to recharge back to the voltage $V_{OUT}$ provided by the boost converter circuit U2.

Figure 14A:
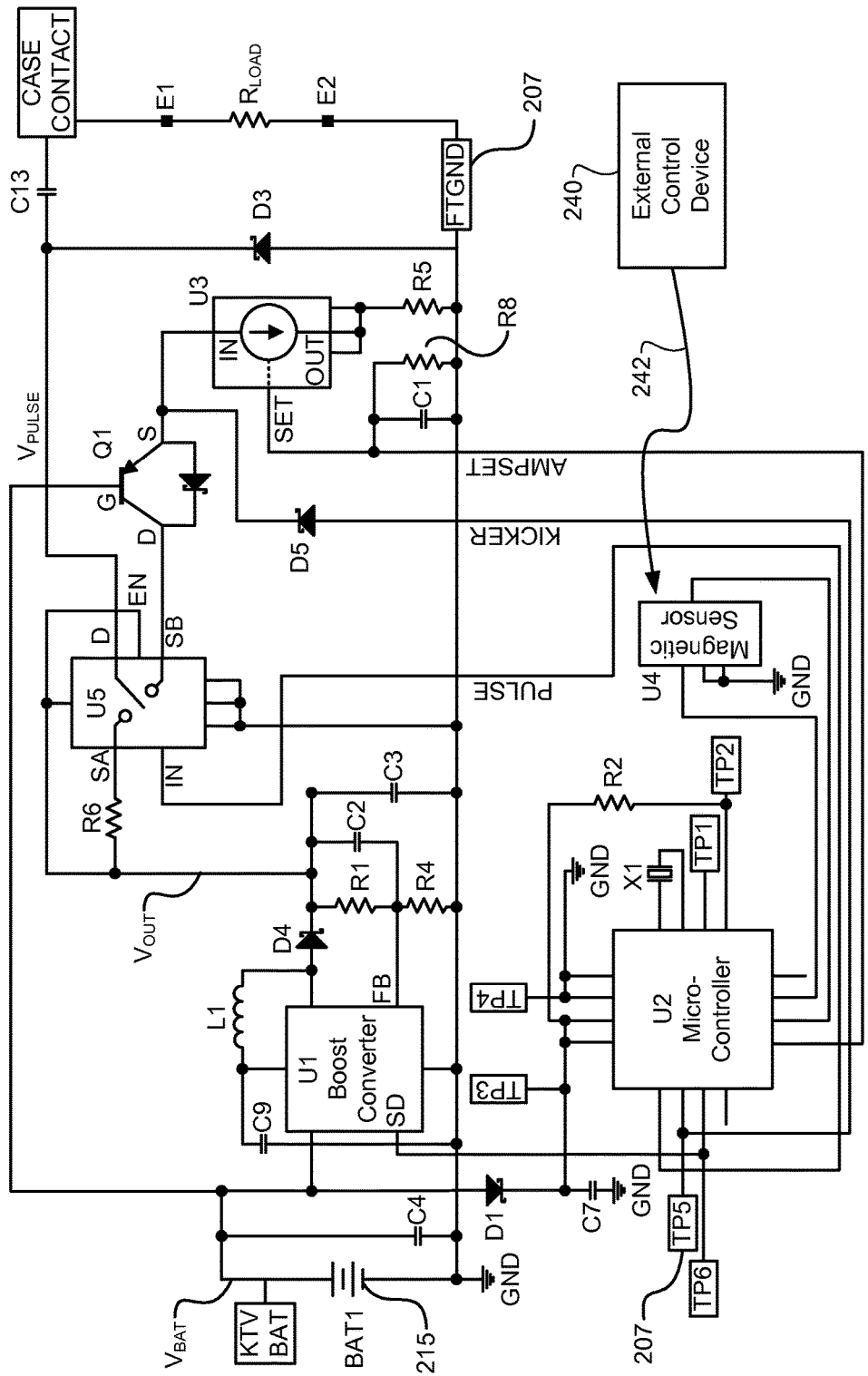
FIG. 14A depicts yet a further exemplary schematic configuration for an IEAD similar to that shown in FIG. 13A or FIG. 14, but which includes additional enhancements and circuit features.

Yet another exemplary embodiment of the circuitry used in an implantable electroacupuncture device (IEAD) 100 that employs an ON-OFF approach to duty-cycle modulate the boost converter as a tool for limiting the amount of instantaneous battery current drawn from the high impedance battery 215 is shown in the schematic diagram of FIG. 14A. The circuit shown in FIG. 14A is, in most respects, very similar to, or the same as, the circuit described previously in connection with FIG. 14 or FIG. 13A, and that description will not be repeated here. What is new in FIG. 14A are the addition of elements and features that address additional issues associated with the operation of an IEAD 100.

One feature included in the circuitry of FIG. 14A, which is described briefly above in connection with the description of FIG. 10, is that the boost converter circuit U1 is modulated ON and OFF using digital control generated within the boost converter circuit U1 itself. In accordance with this variation, the boost converter circuit 200 shuts itself down whenever the battery voltage falls below a predetermined level above that required by the remaining circuitry. For example, in the embodiment shown in FIG. 14A, the boost converter circuit U1 is realized using a MAX8570 boost converter IC, commercially available from Maxim, or equivalents thereof. This particular boost converter IC shuts down when the applied voltage, $V_{BAT}$, falls below 2.5 V. Advantageously, a battery voltage of 2.5 volts is still a high enough voltage to ensure the microcontroller IC U2, and other circuitry associated with the operation of the IEAD 100, remain operational.

Thus, in operation, as soon as the battery voltage drops below 2.5 volts, the boost converter circuit U1 shuts down, thereby limiting the instantaneous current drawn from the battery. When the boost converter U1 shuts down, the instantaneous battery current drawn from the battery is immediately reduced a significant amount, thereby causing the battery voltage $V_{BAT}$ to increase.

As the battery voltage $V_{BAT}$ increases, the boost converter circuit U1 remains shut down until the microcontroller U2 determines that it is time to turn the boost converter back ON. This turn ON typically occurs in one of two ways: (1) just prior to the delivery of the next stimulus pulse, a turn ON signal may be applied to the Shutdown ("SD") terminal, signal line 243, of the boost converter circuit U1; or (2) as soon as the battery voltage, $V_{BAT}$, has increased a sufficient amount, as sensed at the feedback terminal FB of the boost converter circuit U1, the circuits within the boost converter circuit U1 are automatically turned back ON, allowing the output voltage $V_{OUT}$ to build up to a voltage level needed by the switch circuit U5 and the current source circuit U3 to generate an output stimulus pulse of the desired amplitude when the next PULSE signal is applied to the IN terminal of the switch U5 by the microcontroller U2.

Once turned ON, the boost converter remains ON until, again, the input voltage drops below 2.5 volts. This pattern continues, with the boost converter being ON for a short time, and OFF for a much longer time (typically, the duty cycle associated with this ON/OFF operation of the boost converter circuit U1 is no greater than about 0.01), thereby controlling and limiting the amount of current that is drawn from the battery. This ON/OFF action of U1 assures that the battery voltage, $V_{BAT}$, always remains sufficiently high to permit operation of all the critical circuits of the IEAD 100 (principally the circuits of the microcontroller U2), except the boost converter circuit U1.

In an exemplary implementation, the microcontroller circuit U2 used in FIG. 14A comprises an MSP43002452IRSA 16 microcontroller, commercially available from Texas Instruments, or equivalent microcontroller The current source circuit U3 comprises a LT3092 programmable current source commercially available form Linear Technology, or equivalents thereof. The sensor circuit U4 comprises an AS-M15SA-R magnetic sensor, commercially available from Murata, or equivalents thereof. And, the switch circuit U5 comprises an ADG1419BCPZ single pole double throw analog switch commercially available from Analog Devices, or equivalents thereof.

Another feature or enhancement provided by the circuit implementation depicted in FIG. 14A relates to removing, or at least minimizing, some undesirable leading edge transients that are seen in the output stimulus pulses generated by the circuitry of FIG. 14A. The solution to remove or mitigate the occurrence of such leading edge transients is to insert an N-MOSFET transistor switch Q1 at the input terminal, IN, of the programmable current source circuit U3. This switch Q1 acts as a "cascode" stage that maintains a more constant voltage across the current source U3 as the output current and/or load resistance changes. The gate (G) terminal of the switch Q1 is driven by the battery voltage, $V_{BAT}$, which means the voltage at the source terminal (S) of switch Q1, which is connected to the IN terminal of the current source U3, is limited to roughly $V_{BAT}$-$V_{GS}$, where $V_{GS}$ is the threshold voltage across the gate(G)-source(S) terminals of Q1.

Use of this N-MOSFET switch Q1 as depicted in FIG. 14A advantageously reduces the transient leading edge of the stimulus pulse because the capacitance looking into Q1 is much less than is seen when looking into the current source circuit U3 because of the Miller effect. That is, there is considerable loop gain in the operation of the U3 current source circuit to servo the current. This loop gain directly scales the input capacitance so that there is a much larger leading edge spike on the pulse. This in turn causes a 30 to 40 microsecond transient at the leading edge of the current pulse as the current source U3 recovers current regulation.

Figure 14B:
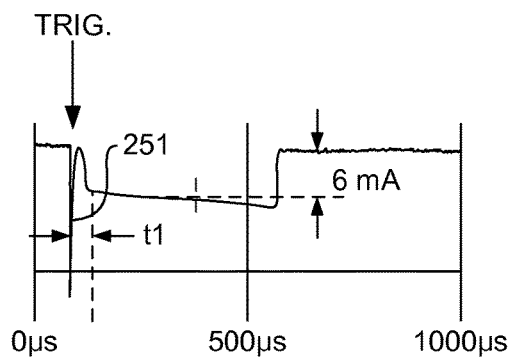
FIGS. 14B and 14C show timing waveform diagrams that illustrate the operation of the circuit of FIG. 14 before (FIG. 14B) and after (FIG. 14C) the addition of a cascode stage to the IEAD circuitry that removes some undesirable transients from the leading edge of the stimulus pulse.

An example of this leading edge transient is illustrated in the timing waveform diagram of FIG. 14B. In FIG. 14B (as well as in FIGS. 14C, 14D and 14E, which all show similar timing waveform diagrams), the horizontal axis is time and the vertical axis is voltage, which (assuming a resistive load of 600 ohms) may readily be converted to current, as has been done in these figures. The stimulus pulse begins at a trigger location near the left edge of the waveform, labeled TRIG. As seen in FIG. 14B, immediately after the trigger point, which should mark the beginning or leading edge of the stimulus pulse, an initial spike 251 occurs that has a magnitude on the order of twice the amplitude of the stimulus pulse. This spike 251 shoots down (as the waveform is oriented in the figures) and then shoots back up, and eventually, after a delay of t1 microseconds, becomes the leading edge of the pulse. The delay t1 is about 30-40 microseconds, which means that the leading edge of the stimulus pulse is delayed 30-40 microseconds. Having a leading edge delay of this magnitude is not a desirable result.

Figure 14C:
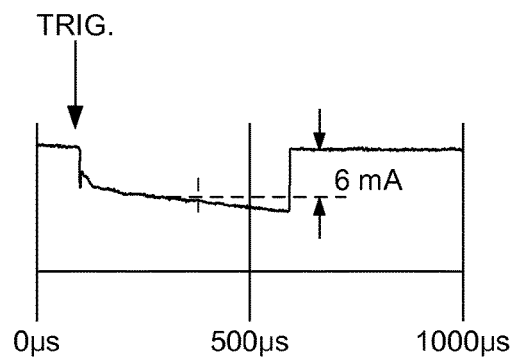

Next, with the cascode stage (comprising the switch Q1) connected to the input terminal, IN, of the current source U3, the stimulus pulse is again illustrated. Because the cascode stage significantly reduces the input capacitance looking into the drain (D) terminal of the switch Q1, the leading edge transient is significantly reduced, as illustrated in the timing waveform diagram of FIG. 14C. As seen in FIG. 14C, the leading edge transient has all but disappeared, and the delay t1 between the trigger point and the leading edge of the stimulus pulse is negligible.

Figure 14D:
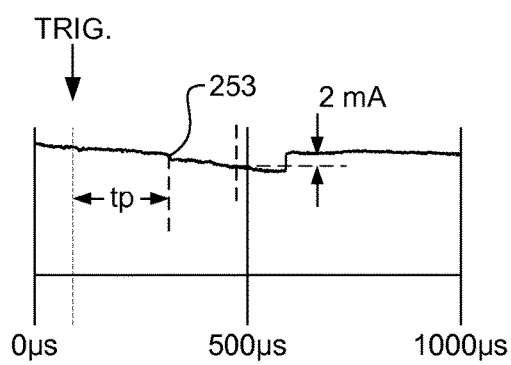
FIGS. 14D and 14E illustrate timing waveform diagrams that show the operation of the circuit of FIG. 14 before (FIG. 14D) and after (FIG. 14E) the addition of circuitry that addresses a delay when starting the current regulator U3 for low amplitude stimulus pulses.

Another feature or enhancement provided by the circuitry of FIG. 14A is to address a delay that is seen when starting up the programmable current source U3 at low pulse amplitudes, (e.g., less than about 3 mA). A typical current stimulus output for the IEAD is on the order of 15-25 mA. When a much smaller amplitude current stimulus is used, e.g., 1.5-3 mA, the control signal that defines this smaller amplitude pulse is significantly less than the one used to define the more typical stimulus amplitudes of 15-25 mA. Such a small control signal lengthens the delay, $t_D$, between the trigger point, TRIG, and the leading edge 253 of the stimulus pulse. FIG. 14D illustrates this long delay, $t_D$, which is on the order of 200 microseconds.

The address the problem illustrated in the waveform diagram of FIG. 14D, a Schottky diode D5 is connected in the circuit of FIG. 14A from an output port on the microcontroller circuit U2 to the input port, IN, of the current source circuit U3. In an exemplary implementation of the circuit of FIG. 14A, this Schottky diode D5 is realized using a BAT54XV2DKR diode, commercially available from Fairchild Semiconductor. This diode is used to warm-up or "kick start" the circuit U3 when the pulse amplitude is low so that there is less of a delay, $t_D$, before current is regulated at the start of the pulse. Since the cascode stage Q1 keeps the drop across U3 low, U3 can be driven directly from the microcontroller U2 at the start of the pulse without significantly changing the pulse characteristics (e.g., amplitude or timing) in such a way that the delay, $t_D$, before current is regulated at the start of the pulse can be reduced.

Figure 14E:
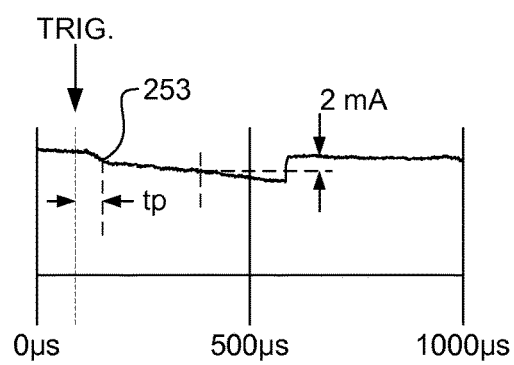

FIG. 14E illustrates the timing waveform diagram achieved using the circuit of FIG. 14A with the diode D5 inserted so as to allow the microcontroller U2 to directly drive, or "kick start", the current source circuit U3 at the start of the pulse. As seen in FIG. 14E, the delay, $t_D$, realized with the "kick start" has been significantly reduced from what it was without the "kick start" (as shown in FIG. 14D), e.g., from about 200 microseconds to about 40 microseconds, or less. Thus, this "kick start" feature shortens the undesired delay, $t_D$, by at least a factor of about 5.

An additional feature provided by the circuitry of FIG. 14A addresses a concern regarding EMI (electromagnetic interference). EMI can occur, for example, during electrocautery and/or external defibrillation. Should any of the circuit elements used within the IEAD 100, such as the analog switch U5, have a transient voltage exceeding approximately 0.3 V appear on its pins (which transient voltage could easily occur if the IEAD is subjected to uncontrolled EMI), then the IC could be damaged. To prevent such possible EMI damage, the output voltage pulse, appearing on the signal line labeled $V_{PULSE}$, is clamped to ground through the forward bias direction of the diode D3. In contrast, in the circuits shown in FIGS. 13A and 14, there are two zenor diodes, D2 and D3, connected back to back, to limit the voltage appearing on the $V_{PULSE}$ line to voltages no greater than the zenor diode voltage in either direction. As seen in FIG. 14A, diode D2 has been replaced with a short, thereby clamping the voltage that can appear on the output voltage line—the signal line where $V_{PULSE}$ appears—in one polarity direction to no greater than the forward voltage drop across the diode D3.

Figure 15:
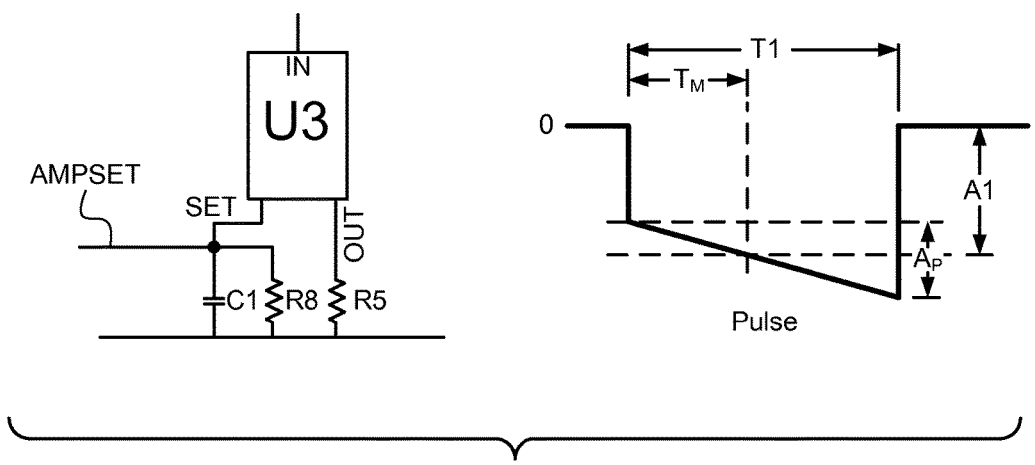
FIG. 15 shows a reverse trapezoidal waveform of the type that is generated by the pulse generation circuitry of the IEAD, and further illustrates one approach for achieving the desired reverse trapezoidal waveform shape.
Figure 15A:
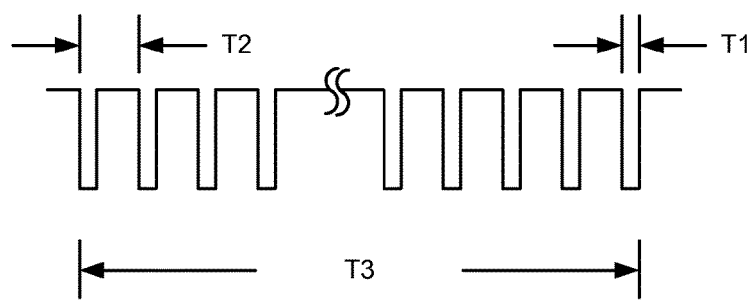
FIG. 15A shows a timing waveform diagram of representative EA stimulation pulses generated by the IEAD device during a stimulation session.

As is evident from the waveforms depicted in FIGS. 14B, 14C, 14D and 14E, the basic current stimulus waveform is not a square wave, with a "flat top", (or, in the case of a negative current waveform, with a "flat bottom") as depicted in most simplified waveform diagrams (see, e.g., FIG. 15A). Rather, the current stimulus waveforms shown in FIGS. 14B, 14C, 14D and 14E have what the inventors refer to as a reverse trapezoidal shape. That is, the current waveforms start at a first value, at the leading edge of the pulse, and gradually ramp to a second, larger, value at the trailing edge of the pulse (i.e., the current increases during the pulse). For a negative-going pulse, as is shown in these figures, the ramp slopes downward, but this corresponds to the amplitude of the pulse getting larger.

This pulse shape—a reverse trapezoidal shape—for the current stimulus pulse is by design. That is, the inventors want the current to increase during the pulse because such shape is believed to be more selective for the recruitment of smaller fiber diameter tissue and nerves, and thus has the potential to be more effective in achieving its intended goal of activating desired tissue at the target tissue location.

The reverse trapezoidal stimulus pulse shape is illustrated in more detail in FIG. 15, as is one manner for achieving it. Shown on the right side of FIG. 15 is a sketch of reverse trapezoidal pulse. (Note, it is referred to as a "reverse trapezoidal" pulse because the current, or waveform, gets larger or increases during the pulse. This is in contrast to a conventional voltage regulated pulse, which is "trapezoidal", but in the other direction, i.e., the current decreases during the pulse.) As seen in FIG. 15, the reverse trapezoidal pulse has a duration T1, but the magnitude (amplitude) of the current during the pulse increases from a first value at the leading edge of the pulse to a second value at the trailing edge of the pulse. The increase in current from the leading edge of the pulse to the trailing edge is a value $A_P$. The average amplitude of the pulse during the pulse time T1 is a value A1, which is typically measured at a time $T_M$, which is about in the middle of the pulse. That is, $T_M = \frac{1}{2}T1$.

Also shown in FIG. 15, on the left side, is the circuitry that is used to create the reverse trapezoidal waveform. This circuitry is part of the circuitry shown, e.g., in FIG. 14A, and includes a capacitor C1 in parallel with a large resistor R8 (270 KΩ) connected to the "set" terminal of the programmable current source U3. The "AMPSET" signal, generated by the micro-controller circuit U2 to set the amplitude A1 of the current stimulus pulse to be generated, is applied to the "set" terminal of U3. When enabled by the AMPSET signal, the capacitor C1 starts to charge up during the pulse at a rate of approximately 10 μA (which comes from the "set" pin of U3, i.e., from the circuitry inside of U3). For C1=0.1 microfarads, this turns out to be 100 mV/ms, or 50 mV for a pulse having a pulse duration or width (T1) of 0.5 ms. Since the pulse current is approximately equal to $V_{SET}/R5$, the pulse current will increase by 50 mV/R5. Or, where R5 is 22 ohms, this increase in current turns out to be 50 mV/22=2.27 mA at the end of the 0.5 ms pulse. This increase is essentially fixed regardless of the programmed pulse amplitude.

While the circuitry described above performs the intended function of causing the current stimulus pulse to have a reverse trapezoidal shape in a simple and straightforward manner, it should be noted that there are other circuits and techniques that could also be used to achieve this same result. Moreover, it would be possible to directly control the shape of the $V_{SET}$ signal during the pulse duration in order to create any desired stimulus pulse shape.

From the above description, it is seen that an implantable IEAD 100 is provided that uses a digital control signal to duty-cycle limit the instantaneous current drawn from the battery by a boost converter. Three different exemplary configurations (FIGS. 10, 11 and 12) are taught for achieving this desired result, and three exemplary circuit designs that may be used to realize this result have been disclosed (FIGS. 13A, 14 and 14A). One configuration (FIG. 12) teaches the additional capability to delta-sigma modulate the boost converter output voltage.

Delta-sigma modulation is well described in the art. Basically, it is a method for encoding analog signals into digital signals or higher-resolution digital signals into lower-resolution digital signals. The conversion is done using error feedback, where the difference between the two signals is measured and used to improve the conversion. The low-resolution signal typically changes more quickly than the high-resolution signal and it can be filtered to recover the high resolution signal with little or no loss of fidelity. Delta-sigma modulation has found increasing use in modern electronic components such as converters, frequency synthesizers, switched-mode power supplies and motor controllers. See, e.g., Wikipedia, *Delta-sigma modulation*.

Use and Operation

With the implantable electroacupuncture device (IEAD) 100 in hand, the IEAD 100 may be used most effectively to treat chronic low back pain by first pre-setting stimulation parameters that the device will use during a stimulation session. FIG. 15A shows a timing waveform diagram illustrating the EA stimulation parameters used by the IEAD to generate EA stimulation pulses. As seen in FIG. 15A, there are basically four parameters associated with a stimulation session. The time T1 defines the duration (or pulse width) of a stimulus pulse. The time T2 defines the time between the start of one stimulus pulse and the start of the next stimulus pulse. The time T2 thus defines the period associated with the frequency of the stimulus pulses. The frequency of the stimulation pulses is equal to 1/T2. The ratio of T1/T2 is typically quite low, e.g., less than 0.01. The duration of a stimulation session is defined by the time period T3. The amplitude of the stimulus pulses is defined by the amplitude A1. This amplitude may be expressed in either voltage or current.

Figure 15B:
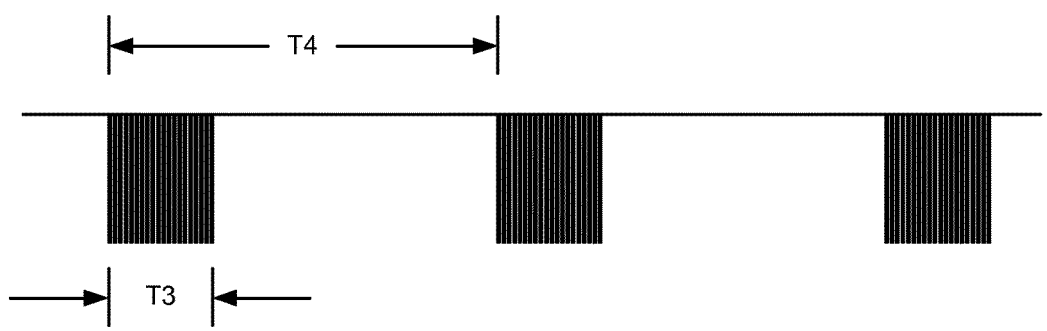
FIG. 15B shows a timing waveform diagram of multiple stimulation sessions, and illustrates the waveforms on a more condensed time scale.

Turning next to FIG. 15B, a timing waveform diagram is shown that illustrates the manner in which the stimulation sessions are administered in accordance with an exemplary stimulation regimen. FIG. 15B shows several stimulation sessions of duration T3, and how often the stimulation sessions occur. The stimulation regimen thus includes a time period T4 which sets the time period from the start of one stimulation session to the start of the next stimulation session. T4 thus is the period of the stimulation session frequency, and the stimulation session frequency is equal to 1/T4.

In order to allow the applied stimulation to achieve its desired effect on the body tissue at the selected target stimulation site, the period of the stimulation session T4 may be varied when the stimulation sessions are first applied. This can be achieved by employing a simple algorithm within the circuitry of the EA device that changes the value of T4 in an appropriate manner. For example, at start up, the period T4 may be set to a minimum value, T4 (min). Then, as time goes on, the value of T4 is gradually increased until a desired value of T4, T4 (final) is reached.

By way of example, if T4 (min) is 1 day, and T4 (final) is 7 days, the value of T4 may vary as follows once the stimulation sessions begin: T4=1 day for the duration between the first and second stimulation sessions, then 2 days for the duration between the second and third stimulation sessions, then 4 days for the duration between the third and fourth stimulation sessions, and then finally 7 days for the duration between all subsequent stimulation sessions after the fourth stimulation session.

Rather than increasing the value of T4 from a minimum value to a maximum value using a simple doubling algorithm, as described in the previous paragraph, an enhancement is to use a table of session durations and intervals whereby the automatic session interval can be shorter for the first week or so. For example the $1^{st}$ 30 minute session could be delivered after 1 day. The $2^{nd}$ 30 minute session could be delivered after 2 days. The $3^{rd}$ 30 minute session could be delivered after 4 days. Finally, the $4^{th}$ 30 minute session could be delivered for all subsequent sessions after 7 days.

If a triggered session is delivered completely, it advances the therapy schedule to the next table entry.

Another enhancement is that the initial set amplitude only takes effect if the subsequent triggered session is completely delivered. If the first session is aborted by a magnet application, the device reverts to a Shelf Mode. In this way, the first session is always a triggered session that occurs in the clinician setting.

Finally, the amplitude and place in the session table are saved in non-volatile memory when they change. This avoids a resetting of the therapy schedule and need to reprogram the amplitude in the event of a device reset.

An exemplary set of parameters that could be used to define a stimulation regimen is as follows:
T1=0.5 milliseconds
T2=500 milliseconds
T3=30 minutes
T4=7 days (10,080 minutes)
A1=15 volts (across 1 KΩ), or 15 milliamps (mA)

For treating chronic low back pain, exemplary ranges for each of the above parameters in accordance with one stimulation strategy are as follows:
T1=0.1 to 2.0 milliseconds (ms)
T2=67 to 1000 ms (15 Hz to 1 Hz)
T3=20 to 60 minutes
T4=1,440 to 10,080 minutes (1 day to 1 week)
A1=1 to 15 mA Another way for treating chronic low back pain is to toggle the simulation frequency between a relatively low rate of stimulation, e.g., 1 to 2 Hz, and then a higher rate of stimulation, e.g., 15 to 30 Hz, or higher (e.g., up to 100 Hz). One way in which this toggling between a low rate and a high rate may be achieved is depicted schematically in FIG. 15C.

Figure 15C:
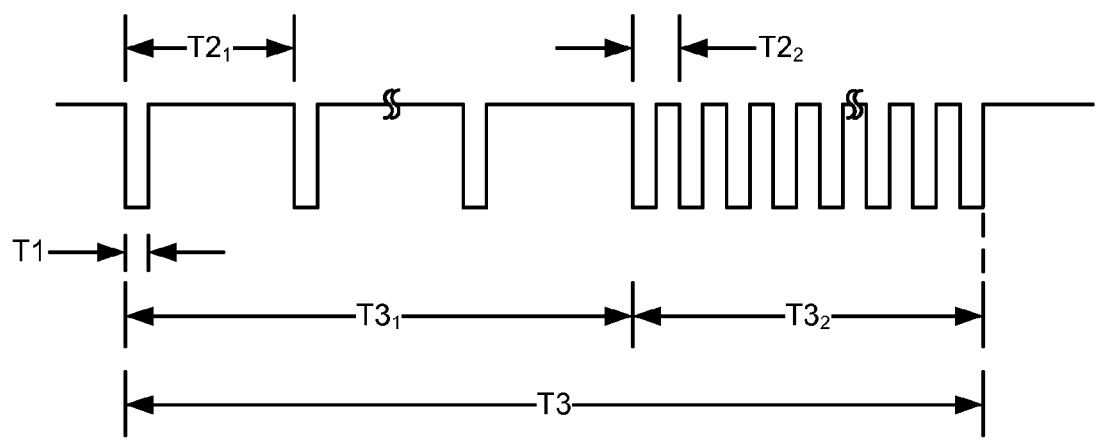
FIG. 15C shows a timing waveform diagram similar to FIG. 15A, but wherein the stimulation session is divided into two sub-sessions, one sub-session with stimulation being applied at a first frequency, and the other sub-session having stimulation applied at a second frequency.

As seen in FIG. 15C, the stimulation session occurs during a time period T3, the same as is shown in FIG. 15A. However, unlike FIG. 15A, the stimulation session T3 is further divided into two time periods, $T3_1$ and $T3_2$. During the time period $T3_1$, the frequency of stimulation is lower than it is during the time period $T3_2$. While the duration of the actual stimulation pulse T1 does not typically change, the time period between stimulation pulses, T2, does change. Thus, for a lower frequency of stimulation, as occurs during time period $T3_1$, the period of the stimulation is a time $T2_1$. The time $T2_1$ is long compared the period of stimulation, $T2_2$, that occurs during time period $T3_2$. The time period $T2_1$, for example, may be 0.5 sec, which corresponds to a stimulation frequency of 2 Hz; while the time period $T2_2$, on the other hand, may be 50 msec, which corresponds to a stimulation frequency of 20 Hz. The time period $T3_1$ may be, e.g., 15 minutes, and the time period $T3_2$ may be, e.g., 15 minutes, thus making the total time T3 of the stimulation session 30 minutes.

Representative values of the parameters shown in FIG. 15C in accordance with one stimulation regimen for treating lower back pain are as follows:
T1=0.2 to 2.0 ms
$T2_1$=1000 to 100 ms
$T2_2$=400 to 10 ms
$T3_1$=5 to 50 minutes
$T3_2$=5 to 50 minutes
A1=1 to 18 mA As a variation of the toggling approach shown in FIG. 15C, which uses a stimulation paradigm that switches or toggles between alternating frequencies, e.g., between a low frequency $F_L$ (e.g., 1-2 Hz) and a higher frequency $F_H$ (e.g., 15-30 Hz), the low frequency stimulation at frequency $F_L$ may be provided during a stimulation session for approximately 3 to 6 seconds and then the higher frequency stimulation at frequency $F_H$ may be provided for approximately 3 to 6 seconds. This alternating of frequencies between $F_L$ and $F_H$ would then continue through the entire stimulation session (of duration T3 minutes).

It should also be noted that the alternating of frequencies between $F_L$ and $F_H$ could occur during alternate stimulation sessions. That is, a first stimulation session could stimulate at a frequency $F_L$, and the next stimulation session could stimulate at a frequency $F_H$.

The toggling or alternating between two stimulation frequencies during a stimulation session while treating lower back pain is beneficial because two different types of opioids are released, one when stimulating at a lower frequency, e.g., 1 to 2 Hz, and another when stimulating at a higher frequency, e.g., 15 Hz to 30 Hz. Both opioids help reduce the lower back pain the patient experiences.

It is to be emphasized that the values shown above for the stimulation regimen and ranges of stimulation parameters for use within the stimulation regimen are only exemplary. Other stimulation regimens that could be used, and the ranges of values that could be used for each of these parameters, are as defined in the claims.

It is also to be emphasized that the ranges of values presented in the claims for the parameters used with the methods and systems described herein have been selected after many months of careful research and study, and are not arbitrary. For example, the ratio of T3/T4, which sets the duty cycle, has been carefully selected to be very low, e.g., no more than 0.05. Maintaining a low duty cycle of this magnitude represents a significant change over what others have attempted in the implantable stimulator art. Not only does a very low duty cycle allow the battery itself to be small (coin cell size), which in turn allows the IEAD housing to be very small, which makes the IEAD ideally suited for being used without leads, thereby making it relatively easy to implant the device at the desired stimulation site (e.g., acupoint), but it also limits the frequency and duration of stimulation sessions.

Limiting the frequency and duration of the stimulation sessions recognizes that some treatments, such as treating chronic low back pain, are best done slowly and methodically, over time, rather than quickly and harshly using large doses of stimulation (or other treatments) aimed at forcing a rapid change in the patient's condition. Moreover, applying treatments slowly and methodically is more in keeping with traditional acupuncture methods (which, as indicated previously, are based on over 2500 years of experience). In addition, this slow and methodical conditioning is consistent with the time scale for remodeling of the central nervous system needed to produce the sustained therapeutic effect. Thus, the inventors have based their treatment regimens on the slow-and-methodical approach, as opposed to the immediate-and-forced approach adopted by many, if not most, prior art implantable electrical stimulators.

The inventors sometimes refer to their slow-and-methodical stimulation approach as "soft" stimulation, as opposed to the "hard" stimulation of the prior art, which focuses on an immediate-and-forced response.

Figure 16:
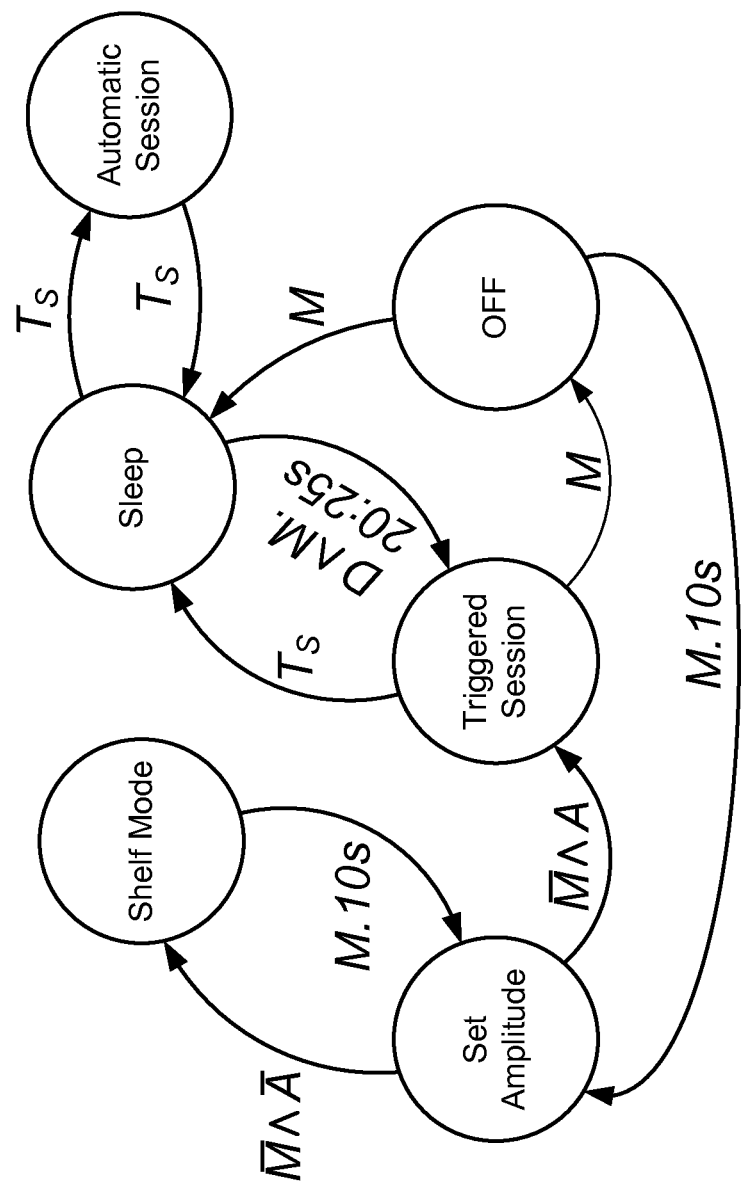
FIG. 16 shows a state diagram that depicts the various states the IEAD may assume as controlled by an external magnet.

Once the stimulation regimen has been defined and the parameters associated with it have been pre-set into the memory of the micro-controller circuit 220, the IEAD 100 needs to be implanted. Implantation is usually a relatively simple procedure, as has been practiced in the art After implantation, the IEAD must be turned ON, and otherwise controlled, so that the desired stimulation regimen or stimulation paradigm may be carried out. In one exemplary embodiment, control of the IEAD after implantation, as well as anytime after the housing of the IEAD has been hermetically sealed, is performed as shown in the state diagram of FIG. 16. Each circle shown in FIG. 16 represents an operating "state" of the micro-controller U2 (FIG. 13A or 14). As seen in FIG. 16, the controller U2 only operates in one of six states: (1) a "Set Amplitude" state, (2) a "Shelf Mode" state, (3) a "Triggered Session" state, (4) a "Sleep" state, (5) an "OFF" state, and an (6) "Automatic Session" state. The "Automatic Session" state is the state that automatically carries out the stimulation regimen using the pre-programmed parameters that define the stimulation regimen.

Shelf Mode is a low power state in which the IEAD is placed prior to shipment. After implant, commands are made through magnet application. Magnet application means an external magnet, typically a small hand-held cylindrical magnet, is placed over the location where the IEAD has been implanted. With a magnet in that location, the magnetic sensor U4 senses the presence of the magnet and notifies the controller U2 of the magnet's presence.

From the "Shelf Mode" state, a magnet application for 10 seconds (M. 10 s) puts the IEAD in the "Set Amplitude" state. While in the "Set Amplitude" state, the stimulation starts running by generating pulses at zero amplitude, incrementing every five seconds until the patient indicates that a comfortable level has been reached. At that time, the magnet is removed to set the amplitude.

If the magnet is removed and the amplitude is non-zero ($\overline{M} \wedge A$), the device continues into the "Triggered Session" so the patient receives the initial therapy. If the magnet is removed during "Set Amplitude" while the amplitude is zero ($\overline{M} \wedge \overline{A}$), the device returns to the Shelf Mode.

The Triggered Session ends and stimulation stops after the session time ($T_S$) has elapsed and the device enters the "Sleep" state. If a magnet is applied during a Triggered Session (M), the session aborts to the "OFF" state. If the magnet remains held on for 10 seconds (M. 10 s) while in the "OFF" state, the "Set Amplitude" state is entered with the stimulation level starting from zero amplitude as described.

If the magnet is removed ($\overline{M}$) within 10 seconds while in the OFF state, the device enters the Sleep state. From the Sleep state, the device automatically enters the Automatic Session state when the session interval time has expired ($T_I$). The Automatic Session delivers stimulation for the session time ($T_S$) and the device returns to the Sleep state. In this embodiment, the magnet has no effect once the Automatic Session starts so that the full therapy session is delivered.

While in the Sleep state, if a magnet has not been applied in the last 30 seconds (D) and a magnet is applied for a window between 20-25 seconds and then removed (M. 20:25 s), a Triggered Session is started. If the magnet window is missed (i.e. magnet removed too soon or too late), the 30 second de-bounce period (D) is started. When de-bounce is active, no magnet must be detected for 30 seconds before a Triggered Session can be initiated.

The session interval timer runs while the device is in Sleep state. The session interval timer is initialized when the device is woken up from Shelf Mode and is reset after each session is completely delivered. Thus abort of a triggered session by magnet application will not reset the timer, the Triggered Session must be completely delivered.

The circuitry that sets the various states shown in FIG. 16 as a function of externally-generated magnetic control commands, or other externally-generated command signals, is the micro-controller U2 (FIG. 14), the processor U2 (FIG. 13A), or the control circuit 220 (FIGS. 10, 11 and 12). Such processor-type circuits are programmable circuits that operate as directed by a program. The program is often referred to as "code", or a sequence of steps that the processor circuit follows. The "code" can take many forms, and be written in many different languages and formats, known to those of skill in the art. Representative "code" for the micro-controller U2 (FIG. 14) for controlling the states of the IEAD as shown in FIG. 16 is found in one of the appendices incorporated by reference herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A method of treating a chronic low back pain condition in a patient, comprising:
generating, by a leadless electroacupuncture device implanted beneath a skin surface of the patient at an acupoint corresponding to a target tissue location within the patient, stimulation sessions at a duty cycle that is less than 0.05, wherein
the acupoint comprises at least one of acupoints BL22, BL23, BL24, BL25, and B L26,
each stimulation session included in the plurality of stimulation sessions comprises a series of stimulation pulses,
the duty cycle is a ratio of T3 to T4,
each stimulation session included in the stimulation sessions has a duration of T3 minutes and occurs at a rate of once every T4 minutes, and
the leadless electroacupuncture device comprises a central electrode of a first polarity centrally located on a first surface of a housing of the electroacupuncture device and an annular electrode of a second polarity and that is spaced apart from the central electrode on the housing; and applying, by the leadless electroacupuncture device, the stimulation sessions to the target tissue location by way of the central electrode and the annular electrode in accordance with the duty cycle.

2. The method of claim 1, wherein the target tissue location comprises at least one of a lumbar nerve of the patient and a dorsal root ganglion of the patient.

3. The method of claim 1, wherein T3 is at least 10 minutes and less than 60 minutes, and wherein T4 is at least 1440 minutes and less than or equal to seven days.

4. The method of claim 1, further comprising receiving, by the electroacupuncture device from a device external to the electroacupuncture device, a control command that configures the electroacupuncture device for treating the chronic low back pain condition.

5. The method of claim 4, wherein the receiving of the control command comprises detecting, with a magnetic sensor included in the electroacupuncture device, a magnetic field generated by the device external to the electroacupuncture device.

6. The method of claim 1, wherein the housing is coin-sized and coin-shaped.

7. The method of claim 1, wherein the annular electrode is located on the first surface of the housing.

8. The method of claim 1, wherein the annular electrode comprises a ring electrode located around a perimeter edge of the housing.

9. The method of claim 1, wherein:
a catheter lead is electrically connected to the central electrode, the catheter lead having an electrode located at a distal end of the catheter lead and that functions as the central electrode; and
the applying of the stimulation sessions to the target tissue location further comprises applying the stimulation sessions by way the electrode of the catheter lead.

10. The method of claim 1, further comprising powering electronic circuits within the electroacupuncture device with a battery having an internal impedance of at least 5 ohms and no more than 160 ohms.

11. The method of claim 1, wherein the annular electrode surrounds the central electrode.

12. The method of claim 1, wherein the annular electrode forms a complete ring that surrounds the central electrode.

* * * * *